United States Patent
Kwan et al.

(10) Patent No.: US 11,752,139 B2
(45) Date of Patent: Sep. 12, 2023

(54) THERAPEUTIC COMBINATIONS OF ORALLY ADMINISTERED IRINOTECAN AND A P-GP INHIBITOR FOR THE TREATMENT OF CANCER

(71) Applicant: Athenex HK Innovative Limited, Sha Tin (HK)

(72) Inventors: Min-Fun Rudolf Kwan, Summit, NJ (US); E. Douglas Kramer, Stamford, CT (US); David Lawrence Cutler, Moorestown, NJ (US); Johnson Yiu-Nam Lau, Houston, TX (US); Wing Kai Chan, Hong Kong (CN)

(73) Assignee: Athenex HK Innovative Limited, Sha Tin (HK)

( * ) Notice: Subject to any disclaimer, the term of this patent is extended or adjusted under 35 U.S.C. 154(b) by 315 days.

(21) Appl. No.: 16/715,753

(22) Filed: Dec. 16, 2019

(65) Prior Publication Data
US 2020/0188363 A1 Jun. 18, 2020

Related U.S. Application Data

(60) Provisional application No. 62/846,829, filed on May 13, 2019, provisional application No. 62/780,110, filed on Dec. 14, 2018.

(51) Int. Cl.
*A61K 31/435* (2006.01)
*A61K 31/4745* (2006.01)
*A61P 35/00* (2006.01)
*A61P 35/02* (2006.01)

(52) U.S. Cl.
CPC ........ *A61K 31/435* (2013.01); *A61K 31/4745* (2013.01); *A61P 35/00* (2018.01)

(58) Field of Classification Search
CPC .............. A61K 31/435; A61K 31/4745; A61K 2300/00; A61P 35/00; A61P 35/02
See application file for complete search history.

(56) References Cited

U.S. PATENT DOCUMENTS 7,625,926 B2 * 12/2009 Bang ................. A61P 35/00
514/307
2015/0272943 A1 10/2015 Kim et al.

FOREIGN PATENT DOCUMENTS

WO  WO 2005/033097 A1  4/2005
WO  WO 2005/033101 A1  4/2005

OTHER PUBLICATIONS

Fujita et al, 2015, 21(43), 12234-12248.*
Shao et al., 2016, Molecular and Clinical Oncology, 2016, 5, 361-366.*
Irinotecan dosage, 2022, https://reference.medscape.com/drug/camptosar-irinotecan-342252.*
Jimeno A. et al. "3032: A phase I study of the ora; administration of irinotecan in combination with the potent P-glycoprotein (P-gp) inhibitor HM30181A", *Journal of Clinical Oncology; 2019 Annual Meeting of the American Society of Clinical Oncology, ASCO 2019*, vol. 37, No. Supplement 15, 2019, p. 3032.
Kim, T-E. et al. "Tolerability and Pharmacokinetics of a New P-Glycoprotein Inhibitor, HM30181, in Healthy Korean Male Volunteers: Single- and Multiple-Dose Randomized, Placebo-Controlled Studies", *Clinical Therapeutics*, vol. 34, No. 2, 2012, pp. 482-494.

* cited by examiner

*Primary Examiner* — Sun Jae Yoo
(74) *Attorney, Agent, or Firm* — Fish IP Law, LLP

(57) ABSTRACT

The present disclosure provides pharmaceutical combinations of orally administered irinotecan and a P-gp inhibitor. The pharmaceutical combinations are suitable for the treatment of cancer in a subject and for reducing or preventing toxicity, hypersensitivity-type infusion reactions, and other negative outcomes resulting from or associated with intravenously administered irinotecan (e.g., Camptosar®) therapy in a subject suffering from cancer.

16 Claims, 13 Drawing Sheets

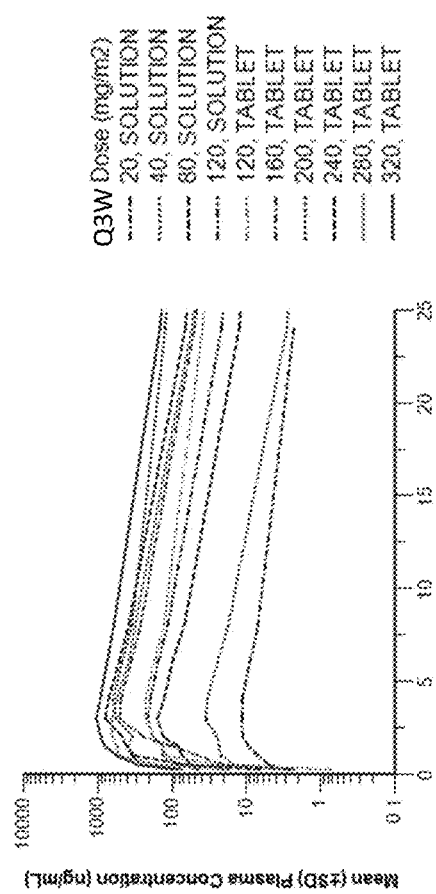

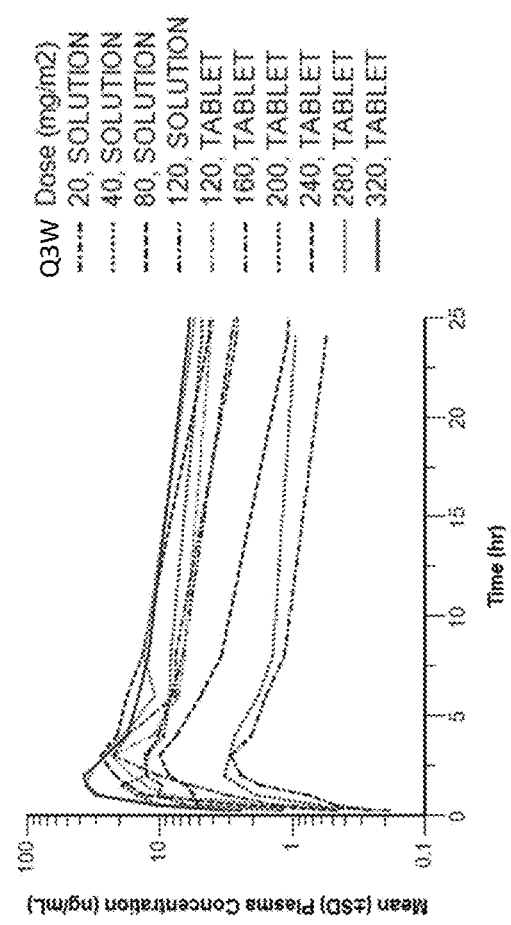

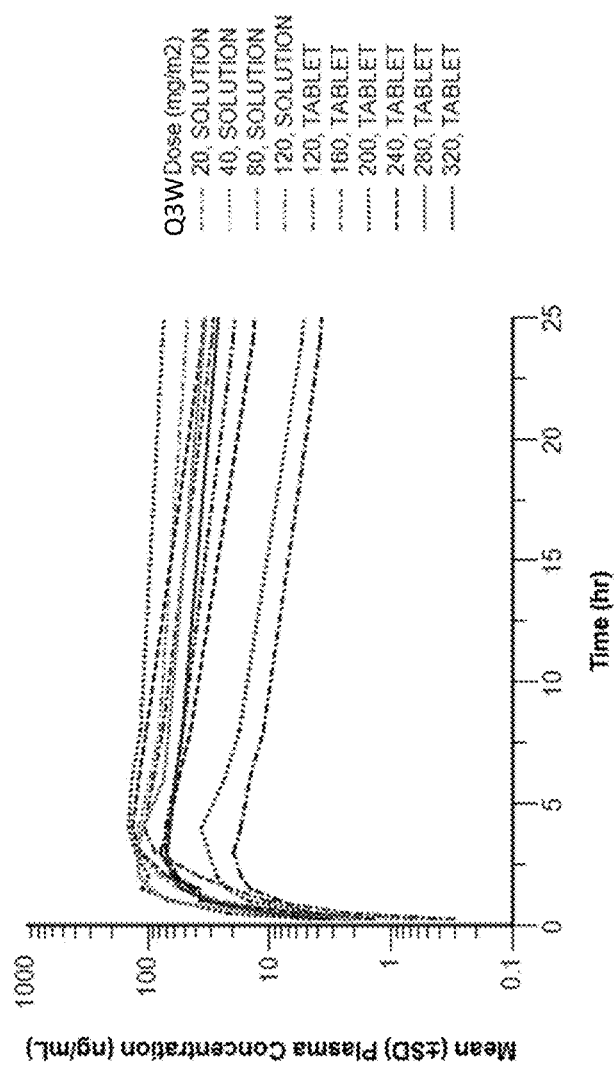

THERAPEUTIC COMBINATIONS OF ORALLY ADMINISTERED IRINOTECAN AND A P-GP INHIBITOR FOR THE TREATMENT OF CANCER

RELATED APPLICATIONS

This application claims priority to, and the benefit of, U.S. Provisional Application Nos. 62/780,110, filed on Dec. 14, 2018, and 62/846,829, filed on May 13, 2019, the contents of each of which are incorporated herein in their entirety.

BACKGROUND

Irinotecan (Camptosar®) was approved for medical use in 1996 and marketed under the brand name Camptosar®. Irinotecan is in the topoisomerase inhibitor family of medication. It works by blocking topoisomerase 1 which results in DNA damage and cell death. Irinotecan is activated by hydrolysis to SN-38, an inhibitor of topoisomerase 1. This is then inactivated by glucuronidation by uridine diphosphate glucuronosyltransferase 1A1 (UGT1A1). The inhibition of topoisomerase 1 by the active metabolite SN-38 eventually leads to inhibition of both DNA replication and transcription. The molecular action of irinotecan occurs by trapping a subset of topoisomerase-1-DNA cleavage complexes, those with a guanine +1 in the DNA sequence. One irinotecan molecule stacks against the base pairs flanking the topoisomerase-induced cleavage site and inactivates the topoisomerase 1 enzyme.

Irinotecan (Camptosar®) is indicated to treat many types of cancer, including colorectal, lung, ovarian, cervical, pancreatic, upper gastrointestinal and brain cancer and is given by slow injection into a vein. Optionally, irinotecan is used either alone or with fluorouracil or cisplatin. Traditionally, the main objective has been dosing schedules that establish the highest dose possible that would lead to disruption of tumor growth, while allowing the bone marrow to recover from the chemotherapy induced toxicity. The potential advantages of oral irinotecan administration include prolonged blood levels, less toxicity, greater convenience, and reduced cost.

Therefore, an effective therapeutic regimen including an oral formulation of irinotecan along with oral administration of a p-glycoprotein pump (P-gp) inhibitor may be beneficial and may be expected to improve the treatment outcomes of cancer. By inhibiting the efflux by P-gp back to the intestinal lumen, oral administration would allow therapeutically relevant concentrations of the drug that are now efficacious, thus leading to a wide therapeutic window that will promote antitumor response while mitigating or avoiding the reactions and toxicities associated directly with the drug or necessitated excipients. In addition, oral administration of irinotecan provides a more convenient and safe method. The present disclosure addresses the needs for orally administering irinotecan.

SUMMARY

In some aspects, the present disclosure provides, at least in part, methods for treating a disease or disorder, such as cancer, or reducing or preventing toxicity, hypersensitivity-type infusion reactions and/or other negative outcomes (e.g., skin toxicity, nausea, vomiting, diarrhea, fatigue, sensory neuropathy, and infection) resulting from or associated with intravenously administered irinotecan (e.g., Camptosar®) therapy in a subject.

In some aspects, the present disclosure provides a compound for use in the treatment of a disease or disorder in a subject in need thereof, wherein the compound is Compound A:

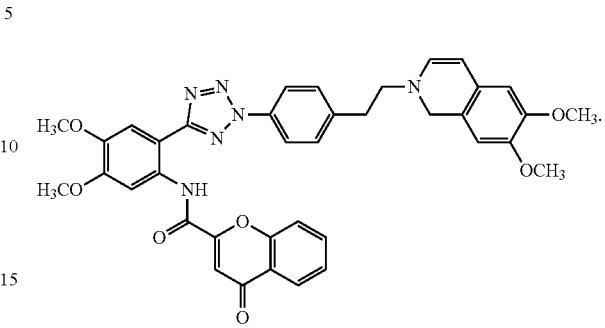

In some aspects, the present disclosure provides Compound A for use in the treatment of cancer in a subject in need thereof.

In some aspects, the present disclosure provides Compound A for use in reducing hematologic toxicity and/or neurotoxicity, and/or other toxicities or symptoms (e.g., skin toxicity, nausea, vomiting, diarrhea, fatigue, sensory neuropathy, and infection) in a subject in need thereof.

In some aspects, the present disclosure provides Compound A for use in reducing or preventing hypersensitivity-type infusion reactions associated with intravenously administered irinotecan (e.g., Camptosar®) therapy in a subject in need thereof.

In some aspects, the present disclosure provides a method for treating a disease or disorder in a subject in need thereof, comprising:
a. oral administration of irinotecan at an amount of about 5 mg/m$^2$ to about 500 mg/m$^2$ to the subject once a day and for 1-7 times a week; and
b. oral administration of Compound A to the subject once a day and for 1-7 times a week, wherein Compound A is administered simultaneously with or prior to the irinotecan.

In some aspects, the present disclosure provides a method for treating cancer in a subject in need thereof, comprising:
a. oral administration of irinotecan at an amount of about 5 mg/m$^2$ to about 500 mg/m$^2$ to the subject once a day and for 1-7 times a week; and
b. oral administration of Compound A to the subject once a day and for 1-7 times a week, wherein Compound A is administered simultaneously with or prior to the irinotecan.

In some aspects, the present disclosure provides a method for reducing hematologic toxicity and/or neurotoxicity, and/or other toxicities or symptoms (e.g., skin toxicity, nausea, vomiting, diarrhea, fatigue, sensory neuropathy, and infection) in a subject in need thereof, comprising:
a. oral administration of irinotecan at an amount of about 5 mg/m$^2$ to about 500 mg/m$^2$ to the subject once a day and for 1-7 times a week; and
b. oral administration of Compound A to the subject once a day and for 1-7 times a week, wherein Compound A is administered simultaneously with or prior to the irinotecan.

In some aspects, the present disclosure provides a method for reducing or preventing hypersensitivity-type infusion reactions associated with intravenously administered irinotecan (e.g., Camptosar®) therapy in a subject in need thereof, comprising:

a. oral administration of irinotecan at an amount of about 5 mg/m² to about 500 mg/m² to the subject once a day and for 1-7 times a week; and b. oral administration of Compound A to the subject once a day and for 1-7 times a week, wherein Compound A is administered simultaneously with or prior to the irinotecan.

In some aspects, the present disclosure provides use of oral irinotecan in combination with Compound A in treating a disease or disorder in a subject in need thereof.

In some aspects, the present disclosure provides use of oral irinotecan in combination with Compound A in treating cancer in a subject in need thereof.

In some aspects, the present disclosure provides use of oral irinotecan in combination with Compound A in reducing hematologic toxicity and/or neurotoxicity, and/or other toxicities or symptoms (e.g., skin toxicity, nausea, vomiting, diarrhea, fatigue, sensory neuropathy, and infection) in a subject in need thereof.

In some aspects, the present disclosure provides use of oral irinotecan in combination with Compound A in reducing or preventing hypersensitivity-type infusion reactions associated with intravenously administered irinotecan (e.g., Camptosar®) therapy in a subject in need thereof.

In some aspects, the present disclosure provides irinotecan for oral administration for use in combination with Compound A in treating a disease or disorder in a subject in need thereof.

In some aspects, the present disclosure provides irinotecan for oral administration for use in combination with Compound A in treating cancer in a subject in need thereof.

In some aspects, the present disclosure provides irinotecan for oral administration for use in combination with Compound A in reducing hematologic toxicity and/or neurotoxicity, and/or other toxicities or symptoms (e.g., skin toxicity, nausea, vomiting, diarrhea, fatigue, sensory neuropathy, and infection) in a subject in need thereof.

In some aspects, the present disclosure provides irinotecan for oral administration for use in combination with Compound A in reducing or preventing hypersensitivity-type infusion reactions associated with intravenously administered irinotecan (e.g., Camptosar®) therapy in a subject in need thereof.

In some aspects, the present disclosure provides the use of irinotecan in combination with Compound A in the manufacture of a medicament for treating a disease or disorder in a subject in need thereof.

In some aspects, the present disclosure provides the use of irinotecan in combination with Compound A in the manufacture of a medicament for treating cancer in a subject in need thereof.

In some aspects, the present disclosure provides the use of irinotecan in combination with Compound A in the manufacture of a medicament for reducing hematologic toxicity and/or neurotoxicity, and/or other toxicities or symptoms (e.g., skin toxicity, nausea, vomiting, diarrhea, fatigue, sensory neuropathy, and infection) in a subject in need thereof.

In some aspects, the present disclosure provides the use of irinotecan in combination with Compound A in the manufacture of a medicament for reducing or preventing hypersensitivity-type infusion reactions associated with intravenously administered irinotecan (e.g., Camptosar®) therapy in a subject in need thereof.

In some aspects, the present disclosure provides the use of irinotecan for oral administration in combination with Compound A in the manufacture of a medicament for treating a disease or disorder in a subject in need thereof.

In some aspects, the present disclosure provides the use of irinotecan for oral administration in combination with Compound A in the manufacture of a medicament for treating cancer in a subject in need thereof.

In some aspects, the present disclosure provides the use of irinotecan for oral administration in combination with Compound A in the manufacture of a medicament for reducing hematologic toxicity and/or neurotoxicity, and/or other toxicities or symptoms (e.g., skin toxicity, nausea, vomiting, diarrhea, fatigue, sensory neuropathy, and infection) in a subject in need thereof.

In some aspects, the present disclosure provides the use of irinotecan for oral administration in combination with Compound A in the manufacture of a medicament for reducing or preventing hypersensitivity-type infusion reactions associated with intravenously administered irinotecan (e.g., Camptosar®) therapy in a subject in need thereof.

In some aspects, the present disclosure provides irinotecan for use with Compound A in a combinational therapy for treating a disease or disorder in a subject in need thereof.

In some aspects, the present disclosure provides irinotecan for use with Compound A in a combinational therapy for treating cancer in a subject in need thereof.

In some aspects, the present disclosure provides irinotecan for use with Compound A in a combinational therapy for reducing hematologic toxicity and/or neurotoxicity, and/or other toxicities or symptoms (e.g., skin toxicity, nausea, vomiting, diarrhea, fatigue, sensory neuropathy, and infection) in a subject in need thereof.

In some aspects, the present disclosure provides irinotecan for use with Compound A in a combinational therapy for reducing or preventing hypersensitivity-type infusion reactions associated with intravenously administered irinotecan (e.g., Camptosar®) therapy in a subject in need thereof.

In some aspects, the present disclosure provides Compound A for use in a combination therapy with irinotecan in the treatment of a disease or disorder in a subject in need thereof.

In some aspects, the present disclosure provides Compound A for use in a combination therapy with irinotecan in the treatment of cancer in a subject in need thereof.

In some aspects, the present disclosure provides Compound A for use in a combination therapy with irinotecan in reducing hematologic toxicity and/or neurotoxicity, and/or other toxicities or symptoms (e.g., skin toxicity, nausea, vomiting, diarrhea, fatigue, sensory neuropathy, and infection) in a subject in need thereof.

In some aspects, the present disclosure provides Compound A for use in a combination therapy with irinotecan in reducing or preventing hypersensitivity-type infusion reactions associated with intravenously administered irinotecan (e.g., Camptosar®) therapy in a subject in need thereof.

In some aspects, the present disclosure provides use of Compound A in the manufacture of a medicament for use in combination with irinotecan in treating a disease or disorder in a subject in need thereof.

In some aspects, the present disclosure provides use of Compound A in the manufacture of a medicament for use in combination with irinotecan in treating cancer in a subject in need thereof.

In some aspects, the present disclosure provides use of Compound A in the manufacture of a medicament for use in combination with irinotecan in reducing hematologic toxicity and/or neurotoxicity, and/or other toxicities or symptoms (e.g., skin toxicity, nausea, vomiting, diarrhea, fatigue, sensory neuropathy, and infection) in a subject in need thereof.

In some aspects, the present disclosure provides use of Compound A in the manufacture of a medicament for use in combination with irinotecan in reducing or preventing hypersensitivity-type infusion reactions associated with intravenously administered irinotecan (e.g., Camptosar®) therapy in a subject in need thereof.

In some aspects, the present disclosure provides a medicament for use in a combination therapy with irinotecan in the treatment of a disease or disorder in a subject in need thereof, wherein the medicament comprises Compound A.

In some aspects, the present disclosure provides a medicament for use in a combination therapy with irinotecan in the treatment of cancer in a subject in need thereof, wherein the medicament comprises Compound A.

In some aspects, the present disclosure provides a medicament for use in a combination therapy with irinotecan for reducing hematologic toxicity and/or neurotoxicity, and/or other toxicities or symptoms (e.g., skin toxicity, nausea, vomiting, diarrhea, fatigue, sensory neuropathy, and infection) in a subject in need thereof, wherein the medicament comprises Compound A.

In some aspects, the present disclosure provides a medicament for use in a combination therapy with irinotecan for reducing or preventing hypersensitivity-type infusion reactions associated with intravenously administered irinotecan (e.g., Camptosar®) therapy in a subject in need thereof, wherein the medicament comprises Compound A.

In some aspects, the present disclosure provides a medicament for use in a combination therapy with Compound A in the treatment of a disease or disorder in a subject in need thereof, wherein the medicament comprises irinotecan.

In some aspects, the present disclosure provides a medicament for use in a combination therapy with Compound A in the treatment of cancer in a subject in need thereof, wherein the medicament comprises irinotecan.

In some aspects, the present disclosure provides a medicament for use in a combination therapy with Compound A for reducing hematologic toxicity and/or neurotoxicity, and/or other toxicities or symptoms (e.g., skin toxicity, nausea, vomiting, diarrhea, fatigue, sensory neuropathy, and infection) in a subject in need thereof, wherein the medicament comprises irinotecan.

In some aspects, the present disclosure provides a medicament for use in a combination therapy with Compound A for reducing or preventing hypersensitivity-type infusion reactions associated with intravenously administered irinotecan (e.g., Camptosar®) therapy in a subject in need thereof, wherein the medicament comprises irinotecan.

In some aspects, the present disclosure provides use of Compound A in a combination therapy with irinotecan in the treatment of a disease or disorder in a subject in need thereof.

In some aspects, the present disclosure provides use of Compound A in a combination therapy with irinotecan in the treatment of cancer in a subject in need thereof.

In some aspects, the present disclosure provides use of Compound A in a combination therapy with irinotecan for reducing hematologic toxicity and/or neurotoxicity, and/or other toxicities or symptoms (e.g., skin toxicity, nausea, vomiting, diarrhea, fatigue, sensory neuropathy, and infection) in a subject in need thereof.

In some aspects, the present disclosure provides use of Compound A in a combination therapy with irinotecan for reducing or preventing hypersensitivity-type infusion reactions associated with intravenously administered irinotecan (e.g., Camptosar®) therapy in a subject in need thereof.

In some aspects, the present disclosure provides a pharmaceutical combination of irinotecan and Compound A.

In some aspects, the methods, compounds (i.e., Compound A or irinotecan) for use, use (i.e., use of Compound A or irinotecan), medicament, manufacture of medicament, medicament for use, combination, or combination therapy, or the like, described herein, comprises administering orally or oral administration of Compound A, according to the dosage and/or dosing regimen described herein (e.g., once a day and for 1-7 times a week).

In some aspects, the methods, compounds (i.e., Compound A or irinotecan) for use, use (i.e., use of Compound A or irinotecan), medicament, manufacture of medicament, medicament for use, combination, or combination therapy, or the like, described herein, comprises administering orally or oral administration of irinotecan, according to the dosage and/or dosing regimen described herein (e.g., at an amount of about 5 mg/m$^2$ to about 500 mg/m$^2$ to the subject once a day and for 1-7 times a week).

In some aspects, the methods, compounds (i.e., Compound A or irinotecan) for use, use (i.e., use of Compound A or irinotecan), medicament, manufacture of medicament, medicament for use, combination, or combination therapy, or the like, described herein, comprises administering orally or oral administration of Compound A, according to the dosage and/or dosing regimen described herein (e.g., once a day and for 1-7 times a week), simultaneously with or prior to, administering orally or oral administration of irinotecan, according to the dosage and/or dosing regimen described herein (e.g., at an amount of about 5 mg/m$^2$ to about 500 mg/m$^2$ to the subject once a day and for 1-7 times a week).

In some aspects, in the methods, compounds (i.e., Compound A or irinotecan) for use, use (i.e., use of Compound A or irinotecan), medicament, manufacture of medicament, medicament for use, combination, or combination therapy, or the like, described herein, the subject is suffering from cancer and undergoing an irinotecan therapy.

In some aspects, in the methods, compounds (i.e., Compound A or irinotecan) for use, use (i.e., use of Compound A or irinotecan), medicament, manufacture of medicament, medicament for use, combination, or combination therapy, or the like, described herein, the plasma exposure of the orally administered irinotecan, as measured by $AUC_{(0 \to \infty)}$, is equal to or greater than the plasma exposure, as measured by $AUC_{(0 \to \infty)}$, of intravenously administered irinotecan (e.g., Camptosar®) at an amount of about 10 mg/m$^2$ to about 400 mg/m$^2$ over a period of about 1 to about 24 hours once every three weeks, once every two weeks, or once every week.

In some aspects, in the methods, compounds (i.e., Compound A or irinotecan) for use, use (i.e., use of Compound A or irinotecan), medicament, manufacture of medicament, medicament for use, combination, or combination therapy, or the like, described herein, the orally administered irinotecan reaches therapeutic blood or plasma levels in the subject.

Unless otherwise defined, all technical and scientific terms used herein have the same meaning as commonly understood by one of ordinary skill in the art to which this disclosure belongs. In the specification, the singular forms also include the plural unless the context clearly dictates otherwise. Although methods and materials similar or equivalent to those described herein can be used in the practice or testing of the present disclosure, suitable methods and materials are described below. All publications, patent applications, patents and other references mentioned herein are incorporated by reference. The references cited herein are not admitted to be prior art to the present disclosure. In the case of conflict, the present specification, including definitions, will control. In addition, the materials, methods, and examples are illustrative only and are not intended to be limiting.

Other features and advantages of the present disclosure will be apparent from the following detailed descriptions and claims.

BRIEF DESCRIPTION OF THE FIGURES

FIG. 1B is a graph showing the mean plasma concentration (ng/mL) versus time (hr) of oral irinotecan across dose ranges for solution (20, 40, 80, and 120 mg/m$^2$) and tablet (120, 160, 200, 240, 280, and 320 mg/m$^2$) of time to 25 hours.

FIG. 2B is a graph showing the mean plasma concentration (ng/mL) versus time (hr) of M1 across dose ranges for solution (20, 40, 80, and 120 mg/m$^2$) and tablet (120, 160, 200, 240, 280, and 320 mg/m$^2$) of time to 25 hours.

FIG. 3B is a graph showing the mean plasma concentration (ng/mL) versus time (hr) of M2 across dose range for solution (20, 40, 80, and 120 mg/m$^2$) and tablet (120, 160, 200, 240, 280, and 320 mg/m$^2$) for time to 25 hours.

DETAILED DESCRIPTION

Figure 1A:
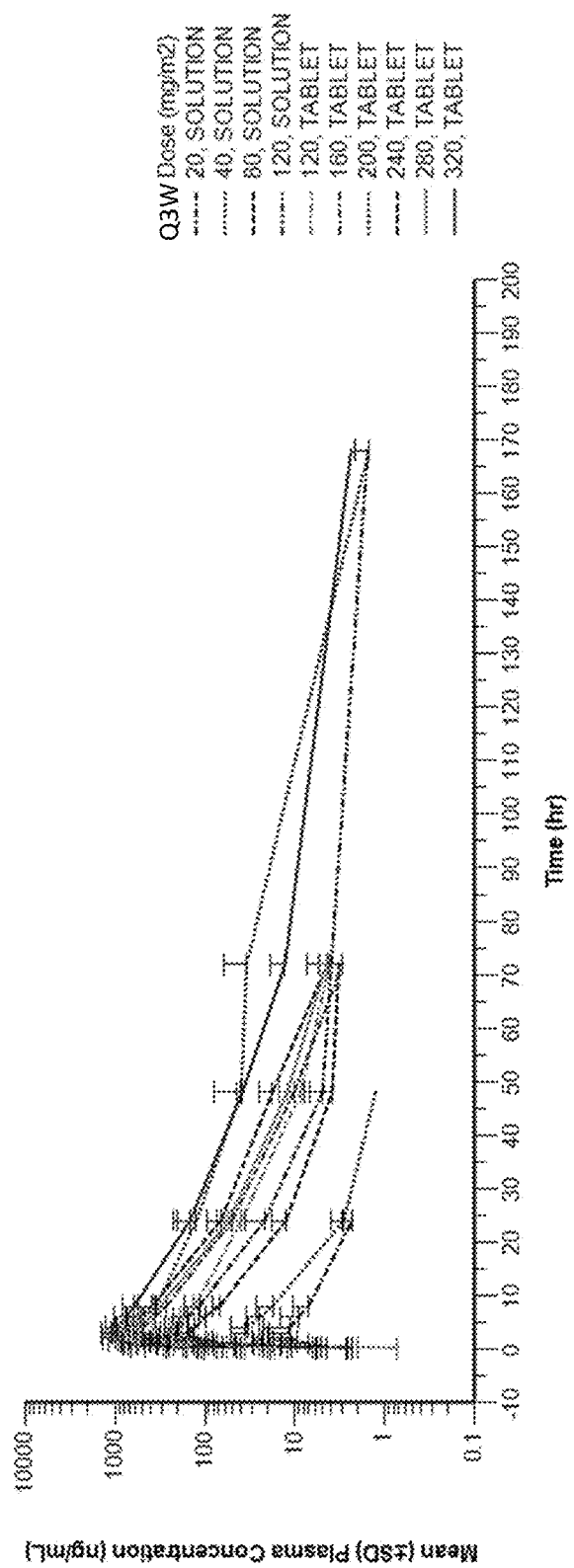
FIG. 1A is a graph showing the mean plasma concentration (ng/mL) versus time (hr) of oral irinotecan across dose ranges for solution (20, 40, 80, and 120 mg/m$^2$) and tablet (120, 160, 200, 240, 280, and 320 mg/m$^2$) of time to 200 hours.

In some aspects, the present disclosure pertains, at least in part, to methods for treating cancer in a subject.

In some aspects, the present disclosure pertains, at least in part, to methods for reducing or preventing toxicity, hypersensitivity-type infusion reactions, and other negative outcomes resulting from or associated with intravenously administered irinotecan (e.g., Camptosar®) therapy in a subject suffering from cancer.

In some embodiments, the present disclosure provides a method for treating cancer in a subject in need thereof, comprising:
  a. oral administration of irinotecan at an amount of about 5 mg/m$^2$ to about 500 mg/m2 to the subject once a day and for 1-7 times a week; and
  b. oral administration of Compound A:

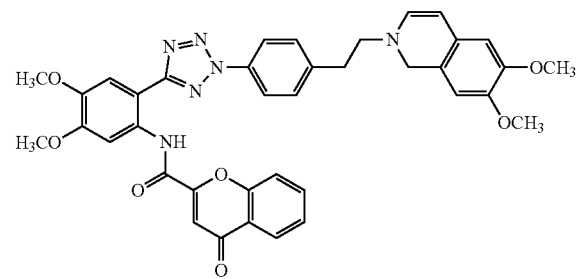 [SMILES: COc1cc2c(cc1OC)CN(CCc1ccc(-n3nnc(-c4cc(OC)c(OC)cc4NC(=O)c4cc(=O)c5ccccc5o4)n3)cc1)C=C2]

to the subject once a day and for 1-7 times a week, wherein Compound A is administered simultaneously with or prior to the irinotecan.

In some embodiments, the present disclosure provides a method for reducing hematologic toxicity and/or neurotoxicity, and/or other toxicities or symptoms (e.g., skin toxicity, nausea, vomiting, diarrhea, fatigue, sensory neuropathy, and infection) in a subject suffering from cancer and undergoing a irinotecan therapy, comprising:
  a. oral administration of irinotecan at an amount of about 5 mg/m$^2$ to about 500 mg/m$^2$ to the subject once a day and for 1-7 times a week; and
  b. oral administration of Compound A to the subject once a day and for 1-7 times a week, wherein the plasma exposure of the orally administered irinotecan, as measured by AUC$_{0\to\infty}$), is equal to or greater than the plasma exposure, as measured by AUC$_{0\to\infty}$), of intravenously administered irinotecan (e.g., Camptosar®) at an amount of about 10 mg/m$^2$ to about 400 mg/m$^2$ over a period of about 1 hour to about 24 hours once every three weeks, once every two weeks, or once every week, and wherein Compound A is administered simultaneously with or prior to the irinotecan.

In some embodiments, the present disclosure provides a method for reducing or preventing hypersensitivity-type infusion reactions associated with intravenously administered irinotecan (e.g., Camptosar®) therapy in a subject in need thereof, comprising:
  a. oral administration of irinotecan at an amount of about 5 mg/m$^2$ to about 500 mg/m$^2$ to the subject once a day and for 1-7 times a week; and b. oral administration of Compound A to the subject once a day and for 1-7 times a week, wherein Compound A is administered simultaneously with or prior to the irinotecan.

In some aspects, the present disclosure pertains, at least in part, to Compound A for use with irinotecan in the treatment of cancer in a subject.

In some aspects, the present disclosure pertains, at least in part, to Compound A for use with irinotecan in reducing or preventing toxicity, hypersensitivity-type infusion reactions, and other negative outcomes resulting from or associated with intravenously administered irinotecan (e.g., Camptosar®) therapy in a subject suffering from cancer.

In some embodiments, the present disclosure provides Compound A for use with irinotecan in the treatment of cancer in a subject in need thereof, wherein the subject is administered irinotecan orally at an amount of about 5 mg/m$^2$ to about 500 mg/m$^2$ once a day and for 1-7 times a week;
wherein Compound A:

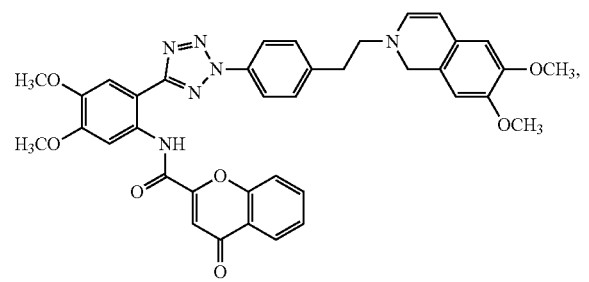 [SMILES: COc1cc2c(cc1OC)CN(CCc1ccc(-n3nnc(-c4cc(OC)c(OC)cc4NC(=O)c4cc(=O)c5ccccc5o4)n3)cc1)C=C2]

is administered to the subject once a day and for 1-7 times a week; and
wherein Compound A is administered simultaneously with or prior to the irinotecan.

In some embodiments, the present disclosure provides Compound A for use with irinotecan in reducing hematologic toxicity and/or neurotoxicity, and/or other toxicities or symptoms (e.g., skin toxicity, nausea, vomiting, diarrhea, fatigue, sensory neuropathy, and infection) in a subject suffering from cancer and undergoing irinotecan therapy, wherein the subject is administered irinotecan orally at an amount of about 5 mg/m$^2$ to about 500 mg/m$^2$ once a day and for 1-7 times a week;
wherein Compound A is administered to the subject once a day and for 1-7 times a week; and
wherein the plasma exposure of the orally administered irinotecan, as measured by $AUC_{(0 \to \infty)}$, is equal to or greater than the plasma exposure, as measured by $AUC_{(0 \to \infty)}$, of intravenously administered irinotecan (e.g., Camptosar®) at an amount of about 10 mg/m$^2$ to about 400 mg/m$^2$ over a period of about 1 to about 24 hours once every three weeks, once every two weeks, or once every week, and wherein Compound A is administered simultaneously with or prior to the irinotecan.

In some embodiments, the present disclosure provides Compound A for use with irinotecan in reducing or preventing hypersensitivity-type infusion reactions associated with intravenously administered irinotecan (e.g., Camptosar®) therapy in a subject in need thereof, wherein the subject is administered irinotecan orally at an amount of about 5 mg/m$^2$ to about 500 mg/m$^2$ once a day and for 1-7 times a week;
wherein Compound A is administered to the subject once a day and for 1-7 times a week; and wherein Compound A is administered simultaneously with or prior to the irinotecan.

In some aspects, the present disclosure pertains, at least in part, to the use of Compound A in the manufacture of a medicament for use with irinotecan in the treatment of cancer in a subject.

In some aspects, the present disclosure pertains, at least in part, to the use of Compound A in the manufacture of a medicament for use with irinotecan in reducing or preventing toxicity, hypersensitivity-type infusion reactions, and other negative outcomes resulting from or associated with intravenously administered irinotecan (e.g., Camptosar®) therapy in a subject suffering from cancer.

In some embodiments, the present disclosure provides the use of Compound A in the manufacture of a medicament for use with irinotecan in treating cancer in a subject in need thereof, wherein the subject is administered irinotecan orally at an amount of about 5 mg/m2 to about 500 mg/m2 once a day and for 1-7 times a week;
wherein Compound A:

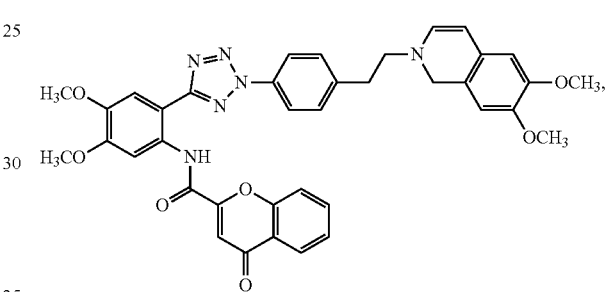

is administered to the subject once a day and for 1-7 times a week; and
wherein Compound A is administered simultaneously with or prior to the irinotecan.

In some embodiments, the present disclosure provides the use of Compound A in the manufacture of a medicament for use with irinotecan in reducing hematologic toxicity and/or neurotoxicity, and/or other toxicities or symptoms (e.g., skin toxicity, nausea, vomiting, diarrhea, fatigue, sensory neuropathy, and infection) in a subject suffering from cancer and undergoing irinotecan therapy, wherein the subject is administered irinotecan orally at an amount of about 5 mg/m$^2$ to about 500 mg/m$^2$ once a day and for 1-7 times a week;
wherein Compound A is administered to the subject once a day and for 1-7 times a week;
and wherein the plasma exposure of the orally administered irinotecan, as measured by $AUC_{0 \to \infty}$), is equal to or greater than the plasma exposure, as measured by $AUC_{0 \to \infty}$), of intravenously administered irinotecan e.g., Camptosar®) at an amount of about 10 mg/m$^2$ to about 400 mg/m$^2$ over a period of about 1 to about 24 hours once every three weeks, once every two weeks, or once every week, and wherein Compound A is administered simultaneously with or prior to the irinotecan.

In some embodiments, the present disclosure provides the use of Compound A in the manufacture of a medicament for use with irinotecan in reducing or preventing hypersensitivity-type infusion reactions associated with intravenously administered irinotecan (e.g., Camptosar®) therapy in a subject in need thereof, wherein the subject is administered irinotecan orally at an amount of about 5 mg/m2 to about 500 mg/m² once a day and for 1-7 times a week;
wherein Compound A is administered to the subject once a day and for 1-7 times a week;
and wherein Compound A is administered simultaneously with or prior to the irinotecan.

In some aspects, the present disclosure pertains, at least in part, to use of Compound A with irinotecan in the treatment of cancer in a subject.

In some aspects, the present disclosure pertains, at least in part, to use of Compound A with irinotecan in reducing or preventing toxicity, hypersensitivity-type infusion reactions, and other negative outcomes resulting from or associated with intravenously administered irinotecan (e.g., Camptosar®) therapy in a subject suffering from cancer.

In some embodiments, the present disclosure provides the use of Compound A with irinotecan in treating cancer in a subject in need thereof, wherein the subject is administered irinotecan orally at an amount of about 5 mg/m² to about 500 mg/m² once a day and for 1-7 times a week; wherein Compound A:

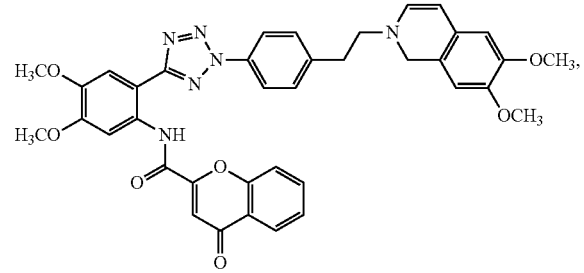 [SMILES: COc1cc2c(cc1OC)CN(CCc1ccc(-n3nnc(-c4cc(OC)c(OC)cc4NC(=O)c4cc(=O)c5ccccc5o4)n3)cc1)C=C2]

is administered to the subject once a day and for 1-7 times a week; and wherein Compound A is administered simultaneously with or prior to the irinotecan.

In some embodiments, the present disclosure provides the use of Compound A with irinotecan in reducing hematologic toxicity and/or neurotoxicity, and/or other toxicities or symptoms (e.g., skin toxicity, nausea, vomiting, diarrhea, fatigue, sensory neuropathy, and infection) in a subject suffering from cancer and undergoing irinotecan therapy, wherein the subject is administered irinotecan orally at an amount of about 5 mg/m² to about 500 mg/m² once a day and for 1-7 times a week, wherein Compound A is administered to the subject once a day and for 1-7 times a week; and wherein the plasma exposure of the orally administered irinotecan, as measured by $AUC_{0\to\infty}$), is equal to or greater than the plasma exposure, as measured by $AUC_{0\to\infty}$, of intravenously administered irinotecan e.g., Camptosar®) at an amount of about 10 mg/m2 to about 400 mg/m² over a period of about 1 to about 24 hours once every three weeks, once every two weeks, or once every week, and
wherein Compound A is administered simultaneously with or prior to the irinotecan.

In some embodiments, the present disclosure provides the use of Compound A with irinotecan in reducing or preventing hypersensitivity-type infusion reactions associated with intravenously administered irinotecan (e.g., Camptosar®) therapy in a subject in need thereof, wherein the subject is administered irinotecan orally at an amount of about 5 mg/m2 to about 500 mg/m² once a day and for 1-7 times a week;
wherein Compound A is administered to the subject once a day and for 1-7 times a week;
and wherein Compound A is administered simultaneously with or prior to the irinotecan.

In some aspects, the present disclosure pertains, at least in part, to Compound A for use in a combination therapy with irinotecan in the treatment of cancer in a subject.

In some aspects, the present disclosure pertains, at least in part, to Compound A for use in a combination therapy with irinotecan in reducing or preventing toxicity, hypersensitivity-type infusion reactions, and other negative outcomes resulting from or associated with intravenously administered irinotecan (e.g., Camptosar®) therapy in a subject suffering from cancer.

In some embodiments, the present disclosure provides Compound A for use in a combination therapy in the treatment of cancer in a subject in need thereof, wherein Compound A:

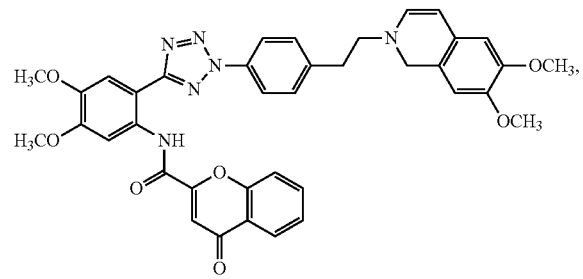 [SMILES: COc1cc2c(cc1OC)CN(CCc1ccc(-n3nnc(-c4cc(OC)c(OC)cc4NC(=O)c4cc(=O)c5ccccc5o4)n3)cc1)C=C2]

is administered to the subject once a day and for 1-7 times a week;
wherein the subject is also administered irinotecan orally at an amount of about 5 mg/m² to about 500 mg/m² once a day and for 1-7 times a week; and
wherein Compound A is administered simultaneously with or prior to the irinotecan.

In some embodiments, the present disclosure provides Compound A for use in a combination therapy for reducing hematologic toxicity and/or neurotoxicity, and/or other toxicities or symptoms (e.g., skin toxicity, nausea, vomiting, diarrhea, fatigue, sensory neuropathy, and infection) in a subject suffering from cancer and undergoing irinotecan therapy, wherein Compound A is administered to the subject once a day and for 1-7 times a week;
wherein the subject is also administered irinotecan orally at an amount of about 5 mg/m² to about 500 mg/m² once a day and for 1-7 times a week;
wherein the plasma exposure of the orally administered irinotecan, as measured by $AUC_{(0\to\infty)}$, is equal to or greater than the plasma exposure, as measured by $AUC_{(0\to\infty)}$, of intravenously administered irinotecan (e.g., Camptosar®) at an amount of about 10 mg/m² to about 400 mg/m² over a period of about 1 to about 24 hours once every three weeks, once every two weeks, or once every week; and
wherein Compound A is administered simultaneously with or prior to the irinotecan.

In some embodiments, the present disclosure provides Compound A for use in a combination therapy with irinotecan for reducing or preventing hypersensitivity-type infusion reactions associated with intravenously administered irinotecan (e.g., Camptosar®) therapy in a subject in need thereof, wherein Compound A is administered to the subject once a day and for 1-7 times a week;

wherein the subject is also administered irinotecan orally at an amount of about 5 mg/m² to about 500 mg/m² once a day and for 1-7 times a week; and
wherein Compound A is administered simultaneously with or prior to the irinotecan.

In some aspects, the present disclosure pertains, at least in part, a medicament comprising Compound A for use in a combination therapy with irinotecan in the treatment of cancer in a subject.

In some aspects, the present disclosure pertains, at least in part, to a medicament comprising Compound A for use in a combination therapy with irinotecan in reducing or preventing toxicity, hypersensitivity-type infusion reactions, and other negative outcomes resulting from or associated with intravenously administered irinotecan (e.g., Camptosar®) therapy in a subject suffering from cancer.

In some embodiments, the present disclosure provides a medicament comprising Compound A:

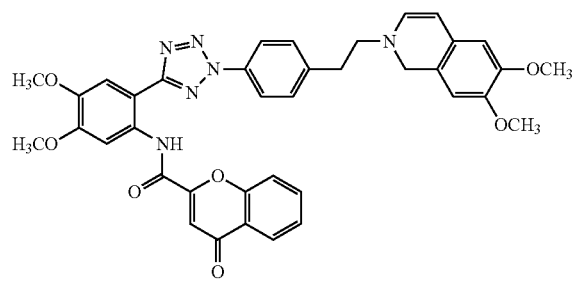 [SMILES: COc1cc2c(cc1OC)CN(CCc1ccc(-n3nnc(-c4cc(OC)c(OC)cc4NC(=O)c4cc(=O)c5ccccc5o4)n3)cc1)C=C2]

with irinotecan in the treatment of cancer in a subject in need thereof, wherein the medicament is administered to the subject once a day and for 1-7 times a week;
wherein the subject is also administered irinotecan orally at an amount of about 5 mg/m² to about 500 mg/m² once a day and for 1-7 times a week; and
wherein the medicament is administered simultaneously with or prior to the irinotecan.

In some embodiments, the present disclosure provides a medicament comprising Compound A for use in a combination therapy with irinotecan for reducing hematologic toxicity and/or neurotoxicity, and/or other toxicities or symptoms (e.g., skin toxicity, nausea, vomiting, diarrhea, fatigue, sensory neuropathy, and infection) in a subject suffering from cancer and undergoing irinotecan therapy, wherein the medicament is administered to the subject once a day and for 1-7 times a week;
wherein the subject is also administered irinotecan orally at an amount of about 5 mg/m² to about 500 mg/m² once a day and for 1-7 times a week;
wherein the plasma exposure of the orally administered irinotecan, as measured by $AUC_{0 \to \infty}$, is equal to or greater than the plasma exposure, as measured by $AUC_{0 \to \infty}$, of intravenously administered irinotecan (e.g., Camptosar®) at an amount of about 10 mg/m² to about 400 mg/m² over a period of about 1 to about 24 hours once every three weeks, once every two weeks, or once every week; and
wherein the medicament is administered simultaneously with or prior to the irinotecan.

In some embodiments, the present disclosure provides a medicament comprising Compound A for use in a combination therapy with irinotecan for reducing or preventing hypersensitivity-type infusion reactions associated with intravenously administered irinotecan (e.g., Camptosar®) therapy in a subject in need thereof wherein the medicament is administered to the subject once a day and for 1-7 times a week;
wherein the subject is also administered irinotecan orally at an amount of about 5 mg/m² to about 500 mg/m² once a day and for 1-7 times a week; and
wherein the medicament is administered simultaneously with or prior to the irinotecan.

In some aspects, the present disclosure pertains, at least in part, to use of Compound A in a combination therapy with irinotecan in the treatment of cancer in a subject.

In some aspects, the present disclosure pertains, at least in part, to use of Compound A in a combination therapy with irinotecan in reducing or preventing toxicity, hypersensitivity-type infusion reactions, and other negative outcomes resulting from or associated with intravenously administered irinotecan (e.g., Camptosar®) therapy in a subject suffering from cancer.

In some embodiments, the present disclosure provides use of Compound A in a combination therapy with irinotecan in the treatment of cancer in a subject in need thereof, wherein Compound A:

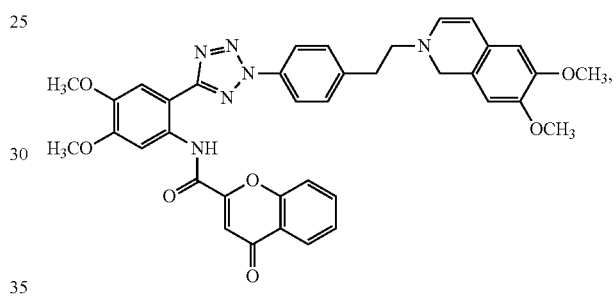

is administered to the subject once a day and for 1-7 times a week;
wherein the subject is also administered irinotecan orally at an amount of about 5 mg/m² to about 500 mg/m² once a day and for 1-7 times a week; and
wherein Compound A is administered simultaneously with or prior to the irinotecan.

In some embodiments, the present disclosure provides use of Compound A in a combination therapy with irinotecan for reducing hematologic toxicity and/or neurotoxicity, and/or other toxicities or symptoms (e.g., skin toxicity, nausea, vomiting, diarrhea, fatigue, sensory neuropathy, and infection) in a subject suffering from cancer and undergoing irinotecan therapy, wherein Compound A, is administered to the subject once a day and for 1-7 times a week; wherein the subject is also administered irinotecan orally at an amount of about 5 mg/m² to about 500 mg/m² once a day and for 1-7 times a week;
wherein the plasma exposure of the orally administered irinotecan, as measured by $AUC_{(0 \to \infty)}$, is equal to or greater than the plasma exposure, as measured by $AUC_{(0 \to \infty)}$, of intravenously administered irinotecan (e.g., Camptosar®) at an amount of about 10 mg/m² to about 400 mg/m² over a period of about 1 to about 24 hours once every three weeks, once every two weeks, or once every week; and
wherein Compound A is administered simultaneously with or prior to the irinotecan.

In some embodiments, the present disclosure provides use of Compound A in a combination therapy with irinotecan for reducing or preventing hypersensitivity-type infusion reactions associated with intravenously administered irinotecan (e.g., Camptosar®) therapy in a subject in need thereof, wherein Compound A, is administered to the subject once a day and for 1-7 times a week;
  wherein the subject is also administered irinotecan orally at an amount of about 5 mg/m² to about 500 mg/m² once a day and for 1-7 times a week;
  wherein the plasma exposure of the orally administered irinotecan, as measured by $AUC_{(0 \to \infty)}$, is equal to or greater than the plasma exposure, as measured by $AUC_{(0 \to \infty)}$, of intravenously administered irinotecan (e.g., Camptosar®) at an amount of about 10 mg/m² to about 400 mg/m² over a period of about 1 to about 24 hours once every three weeks, once every two weeks, or once every week; and
  wherein Compound A is administered simultaneously with or prior to the irinotecan.

In some embodiments, the intravenously administered irinotecan (e.g., Camptosar®) is infused over a period of about 1 hour once every three weeks.

In some embodiments, the intravenously administered irinotecan (e.g., Camptosar®) is infused over a period of about 1.5 hour once every three weeks.

In some embodiments, the intravenously administered irinotecan (e.g., Camptosar®) is infused over a period of about 2 hours once every three weeks.

In some embodiments, the intravenously administered irinotecan (e.g., Camptosar®) is infused over a period of about 3 hours once every three weeks.

In some embodiments, the intravenously administered irinotecan (e.g., Camptosar®) is infused over a period of about 6 hours once every three weeks.

In some embodiments, the intravenously administered irinotecan (e.g., Camptosar®) is infused over a period of about 9 hours once every three weeks.

In some embodiments, the intravenously administered irinotecan (e.g., Camptosar®) is infused over a period of about 12 hours once every three weeks.

In some embodiments, the intravenously administered irinotecan (e.g., Camptosar®) is infused over a period of about 15 hours once every three weeks.

In some embodiments, the intravenously administered irinotecan (e.g., Camptosar®) is infused over a period of about 18 hours once every three weeks.

In some embodiments, the intravenously administered irinotecan (e.g., Camptosar®) is infused over a period of about 21 hours once every three weeks.

In some embodiments, the intravenously administered irinotecan (e.g., Camptosar®) is infused over a period of about 24 hours once every three weeks.

In some embodiments, the intravenously administered irinotecan (e.g., Camptosar®) is infused at about 50 mg/m² to about 400 mg/m² over a period of about 1 hour, about 2 hours, about 3 hours, about 6 hours, about 9 hours, about 12 hours, about 15 hours, about 18 hours, about 21 hours, or about 24 hours once every three weeks. In some embodiments, the intravenously administered irinotecan (e.g., Camptosar®) is infused at about 75 mg/m². In some embodiments, the intravenously administered irinotecan (e.g., Camptosar®) is infused at about 100 mg/m². In some embodiments, the intravenously administered irinotecan (e.g., Camptosar®) is infused at about 125 mg/m². In some embodiments, the intravenously administered irinotecan (e.g., Camptosar®) is infused at about 150 mg/m². In some embodiments, the intravenously administered irinotecan (e.g., Camptosar®) is infused at about 180 mg/m². In some embodiments, the intravenously administered irinotecan (e.g., Camptosar®) is infused at about 210 mg/m². In some embodiments, the intravenously administered irinotecan (e.g., Camptosar®) is infused at about 240 mg/m². In some embodiments, the intravenously administered irinotecan (e.g., Camptosar®) is infused at about 300 mg/m². In some embodiments, the intravenously administered irinotecan (e.g., Camptosar®) is infused at about 350 mg/m².

In some embodiments, the intravenously administered irinotecan (e.g., Camptosar®) is infused over a period of about 1 hour once every two weeks.

In some embodiments, the intravenously administered irinotecan (e.g., Camptosar®) is infused over a period of about 2 hours once every two weeks.

In some embodiments, the intravenously administered irinotecan (e.g., Camptosar®) is infused over a period of about 3 hours once every two weeks.

In some embodiments, the intravenously administered irinotecan (e.g., Camptosar®) is infused over a period of about 6 hours once every two weeks.

In some embodiments, the intravenously administered irinotecan (e.g., Camptosar®) is infused over a period of about 9 hours once every three weeks.

In some embodiments, the intravenously administered irinotecan (e.g., Camptosar® is infused over a period of about 12 hours once every two weeks.

In some embodiments, the intravenously administered irinotecan (e.g., Camptosar®) is infused over a period of about 15 hours once every three weeks.

In some embodiments, the intravenously administered irinotecan (e.g., Camptosar®) is infused over a period of about 18 hours once every two weeks.

In some embodiments, the intravenously administered irinotecan (e.g., Camptosar®) is infused over a period of about 21 hours once every two weeks.

In some embodiments, the intravenously administered irinotecan (e.g., Camptosar®) is infused over a period of about 24 hours once every two weeks.

In some embodiments, the intravenously administered irinotecan (e.g., Camptosar®) is infused at about 50 mg/m² to about 400 mg/m² over a period of about 1 hour, about 2 hours, about 3 hours, about 6 hours, about 9 hours, about 12 hours, about 15 hours, about 18 hours, about 21 hours, or about 24 hours once every two weeks. In some embodiments, the intravenously administered irinotecan (e.g., Camptosar®) is infused at about 50 mg/m². In some embodiments, the intravenously administered irinotecan (e.g., Camptosar®) is infused at about 75 mg/m². In some embodiments, the intravenously administered irinotecan (e.g., Camptosar®) is infused at about 100 mg/m². In some embodiments, the intravenously administered irinotecan (e.g., Camptosar®) is infused at about 125 mg/m². In some embodiments, the intravenously administered irinotecan (e.g., Camptosar®) is infused at about 150 mg/m². In some embodiments, the intravenously administered irinotecan (e.g., Camptosar®) is infused at about 180 mg/m². In some embodiments, the intravenously administered irinotecan (e.g., Camptosar®) is infused at about 210 mg/m².

In some embodiments, the intravenously administered irinotecan (e.g., Camptosar®) is infused over a period of about 1 hour twice every week.

In some embodiments, the intravenously administered irinotecan (e.g., Camptosar®) is infused over a period of about 2 hours twice every week.

In some embodiments, the intravenously administered irinotecan (e.g., Camptosar®) is infused over a period of about 3 hours twice every week.

In some embodiments, the intravenously administered irinotecan (e.g., Camptosar®) is infused over a period of about 6 hours twice every week.
In some embodiments, the intravenously administered irinotecan (e.g., Camptosar®) is infused over a period of about 9 hours twice every week.
In some embodiments, the intravenously administered irinotecan (e.g., Camptosar®) is infused over a period of about 12 hours twice every week.
In some embodiments, the intravenously administered irinotecan (e.g., Camptosar®) is infused over a period of about 15 hours twice every week.
In some embodiments, the intravenously administered irinotecan (e.g., Camptosar®) is infused over a period of about 18 hours twice every week.
In some embodiments, the intravenously administered irinotecan (e.g., Camptosar®) is infused over a period of about 21 hours twice every week.
In some embodiments, the intravenously administered irinotecan (e.g., Camptosar®) is infused over a period of about 24 hours twice every week.
In some embodiments, the intravenously administered irinotecan (e.g., Camptosar®) is infused at about 30 mg/m$^2$ to 200 mg/m$^2$ over a period of about 1 hour, about 2 hours, about 3 hours, about 6 hours, about 9 hours, about 12 hours, about 15 hours, about 18 hours, about 21 hours, or about 24 hours twice every week. In some embodiments, the intravenously administered irinotecan (e.g., Camptosar®) is infused at about 25 mg/m$^2$. In some embodiments, the intravenously administered irinotecan (e.g., Camptosar®) is infused at about 75 mg/m$^2$. In some embodiments, the intravenously administered irinotecan (e.g., Camptosar®) is infused at about 30 mg/m$^2$. In some embodiments, the intravenously administered irinotecan (e.g., Camptosar®) is infused at about 60 mg/m$^2$. In some embodiments, the intravenously administered irinotecan (e.g., Camptosar®) is infused at about 90 mg/m$^2$. In some embodiments, the intravenously administered irinotecan (e.g., Camptosar®) is infused at about 100 mg/m$^2$. In some embodiments, the intravenously administered irinotecan (e.g., Camptosar®) is infused at about 125 mg/m$^2$. In some embodiments, the intravenously administered irinotecan (e.g., Camptosar®) is infused at about 150 mg/m$^2$. In some embodiments, the irinotecan is intravenously administered for a period of three or four weeks.

In some embodiments, the hematologic toxicity associated with the intravenous administration of irinotecan in a subject suffering from cancer includes anemia and/or myelosuppression. In some embodiments, the myelosuppression may be from leukopenia, neutropenia, and thrombocytopenia, or any combination thereof.

In some embodiments, the neurotoxicity associated with the intravenous administration of irinotecan in a subject suffering from cancer includes symptoms such as numbness, tingling, sharp pain, jabbing pain, burning pain, extreme sensitivity, loss of coordination, falling, weakness, paralysis, sweating, heat intolerance, dizziness, changes in blood pressure, bowel problems, and bladder problems, or any combination thereof.

In some embodiments, the present disclosure provides a method for reducing or preventing hypersensitivity-type infusion reactions associated with intravenously administered irinotecan (e.g., Camptosar®) therapy in a subject suffering from cancer, comprising:
a. oral administration of irinotecan at an amount of about 5 mg/m$^2$ to about 500 mg/m$^2$ to the subject once a day and for 1-7 times a week; and b. oral administration of Compound A:

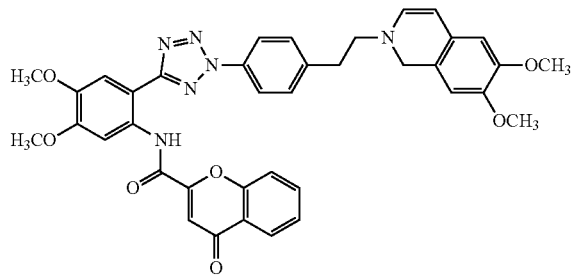 [SMILES: COc1cc2c(cc1OC)CN(CCc1ccc(-n3nnc(-c4cc(OC)c(OC)cc4NC(=O)c4cc(=O)c5ccccc5o4)n3)cc1)C=C2]

to the subject once a day and for 1-7 times a week, wherein the orally administered irinotecan reaches therapeutic blood or plasma levels in the subject, and
wherein Compound A is administered simultaneously with or prior to the irinotecan.

In some embodiments, the present disclosure provides Compound A for use in reducing or preventing hypersensitivity-type infusion reactions associated with intravenously administered irinotecan (e.g., Camptosar®) therapy in a subject suffering from cancer, wherein the subject is administered irinotecan orally at an amount of about 5 mg/m$^2$ to about 500 mg/m$^2$ once a day and for 1-7 times a week; wherein Compound A:

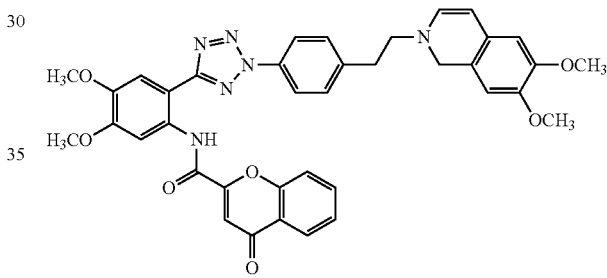

once a day and for 1-7 times a week; and wherein the orally administered irinotecan reaches therapeutic blood or plasma levels in the subject, and wherein Compound A is administered simultaneously with or prior to the irinotecan.

In some embodiments, the present disclosure provides the use of Compound A in the manufacture of a medicament for use with irinotecan in reducing or preventing hypersensitivity-type infusion reactions associated with intravenously administered irinotecan (e.g., Camptosar®) therapy in a subject suffering from cancer, wherein the subject is administered irinotecan orally at an amount of about 5 mg/m$^2$ to about 500 mg/m$^2$ once a day and for 1-7 times a week; wherein Compound A:

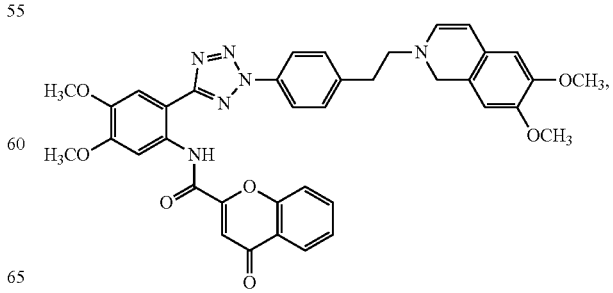

is administered to the subject once a day and for 1-7 times a week; and
wherein the orally administered irinotecan reaches therapeutic blood or plasma levels in the subject, and wherein Compound A is administered simultaneously with or prior to the irinotecan.

In some embodiments, the present disclosure provides the use of Compound A with irinotecan in reducing or preventing hypersensitivity-type infusion reactions associated with intravenously administered irinotecan (e.g., Camptosar®) therapy in a subject suffering from cancer, wherein the subject is administered irinotecan orally at an amount of about 5 mg/m² to about 500 mg/m² once a day and for 1-7 times a week;
wherein Compound A:

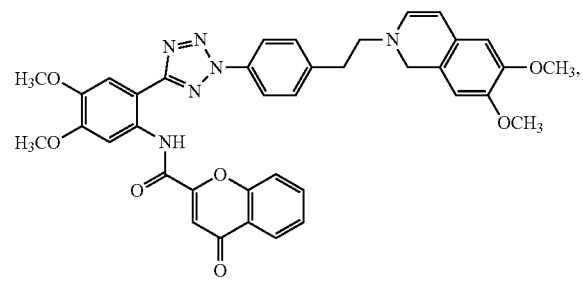 [SMILES: COc1cc2c(cc1OC)CN(CCc1ccc(-n3nnc(-c4cc(OC)c(OC)cc4NC(=O)c4cc(=O)c5ccccc5o4)n3)cc1)C=C2]

is administered to the subject once a
day and for 1-7 times a week; and wherein the orally administered irinotecan reaches therapeutic blood or plasma levels in
the subject, and wherein Compound A is administered simultaneously with or prior to the irinotecan.

In some embodiments, the present disclosure provides Compound A for use in a combination therapy with irinotecan for reducing or preventing hypersensitivity-type infusion reactions associated with intravenously administered irinotecan (e.g., Camptosar®) therapy in a subject suffering from cancer wherein Compound A:

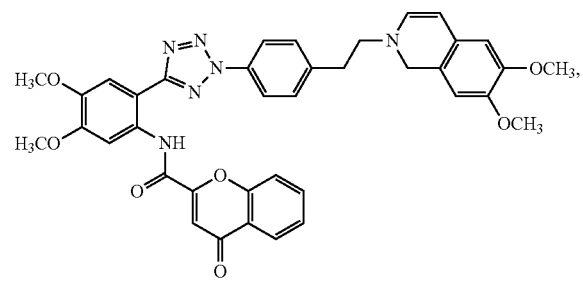 [SMILES: COc1cc2c(cc1OC)CN(CCc1ccc(-n3nnc(-c4cc(OC)c(OC)cc4NC(=O)c4cc(=O)c5ccccc5o4)n3)cc1)C=C2]

is administered to the subject once a day and for 1-7 times a week; and
wherein the subject is also administered irinotecan orally at an amount of about 5 mg/m² to about 500 mg/m² once a day and for 1-7 times a week; and wherein the orally administered irinotecan reaches therapeutic blood or plasma levels in the subject, and
wherein Compound A is administered simultaneously with or prior to the irinotecan.

In some embodiments, the present disclosure provides a medicament for use in a combination therapy with irinotecan for reducing or preventing hypersensitivity-type infusion reactions associated with intravenously administered irinotecan (e.g., Camptosar®) therapy in a subject suffering from cancer, wherein the medicament comprises Compound A:

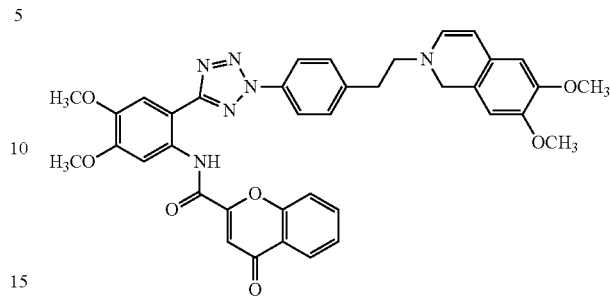

once a day and for 1-7 times a week; and wherein the subject is also administered irinotecan orally at an amount of about 5 mg/m² to about 500 mg/m² once a day and for 1-7 times a week; and wherein the orally administered irinotecan reaches therapeutic blood or plasma levels in the subject, and wherein the medicament is administered simultaneously with or prior to the irinotecan.

In some embodiments, the present disclosure provides use of Compound A in a combination therapy with irinotecan for reducing or preventing hypersensitivity-type infusion reactions associated with intravenously administered irinotecan (e.g., Camptosar®) therapy in a subject suffering from cancer, wherein Compound A:

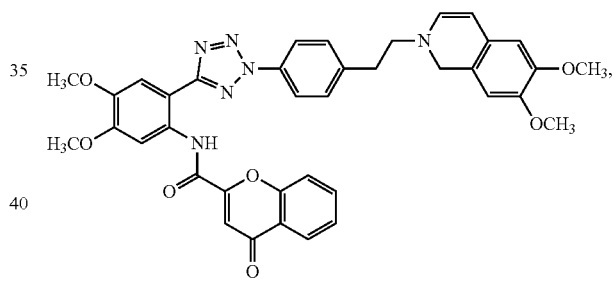

is administered to the subject once a day and for 1-7 times a week; and
wherein the subject is also administered irinotecan orally at an amount of about 5 mg/m² to about 500 mg/m² once a day and for 1-7 times a week; and wherein the orally administered irinotecan reaches therapeutic blood or plasma levels in the subject, and
wherein Compound A is administered simultaneously with or prior to the irinotecan.

In some embodiments, the hypersensitivity-type infusion reactions associated with the intravenous administration of irinotecan in a subject suffering from cancer includes any sign or symptom on the first day of intravenous administration of irinotecan. In some embodiments, the signs or symptoms in the subject include fever, rash, hives, pruritus, flushing, swelling, dyspnea, bronchospasm, stridor, reduced pulmonary expiratory flow, hypoxia, hypertension, hypotension, hypotonia, syncope, falling, incontinence, abdominal pain, vomiting, urticaria, facial swelling, eye disorders, headache, arrhythmia, tachycardia, nausea, chest pain, and/or anaphylaxis, or any combination thereof.

In some embodiments, the irinotecan is administered orally.

In some embodiments, the irinotecan is administered at an amount of about 5 mg/m$^2$ to about 500 mg/m$^2$.

In some embodiments, the irinotecan is administered at an amount of about 5 mg/m$^2$ to about 450 mg/m$^2$.

In some embodiments, the irinotecan is administered at an amount of about 10 mg/m$^2$ to about 500 mg/m$^2$.

In some embodiments, the irinotecan is administered at an amount of about 15 mg/m$^2$ to about 500 mg/m$^2$.

In some embodiments, the irinotecan is administered at an amount of about 15 mg/m$^2$ to about 450 mg/m$^2$.

In some embodiments, the irinotecan is administered at an amount of about 15 mg/m$^2$ to about 400 mg/m$^2$.

In some embodiments, the irinotecan is administered at an amount of about 20 mg/m$^2$ to about 350 mg/m$^2$.

In some embodiments, the irinotecan is administered at an amount of about 25 mg/m$^2$ to about 350 mg/m$^2$.

In some embodiments, the irinotecan is administered at an amount of about 30 mg/m$^2$ to about 350 mg/m$^2$.

In some embodiments, the irinotecan is administered at an amount of about 35 mg/m$^2$ to about 350 mg/m$^2$.

In some embodiments, the irinotecan is administered at an amount of about 40 mg/m$^2$ to about 350 mg/m$^2$.

In some embodiments, the irinotecan is administered at an amount of about 45 mg/m$^2$ to about 350 mg/m$^2$.

In some embodiments, the irinotecan is administered at an amount of about 50 mg/m$^2$ to about 350 mg/m$^2$.

In some embodiments, the irinotecan is administered at an amount of about 55 mg/m$^2$ to about 350 mg/m$^2$.

In some embodiments, the irinotecan is administered at an amount of about 60 mg/m$^2$ to about 350 mg/m$^2$.

In some embodiments, the irinotecan is administered at an amount of about 65 mg/m$^2$ to about 350 mg/m$^2$.

In some embodiments, the irinotecan is administered at an amount of about 70 mg/m$^2$ to about 350 mg/m$^2$.

In some embodiments, the irinotecan is administered at an amount of about 75 mg/m$^2$ to about 350 mg/m$^2$.

In some embodiments, the irinotecan is administered at an amount of about 75 mg/m$^2$ to about 325 mg/m$^2$.

In some embodiments, the irinotecan is administered at an amount of about 75 mg/m$^2$ to about 300 mg/m$^2$.

In some embodiments, the irinotecan is administered at an amount of about 75 mg/m$^2$ to about 275 mg/m$^2$.

In some embodiments, the irinotecan is administered at an amount of about 75 mg/m$^2$ to about 250 mg/m$^2$.

In some embodiments, the irinotecan is administered at an amount of about 75 mg/m$^2$ to about 225 mg/m$^2$.

In some embodiments, the irinotecan is administered at an amount of about 80 mg/m$^2$ to about 350 mg/m$^2$.

In some embodiments, the irinotecan is administered at an amount of about 80 mg/m$^2$ to about 325 mg/m$^2$.

In some embodiments, the irinotecan is administered at an amount of about 80 mg/m$^2$ to about 300 mg/m$^2$.

In some embodiments, the irinotecan is administered at an amount of about 80 mg/m$^2$ to about 275 mg/m$^2$.

In some embodiments, the irinotecan is administered at an amount of about 80 mg/m$^2$ to about 250 mg/m$^2$.

In some embodiments, the irinotecan is administered at an amount of about 80 mg/m$^2$ to about 225 mg/m$^2$.

In some embodiments, the irinotecan is administered at an amount of about 85 mg/m$^2$ to about 350 mg/m$^2$.

In some embodiments, the irinotecan is administered at an amount of about 85 mg/m$^2$ to about 325 mg/m$^2$.

In some embodiments, the irinotecan is administered at an amount of about 85 mg/m$^2$ to about 300 mg/m$^2$.

In some embodiments, the irinotecan is administered at an amount of about 85 mg/m$^2$ to about 275 mg/m$^2$.

In some embodiments, the irinotecan is administered at an amount of about 85 mg/m$^2$ to about 250 mg/m$^2$.

In some embodiments, the irinotecan is administered at an amount of about 85 mg/m$^2$ to about 225 mg/m$^2$.

In some embodiments, the irinotecan is administered at an amount of about 90 mg/m$^2$ to about 350 mg/m$^2$.

In some embodiments, the irinotecan is administered at an amount of about 90 mg/m$^2$ to about 325 mg/m$^2$.

In some embodiments, the irinotecan is administered at an amount of about 90 mg/m$^2$ to about 300 mg/m$^2$.

In some embodiments, the irinotecan is administered at an amount of about 90 mg/m$^2$ to about 275 mg/m$^2$.

In some embodiments, the irinotecan is administered at an amount of about 90 mg/m$^2$ to about 250 mg/m$^2$.

In some embodiments, the irinotecan is administered at an amount of about 90 mg/m$^2$ to about 225 mg/m$^2$.

In some embodiments, the irinotecan is administered at an amount of about 95 mg/m$^2$ to about 350 mg/m$^2$.

In some embodiments, the irinotecan is administered at an amount of about 95 mg/m$^2$ to about 325 mg/m$^2$.

In some embodiments, the irinotecan is administered at an amount of about 95 mg/m$^2$ to about 300 mg/m$^2$.

In some embodiments, the irinotecan is administered at an amount of about 95 mg/m$^2$ to about 275 mg/m$^2$.

In some embodiments, the irinotecan is administered at an amount of about 95 mg/m$^2$ to about 250 mg/m$^2$.

In some embodiments, the irinotecan is administered at an amount of about 95 mg/m$^2$ to about 225 mg/m$^2$.

In some embodiments, the irinotecan is administered at an amount of about 100 mg/m$^2$ to about 350 mg/m$^2$.

In some embodiments, the irinotecan is administered at an amount of about 100 mg/m$^2$ to about 325 mg/m$^2$.

In some embodiments, the irinotecan is administered at an amount of about 100 mg/m$^2$ to about 300 mg/m$^2$.

In some embodiments, the irinotecan is administered at an amount of about 100 mg/m$^2$ to about 275 mg/m$^2$.

In some embodiments, the irinotecan is administered at an amount of about 100 mg/m$^2$ to about 250 mg/m$^2$.

In some embodiments, the irinotecan is administered at an amount of about 100 mg/m$^2$ to about 225 mg/m$^2$.

In some embodiments, the irinotecan is administered at an amount of about 105 mg/m$^2$ to about 350 mg/m$^2$.

In some embodiments, the irinotecan is administered at an amount of about 105 mg/m$^2$ to about 325 mg/m$^2$.

In some embodiments, the irinotecan is administered at an amount of about 105 mg/m$^2$ to about 300 mg/m$^2$.

In some embodiments, the irinotecan is administered at an amount of about 105 mg/m$^2$ to about 275 mg/m$^2$.

In some embodiments, the irinotecan is administered at an amount of about 105 mg/m$^2$ to about 250 mg/m$^2$.

In some embodiments, the irinotecan is administered at an amount of about 105 mg/m$^2$ to about 225 mg/m$^2$.

In some embodiments, the irinotecan is administered at an amount of about 110 mg/m$^2$ to about 350 mg/m$^2$.

In some embodiments, the irinotecan is administered at an amount of about 110 mg/m$^2$ to about 325 mg/m$^2$.

In some embodiments, the irinotecan is administered at an amount of about 110 mg/m$^2$ to about 300 mg/m$^2$.

In some embodiments, the irinotecan is administered at an amount of about 110 mg/m$^2$ to about 275 mg/m$^2$.

In some embodiments, the irinotecan is administered at an amount of about 110 mg/m$^2$ to about 250 mg/m$^2$.

In some embodiments, the irinotecan is administered at an amount of about 110 mg/m$^2$ to about 225 mg/m$^2$.

In some embodiments, the irinotecan is administered at an amount of about 115 mg/m$^2$ to about 350 mg/m$^2$.

In some embodiments, the irinotecan is administered at an amount of about 115 mg/m² to about 325 mg/m².

In some embodiments, the irinotecan is administered at an amount of about 115 mg/m² to about 300 mg/m².

In some embodiments, the irinotecan is administered at an amount of about 115 mg/m² to about 275 mg/m².

In some embodiments, the irinotecan is administered at an amount of about 115 mg/m² to about 250 mg/m².

In some embodiments, the irinotecan is administered at an amount of about 115 mg/m² to about 225 mg/m².

In some embodiments, the irinotecan is administered at an amount of about 120 mg/m² to about 350 mg/m².

In some embodiments, the irinotecan is administered at an amount of about 120 mg/m² to about 325 mg/m².

In some embodiments, the irinotecan is administered at an amount of about 120 mg/m² to about 300 mg/m².

In some embodiments, the irinotecan is administered at an amount of about 120 mg/m² to about 275 mg/m².

In some embodiments, the irinotecan is administered at an amount of about 120 mg/m² to about 250 mg/m².

In some embodiments, the irinotecan is administered at an amount of about 120 mg/m² to about 225 mg/m².

In some embodiments, the irinotecan is administered at an amount of about 125 mg/m² to about 350 mg/m².

In some embodiments, the irinotecan is administered at an amount of about 125 mg/m² to about 325 mg/m².

In some embodiments, the irinotecan is administered at an amount of about 125 mg/m² to about 300 mg/m².

In some embodiments, the irinotecan is administered at an amount of about 125 mg/m² to about 275 mg/m².

In some embodiments, the irinotecan is administered at an amount of about 125 mg/m² to about 250 mg/m².

In some embodiments, the irinotecan is administered at an amount of about 125 mg/m² to about 225 mg/m².

In some embodiments, the irinotecan is administered at an amount of about 130 mg/m² to about 350 mg/m².

In some embodiments, the irinotecan is administered at an amount of about 130 mg/m² to about 325 mg/m².

In some embodiments, the irinotecan is administered at an amount of about 130 mg/m² to about 300 mg/m².

In some embodiments, the irinotecan is administered at an amount of about 130 mg/m² to about 275 mg/m².

In some embodiments, the irinotecan is administered at an amount of about 130 mg/m² to about 250 mg/m².

In some embodiments, the irinotecan is administered at an amount of about 130 mg/m² to about 225 mg/m².

In some embodiments, the irinotecan is administered at an amount of about 135 mg/m² to about 350 mg/m².

In some embodiments, the irinotecan is administered at an amount of about 135 mg/m² to about 325 mg/m².

In some embodiments, the irinotecan is administered at an amount of about 135 mg/m² to about 300 mg/m².

In some embodiments, the irinotecan is administered at an amount of about 135 mg/m² to about 275 mg/m².

In some embodiments, the irinotecan is administered at an amount of about 135 mg/m² to about 250 mg/m².

In some embodiments, the irinotecan is administered at an amount of about 135 mg/m² to about 225 mg/m².

In some embodiments, the irinotecan is administered at an amount of about 140 mg/m² to about 350 mg/m².

In some embodiments, the irinotecan is administered at an amount of about 140 mg/m² to about 325 mg/m².

In some embodiments, the irinotecan is administered at an amount of about 140 mg/m² to about 300 mg/m².

In some embodiments, the irinotecan is administered at an amount of about 140 mg/m² to about 275 mg/m².

In some embodiments, the irinotecan is administered at an amount of about 140 mg/m² to about 250 mg/m².

In some embodiments, the irinotecan is administered at an amount of about 140 mg/m² to about 225 mg/m².

In some embodiments, the irinotecan is administered at an amount of about 145 mg/m² to about 350 mg/m².

In some embodiments, the irinotecan is administered at an amount of about 145 mg/m² to about 325 mg/m².

In some embodiments, the irinotecan is administered at an amount of about 145 mg/m² to about 300 mg/m².

In some embodiments, the irinotecan is administered at an amount of about 145 mg/m² to about 275 mg/m².

In some embodiments, the irinotecan is administered at an amount of about 145 mg/m² to about 250 mg/m².

In some embodiments, the irinotecan is administered at an amount of about 145 mg/m² to about 225 mg/m².

In some embodiments, the irinotecan is administered at an amount of about 150 mg/m² to about 350 mg/m².

In some embodiments, the irinotecan is administered at an amount of about 150 mg/m² to about 325 mg/m².

In some embodiments, the irinotecan is administered at an amount of about 150 mg/m² to about 300 mg/m².

In some embodiments, the irinotecan is administered at an amount of about 150 mg/m² to about 275 mg/m².

In some embodiments, the irinotecan is administered at an amount of about 150 mg/m² to about 250 mg/m².

In some embodiments, the irinotecan is administered at an amount of about 150 mg/m² to about 225 mg/m².

In some embodiments, the irinotecan is administered at an amount of about 200 mg/m² to about 300 mg/m².

In some embodiments, the irinotecan is administered at an amount of about 225 mg/m² to about 300 mg/m².

In some embodiments, the irinotecan is administered at an amount of about 250 mg/m² to about 350 mg/m².

In some embodiments, the irinotecan is administered at an amount of about 5 mg/m².

In some embodiments, the irinotecan is administered at an amount of about 10 mg/m².

In some embodiments, the irinotecan is administered at an amount of about 15 mg/m².

In some embodiments, the irinotecan is administered at an amount of about 20 mg/m².

In some embodiments, the irinotecan is administered at an amount of about 25 mg/m².

In some embodiments, the irinotecan is administered at an amount of about 30 mg/m².

In some embodiments, the irinotecan is administered at an amount of about 35 mg/m².

In some embodiments, the irinotecan is administered at an amount of about 40 mg/m².

In some embodiments, the irinotecan is administered at an amount of about 45 mg/m².

In some embodiments, the irinotecan is administered at an amount of about 50 mg/m².

In some embodiments, the irinotecan is administered at an amount of about 55 mg/m².

In some embodiments, the irinotecan is administered at an amount of about 60 mg/m².

In some embodiments, the irinotecan is administered at an amount of about 65 mg/m².

In some embodiments, the irinotecan is administered at an amount of about 70 mg/m².

In some embodiments, the irinotecan is administered at an amount of about 75 mg/m².

In some embodiments, the irinotecan is administered at an amount of about 80 mg/m².

In some embodiments, the irinotecan is administered at an amount of about 85 mg/m².

In some embodiments, the irinotecan is administered at an amount of about 90 mg/m².

In some embodiments, the irinotecan is administered at an amount of about 95 mg/m².

In some embodiments, the irinotecan is administered at an amount of about 100 mg/m².

In some embodiments, the irinotecan is administered at an amount of about 105 mg/m².

In some embodiments, the irinotecan is administered at an amount of about 110 mg/m².

In some embodiments, the irinotecan is administered at an amount of about 115 mg/m².

In some embodiments, the irinotecan is administered at an amount of about 120 mg/m².

In some embodiments, the irinotecan is administered at an amount of about 125 mg/m².

In some embodiments, the irinotecan is administered at an amount of about 130 mg/m².

In some embodiments, the irinotecan is administered at an amount of about 135 mg/m².

In some embodiments, the irinotecan is administered at an amount of about 140 mg/m².

In some embodiments, the irinotecan is administered at an amount of about 145 mg/m².

In some embodiments, the irinotecan is administered at an amount of about 150 mg/m².

In some embodiments, the irinotecan is administered at an amount of about 155 mg/m².

In some embodiments, the irinotecan is administered at an amount of about 160 mg/m².

In some embodiments, the irinotecan is administered at an amount of about 165 mg/m².

In some embodiments, the irinotecan is administered at an amount of about 170 mg/m².

In some embodiments, the irinotecan is administered at an amount of about 175 mg/m².

In some embodiments, the irinotecan is administered at an amount of about 180 mg/m².

In some embodiments, the irinotecan is administered at an amount of about 185 mg/m².

In some embodiments, the irinotecan is administered at an amount of about 190 mg/m².

In some embodiments, the irinotecan is administered at an amount of about 195 mg/m².

In some embodiments, the irinotecan is administered at an amount of about 200 mg/m².

In some embodiments, the irinotecan is administered at an amount of about 205 mg/m².

In some embodiments, the irinotecan is administered at an amount of about 210 mg/m².

In some embodiments, the irinotecan is administered at an amount of about 215 mg/m².

In some embodiments, the irinotecan is administered at an amount of about 220 mg/m².

In some embodiments, the irinotecan is administered at an amount of about 225 mg/m².

In some embodiments, the irinotecan is administered at an amount of about 230 mg/m².

In some embodiments, the irinotecan is administered at an amount of about 235 mg/m².

In some embodiments, the irinotecan is administered at an amount of about 240 mg/m².

In some embodiments, the irinotecan is administered at an amount of about 245 mg/m².

In some embodiments, the irinotecan is administered at an amount of about 250 mg/m².

In some embodiments, the irinotecan is administered at an amount of about 255 mg/m².

In some embodiments, the irinotecan is administered at an amount of about 260 mg/m².

In some embodiments, the irinotecan is administered at an amount of about 265 mg/m².

In some embodiments, the irinotecan is administered at an amount of about 270 mg/m².

In some embodiments, the irinotecan is administered at an amount of about 275 mg/m².

In some embodiments, the irinotecan is administered at an amount of about 280 mg/m².

In some embodiments, the irinotecan is administered at an amount of about 285 mg/m².

In some embodiments, the irinotecan is administered at an amount of about 290 mg/m².

In some embodiments, the irinotecan is administered at an amount of about 295 mg/m².

In some embodiments, the irinotecan is administered at an amount of about 300 mg/m².

In some embodiments, the irinotecan is administered at an amount of about 310 mg/m².

In some embodiments, the irinotecan is administered at an amount of about 315 mg/m².

In some embodiments, the irinotecan is administered at an amount of about 320 mg/m².

In some embodiments, the irinotecan is administered at an amount of about 325 mg/m².

In some embodiments, the irinotecan is administered at an amount of about 350 mg/m².

In some embodiments, the irinotecan is administered at an amount of about 375 mg/m².

In some embodiments, the irinotecan is administered at an amount of about 400 mg/m².

In some embodiments, the irinotecan is administered at an amount of about 425 mg/m².

In some embodiments, the irinotecan is administered at an amount of about 450 mg/m².

In some embodiments, the irinotecan is administered at an amount of about 475 mg/m².

In some embodiments, the irinotecan is administered at an amount of about 500 mg/m².

In some embodiments, the irinotecan is administered as a single dose on a single day.

In some embodiments, the irinotecan is administered on consecutive days.

In some embodiments, the irinotecan is administered 1-7 times per week. In some embodiments, the irinotecan is administered 1-6 times per week. In some embodiments, the irinotecan is administered 1-5 times per week. In some embodiments, the irinotecan is administered 1-4 times per week. In some embodiments, the irinotecan is administered 1-3 times per week. In some embodiments, the irinotecan is administered 1-2 times per week.

In some embodiments, the irinotecan is administered 2-6 times per week. In some embodiments, the irinotecan is administered 2-5 times per week. In some embodiments, the irinotecan is administered 2-4 times per week. In some embodiments, the irinotecan is administered 2-3 times per week.

In some embodiments, the irinotecan is administered 3-6 times per week. In some embodiments, the irinotecan is administered 3-5 times per week. In some embodiments, the irinotecan is administered 3-4 times per week.

In some embodiments, the irinotecan is administered 4-6 times per week. In some embodiments, the irinotecan is administered 4-5 times per week.

In some embodiments, the irinotecan is administered 5-6 times per week. In some embodiments, the irinotecan is administered less than five times per week.

In some embodiments, the irinotecan is administered once per week. In some embodiments, the irinotecan is administered twice per week. In some embodiments, the irinotecan is administered three times per week. In some embodiments, the irinotecan is administered four times per week. In some embodiments, the irinotecan is administered five times per week. In some embodiments, the irinotecan is administered six times per week.

In some embodiments, the irinotecan is administered at a single dose twice per week. In some embodiments, the irinotecan is administered at a single dose three times per week. In some embodiments, the irinotecan is administered at a single dose four times per week. In some embodiments, the irinotecan is administered at a single dose five times per week. In some embodiments, the irinotecan is administered at a single dose six times per week.

In some embodiments, the irinotecan is administered at least once per week. In some embodiments, the irinotecan is administered at least once per week at an amount of any dosage as described above. In some embodiments, the irinotecan is administered once over a three-week period. In some embodiments, the irinotecan is administered once over a three-week period as a tablet. In some embodiments, the irinotecan is administered once over a three-week period as a capsule. In some embodiments, the irinotecan is administered once over a three-week period as an oral solution. In some embodiments, the irinotecan is administered once over a three-week period as a single dose.

In some embodiments, the irinotecan is administered at least once per week at an amount of about 10 mg/m$^2$, about 15 mg/m$^2$, about 20 mg/m$^2$, about 25 mg/m$^2$, about 30 mg/m$^2$, about 35 mg/m$^2$, about 40 mg/m$^2$, about 45 mg/m$^2$, about 50 mg/m$^2$, about 55 mg/m$^2$, about 60 mg/m$^2$, about 65 mg/m$^2$, about 70 mg/m$^2$, about 75 mg/m$^2$, about 80 mg/m$^2$, about 85 mg/m$^2$, about 90 mg/m$^2$, about 95 mg/m$^2$, or about 100 mg/m$^2$. In some embodiments, the irinotecan is administered at least once per week at an amount of about 105 mg/m$^2$, about 110 mg/m$^2$, about 115 mg/m$^2$, about 120 mg/m$^2$, about 125 mg/m$^2$, about 130 mg/m$^2$, about 135 mg/m$^2$, about 140 mg/m$^2$, about 145 mg/m$^2$, or about 150 mg/m$^2$.

In some embodiments, the irinotecan is administered at least once per week at an amount of about 100 mg/m$^2$, about 105 mg/m$^2$, about 110 mg/m$^2$, about 115 mg/m$^2$, about 120 mg/m$^2$, about 125 mg/m$^2$, about 130 mg/m$^2$, about 135 mg/m$^2$, about 140 mg/m$^2$, about 145 mg/m$^2$, about 150 mg/m$^2$, about 155 mg/m$^2$, about 160 mg/m$^2$, about 165 mg/m$^2$, about 170 mg/m$^2$, about 175 mg/m$^2$, about 180 mg/m$^2$, about 185 mg/m$^2$, about 190 mg/m$^2$, about 195 mg/m$^2$, about 200 mg/m$^2$, about 205 mg/m$^2$, about 210 mg/m$^2$, about 215 mg/m$^2$, about 220 mg/m$^2$, about 225 mg/m$^2$, about 230 mg/m$^2$, about 235 mg/m$^2$, about 240 mg/m$^2$, about 245 mg/m$^2$, about 250 mg/m$^2$, about 255 mg/m$^2$, about 260 mg/m$^2$, about 265 mg/m$^2$, about 270 mg/m$^2$, about 275 mg/m$^2$, about 280 mg/m$^2$, about 285 mg/m$^2$, about 290 mg/m$^2$, about 295 mg/m$^2$, about 300 mg/m$^2$, about 305 mg/m$^2$, about 310 mg/m$^2$, about 315 mg/m$^2$, about 320 mg/m$^2$, about 325 mg/m$^2$, about 330 mg/m$^2$, about 335 mg/m$^2$, about 340 mg/m$^2$, about 345 mg/m$^2$, about 350 mg/m$^2$, about 355 mg/m$^2$, about 360 mg/m$^2$, about 365 mg/m$^2$, about 370 mg/m$^2$, about 375 mg/m$^2$, about 380 mg/m$^2$, about 385 mg/m$^2$, about 390 mg/m$^2$, about 395 mg/m$^2$, or about 400 mg/m$^2$. In some embodiments, the irinotecan is administered at least once per week at an amount of about 100 mg/m$^2$, about 105 mg/m$^2$, about 110 mg/m$^2$, about 115 mg/m$^2$, about 120 mg/m$^2$, about 125 mg/m$^2$, about 130 mg/m$^2$, about 135 mg/m$^2$, about 140 mg/m$^2$, about 145 mg/m$^2$, about 150 mg/m$^2$, about 155 mg/m$^2$, about 160 mg/m$^2$, about 165 mg/m$^2$, about 170 mg/m$^2$, about 175 mg/m$^2$, about 180 mg/m$^2$, about 185 mg/m$^2$, about 190 mg/m$^2$, about 195 mg/m$^2$, about 200 mg/m$^2$, about 205 mg/m$^2$, about 210 mg/m$^2$, about 215 mg/m$^2$, about 220 mg/m$^2$, about 225 mg/m$^2$, about 230 mg/m$^2$, about 235 mg/m$^2$, about 240 mg/m$^2$, about 245 mg/m$^2$, or about 250 mg/m$^2$. In some embodiments, the irinotecan is administered at least once per week at an amount of about 225 mg/m$^2$, about 250 mg/m$^2$, about 275 mg/m$^2$, about 300 mg/m$^2$, about 325 mg/m$^2$, or about 350 mg/m$^2$.

In some embodiments, the irinotecan is administered at about 225 mg/m$^2$, once over a three-week period. In some embodiments, the irinotecan is administered at about 150 mg/m$^2$, once over a three-week period. In some embodiments, the irinotecan is administered at about 75 mg/m$^2$, once over a three-week period.

In some embodiments, the irinotecan is administered at least twice per week. In some embodiments, the irinotecan is administered at least twice per week at an amount of any dosage as described above. In some embodiments, the irinotecan is administered twice over a three-week period. In some embodiments, the irinotecan is administered twice on consecutive days over a three-week period. In some embodiments, the irinotecan is administered twice over a three-week period as a tablet. In some embodiments, the irinotecan is administered twice over a three-week period as a capsule. In some embodiments, the irinotecan is administered twice over a three-week period as an oral solution. In some embodiments, the irinotecan is administered twice as two single doses over a three-week period.

In some embodiments, the irinotecan is administered at least twice per week at an amount of about 10 mg/m$^2$, about 15 mg/m$^2$, about 20 mg/m$^2$, about 25 mg/m$^2$, about 30 mg/m$^2$, about 35 mg/m$^2$, about 40 mg/m$^2$, about 45 mg/m$^2$, about 50 mg/m$^2$, about 55 mg/m$^2$, about 60 mg/m$^2$, about 65 mg/m$^2$, about 70 mg/m$^2$, about 75 mg/m$^2$, about 80 mg/m$^2$, about 85 mg/m$^2$, about 90 mg/m$^2$, about 95 mg/m$^2$, or about 100 mg/m$^2$. In some embodiments, the irinotecan is administered at least twice per week at an amount of about 105 mg/m$^2$, about 110 mg/m$^2$, about 115 mg/m$^2$, about 120 mg/m$^2$, about 125 mg/m$^2$, about 130 mg/m$^2$, about 135 mg/m$^2$, about 140 mg/m$^2$, about 145 mg/m$^2$, or about 150 mg/m$^2$.

In some embodiments, the irinotecan is administered at least twice per week at an amount of about 100 mg/m$^2$, about 105 mg/m$^2$, about 110 mg/m$^2$, about 115 mg/m$^2$, about 120 mg/m$^2$, about 125 mg/m$^2$, about 130 mg/m$^2$, about 135 mg/m$^2$, about 140 mg/m$^2$, about 145 mg/m$^2$, about 150 mg/m$^2$, about 155 mg/m$^2$, about 160 mg/m$^2$, about 165 mg/m$^2$, about 170 mg/m$^2$, about 175 mg/m$^2$, about 180 mg/m$^2$, about 185 mg/m$^2$, about 190 mg/m$^2$, about 195 mg/m$^2$, about 200 mg/m$^2$, about 205 mg/m$^2$, about 210 mg/m$^2$, about 215 mg/m$^2$, about 220 mg/m$^2$, about 225 mg/m$^2$, about 230 mg/m$^2$, about 235 mg/m$^2$, about 240 mg/m$^2$, about 245 mg/m$^2$, about 250 mg/m$^2$, about 255 mg/m$^2$, about 260 mg/m$^2$, about 265 mg/m$^2$, about 270 mg/m$^2$, about 275 mg/m$^2$, about 280 mg/m$^2$, about 285 mg/m$^2$, about 290 mg/m$^2$, about 295 mg/m$^2$, about 300 mg/m$^2$, about 305 mg/m$^2$, about 310 mg/m$^2$, about 315 mg/m², about 320 mg/m², about 325 mg/m², about 330 mg/m², about 335 mg/m², about 340 mg/m², about 345 mg/m², about 350 mg/m², about 355 mg/m², about 360 mg/m², about 365 mg/m², about 370 mg/m², about 375 mg/m², about 380 mg/m², about 385 mg/m², about 390 mg/m², about 395 mg/m², or about 400 mg/m². In some embodiments, the irinotecan is administered at least twice per week at an amount of about 150 mg/m², about 155 mg/m², about 160 mg/m², about 165 mg/m², about 170 mg/m², about 175 mg/m², about 180 mg/m², about 185 mg/m², about 190 mg/m², about 195 mg/m², about 200 mg/m², about 205 mg/m², about 210 mg/m², about 215 mg/m², about 220 mg/m², about 225 mg/m², about 230 mg/m², about 235 mg/m², about 240 mg/m², about 245 mg/m², or about 250 mg/m². In some embodiments, the irinotecan is administered at least twice per week at an amount of about 225 mg/m², about 250 mg/m², about 275 mg/m², about 300 mg/m², about 325 mg/m², or about 350 mg/m².

In some embodiments, the irinotecan is administered at about 225 mg/m², twice on consecutive days over a three-week period. In some embodiments, the irinotecan is administered at single doses at about 225 mg/m², twice on consecutive days over a three-week period. In some embodiments, the irinotecan is administered at about 150 mg/m², twice on consecutive days over a three-week period. In some embodiments, the irinotecan is administered at single doses at about 150 mg/m², twice on consecutive days over a three-week period. In some embodiments, the irinotecan is administered at about 75 mg/m², twice on consecutive days over a three-week period. In some embodiments, the irinotecan is administered at single doses at about 75 mg/m², twice on consecutive days over a three-week period.

In some embodiments, the irinotecan is administered at least three times per week. In some embodiments, the irinotecan is administered at least three times per week at an amount of any dosage as described above. In some embodiments, the irinotecan is administered three times over a three-week period. In some embodiments, the irinotecan is administered three times on consecutive days over a three-week period. In some embodiments, the irinotecan is administered three times over a three-week period as a tablet. In some embodiments, the irinotecan is administered three times over a three-week period as a capsule. In some embodiments, the irinotecan is administered three times over a three-week period as an oral solution. In some embodiments, the irinotecan is administered at three single doses over a three-week period.

In some embodiments, the irinotecan is administered at least three times per week at an amount of about 10 mg/m², about 15 mg/m², about 20 mg/m², about 25 mg/m², about 30 mg/m², about 35 mg/m², about 40 mg/m², about 45 mg/m², about 50 mg/m², about 55 mg/m², about 60 mg/m², about 65 mg/m², about 70 mg/m², about 75 mg/m², about 80 mg/m², about 85 mg/m², about 90 mg/m², about 95 mg/m², or about 100 mg/m². In some embodiments, the irinotecan is administered at least three times per week at an amount of about 105 mg/m², about 110 mg/m², about 115 mg/m², about 120 mg/m², about 125 mg/m², about 130 mg/m², about 135 mg/m², about 140 mg/m², about 145 mg/m², or about 150 mg/m².

In some embodiments, the irinotecan is administered at least three times per week at an amount of about 100 mg/m², about 105 mg/m², about 110 mg/m², about 115 mg/m², about 120 mg/m², about 125 mg/m², about 130 mg/m², about 135 mg/m², about 140 mg/m², about 145 mg/m², about 150 mg/m², about 155 mg/m², about 160 mg/m², about 165 mg/m², about 170 mg/m², about 175 mg/m², about 180 mg/m², about 185 mg/m², about 190 mg/m², about 195 mg/m², about 200 mg/m², about 205 mg/m², about 210 mg/m², about 215 mg/m², about 220 mg/m², about 225 mg/m², about 230 mg/m², about 235 mg/m², about 240 mg/m², about 245 mg/m², about 250 mg/m², about 255 mg/m², about 260 mg/m², about 265 mg/m², about 270 mg/m², about 275 mg/m², about 280 mg/m², about 285 mg/m², about 290 mg/m², about 295 mg/m², about 300 mg/m², about 305 mg/m², about 310 mg/m², about 315 mg/m², about 320 mg/m², about 325 mg/m², about 330 mg/m², about 335 mg/m², about 340 mg/m², about 345 mg/m², about 350 mg/m², about 355 mg/m², about 360 mg/m², about 365 mg/m², about 370 mg/m², about 375 mg/m², about 380 mg/m², about 385 mg/m², about 390 mg/m², about 395 mg/m², or about 400 mg/m². In some embodiments, the irinotecan is administered at least three times per week at an amount of about 150 mg/m², about 155 mg/m², about 160 mg/m², about 165 mg/m², about 170 mg/m², about 175 mg/m², about 180 mg/m², about 185 mg/m², about 190 mg/m², about 195 mg/m², about 200 mg/m², about 205 mg/m², about 210 mg/m², about 215 mg/m², about 220 mg/m², about 225 mg/m², about 230 mg/m², about 235 mg/m², about 240 mg/m², about 245 mg/m², or about 250 mg/m². In some embodiments, the irinotecan is administered at least three times per week at an amount of about 225 mg/m², about 250 mg/m², about 275 mg/m², about 300 mg/m², about 325 mg/m², or about 350 mg/m².

In some embodiments, the irinotecan is administered at about 225 mg/m², three times on consecutive days over a three-week period. In some embodiments, the irinotecan is administered at single doses at about 225 mg/m², three times on consecutive days over a three-week period. In some embodiments, the irinotecan is administered at about 150 mg/m², three times on consecutive days over a three-week period. In some embodiments, the irinotecan is administered at single doses at about 150 mg/m², three times on consecutive days over a three-week period. In some embodiments, the irinotecan is administered at about 75 mg/m², three times on consecutive days over a three-week period. In some embodiments, the irinotecan is administered at single doses at about 75 mg/m², three times on consecutive days over a three-week period.

In some embodiments, the irinotecan is administered at least four times per week. In some embodiments, the irinotecan is administered at least four times per week at an amount of any dosage as described above. In some embodiments, the irinotecan is administered four times over a three-week period. In some embodiments, the irinotecan is administered four times on consecutive days over a three-week period. In some embodiments, the irinotecan is administered four times over a three-week period as a tablet. In some embodiments, the irinotecan is administered four times over a three-week period as a capsule. In some embodiments, the irinotecan is administered four times over a three-week period as an oral solution. In some embodiments, the irinotecan is administered four times at single doses over a three-week period.

In some embodiments, the irinotecan is administered at least four times per week at an amount of about 25 mg/m², about 30 mg/m², about 35 mg/m², about 40 mg/m², about 45 mg/m², about 50 mg/m², about 55 mg/m², about 60 mg/m², about 65 mg/m², about 70 mg/m², about 75 mg/m², about 80 mg/m², about 85 mg/m², about 90 mg/m², about 95 mg/m², or about 100 mg/m². In some embodiments, the irinotecan is administered at least four times per week at an amount of about 105 mg/m², about 110 mg/m², about 115 mg/m², about 120 mg/m², about 125 mg/m², about 130 mg/m², about 135 mg/m², about 140 mg/m², about 145 mg/m², or about 150 mg/m².

In some embodiments, the irinotecan is administered at least four times per week at an amount of about 150 mg/m², about 155 mg/m², about 160 mg/m², about 165 mg/m², about 170 mg/m², about 175 mg/m², about 180 mg/m², about 185 mg/m², about 190 mg/m², about 195 mg/m², about 200 mg/m², about 205 mg/m², about 210 mg/m², about 215 mg/m², about 220 mg/m², about 225 mg/m², about 230 mg/m², about 235 mg/m², about 240 mg/m², about 245 mg/m², about 250 mg/m², about 255 mg/m², about 260 mg/m², about 265 mg/m², about 270 mg/m², about 275 mg/m², about 280 mg/m², about 285 mg/m², about 290 mg/m², about 295 mg/m², about 300 mg/m², about 305 mg/m², about 310 mg/m², about 315 mg/m², about 320 mg/m², about 325 mg/m², about 330 mg/m², about 335 mg/m², about 340 mg/m², about 345 mg/m², about 350 mg/m², about 355 mg/m², about 360 mg/m², about 365 mg/m², about 370 mg/m², about 375 mg/m², about 380 mg/m², about 385 mg/m², about 390 mg/m², about 395 mg/m², or about 400 mg/m². In some embodiments, the irinotecan is administered at least four times per week at an amount of about 125 mg/m², about 130 mg/m², about 135 mg/m², about 140 mg/m², about 145 mg/m², about 150 mg/m², about 155 mg/m², about 160 mg/m², about 165 mg/m², about 170 mg/m², about 175 mg/m², about 180 mg/m², about 185 mg/m², about 190 mg/m², about 195 mg/m², about 200 mg/m², about 205 mg/m², about 210 mg/m², about 215 mg/m², about 220 mg/m², about 225 mg/m², about 230 mg/m², about 235 mg/m², about 240 mg/m², about 245 mg/m², or about 250 mg/m². In some embodiments, the irinotecan is administered at least four times per week at an amount of about 125 mg/m², about 130 mg/m², about 135 mg/m², about 140 mg/m², about 145 mg/m², about 150 mg/m², about 155 mg/m², about 160 mg/m², about 165 mg/m², about 170 mg/m², about 175 mg/m², about 200 mg/m², about 225 mg/m², or about 250 mg/m².

In some embodiments, the irinotecan is administered at about 225 mg/m², four times on consecutive days over a three-week period. In some embodiments, the irinotecan is administered at single doses at about 225 mg/m², four times on consecutive days over a three-week period. In some embodiments, the irinotecan is administered at about 150 mg/m², four times on consecutive days over a three-week period. In some embodiments, the irinotecan is administered at single doses at about 150 mg/m², four times on consecutive days over a three-week period. In some embodiments, the irinotecan is administered at about 75 mg/m², four times on consecutive days over a three-week period. In some embodiments, the irinotecan is administered at single doses at about 75 mg/m², four times on consecutive days over a three-week period.

In some embodiments, the irinotecan is administered at least five times per week. In some embodiments, the irinotecan is administered at least five times per week at an amount of any dosage as described above. In some embodiments, the irinotecan is administered five times over a three-week period. In some embodiments, the irinotecan is administered five times on consecutive days over a three-week period. In some embodiments, the irinotecan is administered five times over a three-week period as a tablet. In some embodiments, the irinotecan is administered five times over a three-week period as a capsule. In some embodiments, the irinotecan is administered five times over a three-week period as an oral solution. In some embodiments, the irinotecan is administered at single doses five times over a three-week period.

In some embodiments, the irinotecan is administered at least five times per week at an amount of about 25 mg/m², about 30 mg/m², about 35 mg/m², about 40 mg/m², about 45 mg/m², about 50 mg/m², about 55 mg/m², about 60 mg/m², about 65 mg/m², about 70 mg/m², about 75 mg/m², about 80 mg/m², about 85 mg/m², about 90 mg/m², about 95 mg/m², or about 100 mg/m². In some embodiments, the irinotecan is administered at least five times per week at an amount of about 110 mg/m², about 120 mg/m², about 130 mg/m², about 140 mg/m², or about 150 mg/m².

In some embodiments, the irinotecan is administered at least five times per week at an amount of about 150 mg/m², about 155 mg/m², about 160 mg/m², about 165 mg/m², about 170 mg/m², about 175 mg/m², about 180 mg/m², about 185 mg/m², about 190 mg/m², about 195 mg/m², about 200 mg/m², about 205 mg/m², about 210 mg/m², about 215 mg/m², about 220 mg/m², about 225 mg/m², about 230 mg/m², about 235 mg/m², about 240 mg/m², about 245 mg/m², about 250 mg/m², about 255 mg/m², about 260 mg/m², about 265 mg/m², about 270 mg/m², about 275 mg/m², about 280 mg/m², about 285 mg/m², about 290 mg/m², about 295 mg/m², about 300 mg/m², about 305 mg/m², about 310 mg/m², about 315 mg/m², about 320 mg/m², about 325 mg/m², about 330 mg/m², about 335 mg/m², about 340 mg/m², about 345 mg/m², about 350 mg/m², about 355 mg/m², about 360 mg/m², about 365 mg/m², about 370 mg/m², about 375 mg/m², about 380 mg/m², about 385 mg/m², about 390 mg/m², about 395 mg/m², or about 400 mg/m². In some embodiments, the irinotecan is administered at least five times per week at an amount of about 250 mg/m², about 275 mg/m², about 300 mg/m², about 325 mg/m², or about 350 mg/m².

In some embodiments, the irinotecan is administered at about 225 mg/m², five times on consecutive days over a three-week period. In some embodiments, the irinotecan is administered at single doses at about 225 mg/m², five times on consecutive days over a three-week period. In some embodiments, the irinotecan is administered at about 150 mg/m², five times on consecutive days over a three-week period. In some embodiments, the irinotecan is administered at single doses at about 150 mg/m², five times on consecutive days over a three-week period. In some embodiments, the irinotecan is administered at about 75 mg/m², five times on consecutive days over a three-week period. In some embodiments, the irinotecan is administered at single doses at about 75 mg/m², five times on consecutive days over a three-week period.

In some embodiments, the irinotecan is administered at least six times per week. In some embodiments, the irinotecan is administered at least six times per week at an amount of any dosage as described above. In some embodiments, the irinotecan is administered six times over a three-week period. In some embodiments, the irinotecan is administered six times on consecutive days over a three-week period. In some embodiments, the irinotecan is administered six times over a three-week period as a tablet. In some embodiments, the irinotecan is administered six times over a three-week period as a capsule. In some embodiments, the irinotecan is administered six times over a three-week period as an oral solution. In some embodiments, the irinotecan is administered at three single doses over a three-week period.

In some embodiments, the irinotecan is administered at least six times per week at an amount of about 10 mg/m², about 15 mg/m$^2$, about 20 mg/m$^2$, about 25 mg/m$^2$, about 30 mg/m$^2$, about 35 mg/m$^2$, about 40 mg/m$^2$, about 45 mg/m$^2$, about 50 mg/m$^2$, about 55 mg/m$^2$, about 60 mg/m$^2$, about 65 mg/m$^2$, about 70 mg/m$^2$, about 75 mg/m$^2$, about 80 mg/m$^2$, about 85 mg/m$^2$, about 90 mg/m$^2$, about 95 mg/m$^2$, or about 100 mg/m$^2$. In some embodiments, the irinotecan is administered at least six times per week at an amount of about 105 mg/m$^2$, about 110 mg/m$^2$, about 115 mg/m$^2$, about 120 mg/m$^2$, about 125 mg/m$^2$, about 130 mg/m$^2$, about 135 mg/m$^2$, about 140 mg/m$^2$, about 145 mg/m$^2$, or about 150 mg/m$^2$.

In some embodiments, the irinotecan is administered at least six times per week at an amount of about 100 mg/m$^2$, about 105 mg/m$^2$, about 110 mg/m$^2$, about 115 mg/m$^2$, about 120 mg/m$^2$, about 125 mg/m$^2$, about 130 mg/m$^2$, about 135 mg/m$^2$, about 140 mg/m$^2$, about 145 mg/m$^2$, about 150 mg/m$^2$, about 155 mg/m$^2$, about 160 mg/m$^2$, about 165 mg/m$^2$, about 170 mg/m$^2$, about 175 mg/m$^2$, about 180 mg/m$^2$, about 185 mg/m$^2$, about 190 mg/m$^2$, about 195 mg/m$^2$, about 200 mg/m$^2$, about 205 mg/m$^2$, about 210 mg/m$^2$, about 215 mg/m$^2$, about 220 mg/m$^2$, about 225 mg/m$^2$, about 230 mg/m$^2$, about 235 mg/m$^2$, about 240 mg/m$^2$, about 245 mg/m$^2$, about 250 mg/m$^2$, about 255 mg/m$^2$, about 260 mg/m$^2$, about 265 mg/m$^2$, about 270 mg/m$^2$, about 275 mg/m$^2$, about 280 mg/m$^2$, about 285 mg/m$^2$, about 290 mg/m$^2$, about 295 mg/m$^2$, about 300 mg/m$^2$, about 305 mg/m$^2$, about 310 mg/m$^2$, about 315 mg/m$^2$, about 320 mg/m$^2$, about 325 mg/m$^2$, about 330 mg/m$^2$, about 335 mg/m$^2$, about 340 mg/m$^2$, about 345 mg/m$^2$, about 350 mg/m$^2$, about 355 mg/m$^2$, about 360 mg/m$^2$, about 365 mg/m$^2$, about 370 mg/m$^2$, about 375 mg/m$^2$, about 380 mg/m$^2$, about 385 mg/m$^2$, about 390 mg/m$^2$, about 395 mg/m$^2$, or about 400 mg/m$^2$. In some embodiments, the irinotecan is administered at least six times per week at an amount of about 150 mg/m$^2$, about 155 mg/m$^2$, about 160 mg/m$^2$, about 165 mg/m$^2$, about 170 mg/m$^2$, about 175 mg/m$^2$, about 180 mg/m$^2$, about 185 mg/m$^2$, about 190 mg/m$^2$, about 195 mg/m$^2$, about 200 mg/m$^2$, about 205 mg/m$^2$, about 210 mg/m$^2$, about 215 mg/m$^2$, about 220 mg/m$^2$, about 225 mg/m$^2$, about 230 mg/m$^2$, about 235 mg/m$^2$, about 240 mg/m$^2$, about 245 mg/m$^2$, or about 250 mg/m$^2$. In some embodiments, the irinotecan is administered at least six times per week at an amount of about 225 mg/m$^2$, about 250 mg/m$^2$, about 275 mg/m$^2$, about 300 mg/m$^2$, about 325 mg/m$^2$, or about 350 mg/m$^2$.

In some embodiments, the irinotecan is administered at about 225 mg/m$^2$, six times on consecutive days over a three-week period. In some embodiments, the irinotecan is administered at single doses at about 225 mg/m$^2$, six times on consecutive days over a three-week period. In some embodiments, the irinotecan is administered at about 150 mg/m$^2$, six times on consecutive days over a three-week period. In some embodiments, the irinotecan is administered at single doses at about 150 mg/m$^2$, six times on consecutive days over a three-week period. In some embodiments, the irinotecan is administered at about 75 mg/m$^2$, six times on consecutive days over a three-week period. In some embodiments, the irinotecan is administered at single doses at about 75 mg/m$^2$, six times on consecutive days over a three-week period.

In some embodiments, the irinotecan is administered at least seven times per week. In some embodiments, the irinotecan is administered at least seven times per week at an amount of any dosage as described above. In some embodiments, the irinotecan is administered seven times over a three-week period. In some embodiments, the irinotecan is administered seven times on consecutive days over a three-week period. In some embodiments, the irinotecan is administered seven times over a three-week period as a tablet. In some embodiments, the irinotecan is administered seven times over a three-week period as a capsule. In some embodiments, the irinotecan is administered seven times over a three-week period as an oral solution. In some embodiments, the irinotecan is administered at three single doses over a three-week period.

In some embodiments, the irinotecan is administered at least seven times per week at an amount of about 10 mg/m$^2$, about 15 mg/m$^2$, about 20 mg/m$^2$, about 25 mg/m$^2$, about 30 mg/m$^2$, about 35 mg/m$^2$, about 40 mg/m$^2$, about 45 mg/m$^2$, about 50 mg/m$^2$, about 55 mg/m$^2$, about 60 mg/m$^2$, about 65 mg/m$^2$, about 70 mg/m$^2$, about 75 mg/m$^2$, about 80 mg/m$^2$, about 85 mg/m$^2$, about 90 mg/m$^2$, about 95 mg/m$^2$, or about 100 mg/m$^2$. In some embodiments, the irinotecan is administered at least seven times per week at an amount of about 105 mg/m$^2$, about 110 mg/m$^2$, about 115 mg/m$^2$, about 120 mg/m$^2$, about 125 mg/m$^2$, about 130 mg/m$^2$, about 135 mg/m$^2$, about 140 mg/m$^2$, about 145 mg/m$^2$, or about 150 mg/m$^2$.

In some embodiments, the irinotecan is administered at least seven times per week at an amount of about 100 mg/m$^2$, about 105 mg/m$^2$, about 110 mg/m$^2$, about 115 mg/m$^2$, about 120 mg/m$^2$, about 125 mg/m$^2$, about 130 mg/m$^2$, about 135 mg/m$^2$, about 140 mg/m$^2$, about 145 mg/m$^2$, about 150 mg/m$^2$, about 155 mg/m$^2$, about 160 mg/m$^2$, about 165 mg/m$^2$, about 170 mg/m$^2$, about 175 mg/m$^2$, about 180 mg/m$^2$, about 185 mg/m$^2$, about 190 mg/m$^2$, about 195 mg/m$^2$, about 200 mg/m$^2$, about 205 mg/m$^2$, about 210 mg/m$^2$, about 215 mg/m$^2$, about 220 mg/m$^2$, about 225 mg/m$^2$, about 230 mg/m$^2$, about 235 mg/m$^2$, about 240 mg/m$^2$, about 245 mg/m$^2$, about 250 mg/m$^2$, about 255 mg/m$^2$, about 260 mg/m$^2$, about 265 mg/m$^2$, about 270 mg/m$^2$, about 275 mg/m$^2$, about 280 mg/m$^2$, about 285 mg/m$^2$, about 290 mg/m$^2$, about 295 mg/m$^2$, about 300 mg/m$^2$, about 305 mg/m$^2$, about 310 mg/m$^2$, about 315 mg/m$^2$, about 320 mg/m$^2$, about 325 mg/m$^2$, about 330 mg/m$^2$, about 335 mg/m$^2$, about 340 mg/m$^2$, about 345 mg/m$^2$, about 350 mg/m$^2$, about 355 mg/m$^2$, about 360 mg/m$^2$, about 365 mg/m$^2$, about 370 mg/m$^2$, about 375 mg/m$^2$, about 380 mg/m$^2$, about 385 mg/m$^2$, about 390 mg/m$^2$, about 395 mg/m$^2$, or about 400 mg/m$^2$. In some embodiments, the irinotecan is administered at least seven times per week at an amount of about 150 mg/m$^2$, about 155 mg/m$^2$, about 160 mg/m$^2$, about 165 mg/m$^2$, about 170 mg/m$^2$, about 175 mg/m$^2$, about 180 mg/m$^2$, about 185 mg/m$^2$, about 190 mg/m$^2$, about 195 mg/m$^2$, about 200 mg/m$^2$, about 205 mg/m$^2$, about 210 mg/m$^2$, about 215 mg/m$^2$, about 220 mg/m$^2$, about 225 mg/m$^2$, about 230 mg/m$^2$, about 235 mg/m$^2$, about 240 mg/m$^2$, about 245 mg/m$^2$, or about 250 mg/m$^2$. In some embodiments, the irinotecan is administered at least seven times per week at an amount of about 225 mg/m$^2$, about 250 mg/m$^2$, about 275 mg/m$^2$, about 300 mg/m$^2$, about 325 mg/m$^2$, or about 350 mg/m$^2$.

In some embodiments, the irinotecan is administered at about 225 mg/m$^2$, seven times on consecutive days over a three-week period. In some embodiments, the irinotecan is administered at single doses at about 225 mg/m$^2$, seven times on consecutive days over a three-week period. In some embodiments, the irinotecan is administered at about 150 mg/m$^2$, seven times on consecutive days over a three-week period. In some embodiments, the irinotecan is administered at single doses at about 150 mg/m$^2$, seven times on consecutive days over a three-week period. In some embodiments, the irinotecan is administered at about 75 mg/m², seven times on consecutive days over a three-week period. In some embodiments, the irinotecan is administered at single doses at about 75 mg/m², seven times on consecutive days over a three-week period.

In some embodiments, oral administration of irinotecan (i.e., administration of an oral formulation of irinotecan) is preceded by IV administration of irinotecan. In some embodiments, the irinotecan is administered intravenously according to the dosage amount and dosage regimen described herein, followed by administration of an oral formulation of irinotecan as described herein. In some embodiments, the irinotecan is administered intravenously according to the dosage amount once on the first day of the first week, and the administration of an oral formulation of irinotecan starts on the first day of the fourth week, according to the dosage amount and dosage regimen described herein.

In some embodiments, oral administration of irinotecan (i.e., administration of an oral formulation of irinotecan) is preceded by a premedication regimen. In some embodiments, the premedication comprises an antiemetic (e.g., a 5-HT$^3$ blocker such as ondansetron or granisetron), an oral corticosteroid, or an anti-histamine.

In some embodiments, the premedication comprises an antiemetic. In some embodiments, the premedication comprises a 5-HT$^3$ blocker. In some embodiments, the premedication comprises ondansetron or granisetron. In some embodiments, the premedication comprises an oral corticosteroid. In some embodiments, the premedication comprises an anti-histamine.

In some embodiments, Compound A is administered orally.

In some embodiments, Compound A is administered at an amount of about 1 mg to about 500 mg.

In some embodiments, Compound A is administered at about 1 mg to 400 mg.

In some embodiments, Compound A is administered at about 1 mg to 300 mg.

In some embodiments, Compound A is administered at about 5 mg to 200 mg.

In some embodiments, Compound A is administered at about 10 mg to 100 mg.

In some embodiments, Compound A is administered at about 15 mg to 50 mg.

In some embodiments, Compound A is administered at about 5 mg.

In some embodiments, Compound A is administered at about 10 mg.

In some embodiments, Compound A is administered at about 15 mg.

In some embodiments, Compound A is administered at about 20 mg.

In some embodiments, Compound A is administered at about 25 mg.

In some embodiments, Compound A is administered at about 30 mg.

In some embodiments, Compound A is administered at about 35 mg.

In some embodiments, Compound A is administered at about 40 mg.

In some embodiments, Compound A is administered at about 45 mg.

In some embodiments, Compound A is administered at about 50 mg.

In some embodiments, Compound A and the irinotecan are administered on the same day.

In some embodiments, Compound A and the irinotecan are administered on the same day as a single dose.

In some embodiments, Compound A and the irinotecan are administered on the same day as a single dose once a week.

In some embodiments, Compound A and the irinotecan are administered on the same day as a single dose once every three weeks.

In some embodiments, Compound A and the irinotecan are administered on the same day as two single daily doses.

In some embodiments, Compound A and the irinotecan are administered on the same day as two single daily doses once a week.

In some embodiments, Compound A and the irinotecan are administered on the same day as two single daily doses once every three weeks.

In some embodiments, Compound A is administered simultaneously with irinotecan.

In some embodiments, Compound A is administered before the irinotecan is administered.

In some embodiments, Compound A is administered about 5 minutes before the irinotecan is administered.

In some embodiments, Compound A is administered about 10 minutes before the irinotecan is administered.

In some embodiments, Compound A is administered about 15 minutes before the irinotecan is administered.

In some embodiments, Compound A is administered about 30 minutes before the irinotecan is administered.

In some embodiments, Compound A is administered about 45 minutes before the irinotecan is administered.

In some embodiments, Compound A is administered about 60 minutes before the irinotecan is administered.

In some embodiments, Compound A is administered about 2 hours before the irinotecan is administered.

In some embodiments, Compound A is administered about 3 hours before the irinotecan is administered.

In some embodiments, Compound A is administered about 4 hours before the irinotecan is administered.

In some embodiments, Compound A is administered about 6 hours before the irinotecan is administered.

In some embodiments, Compound A is administered about 8 hours before the irinotecan is administered.

In some embodiments, the plasma exposure of the orally administered irinotecan, as measured by $AUC_{(0\to\infty)}$, is equal to or greater than the plasma exposure of intravenously administered irinotecan (e.g., Camptosar®) at an amount of about 50-400 mg/m² (e.g., 350 mg/m²) over a period of about 1-24 hours once every three weeks, or at an amount of about 50-400 mg/m² (e.g., 125 or 180 mg/m²) over a period of about 1-24 hours once every two weeks, or at an amount of about 30-200 mg/m² (e.g., 125 mg/m²) over a period of about 1-24 hours twice every week (e.g., for a period of 3 or 4 weeks), as measured by $AUC_{(0\to\infty)}$.

In some embodiments, the plasma exposure of the orally administered irinotecan, as measured by $AUC_{(0\to\infty)}$, is equal to or greater than the plasma exposure of intravenously administered irinotecan (e.g., Camptosar®) at an amount of about 50-400 mg/m² (e.g., 350 mg/m²) over a period of about 1-24 hours once every three weeks, or at an amount of about 50-400 mg/m² (e.g., 125 or 180 mg/m²) over a period of about 1-24 hours once every two weeks, or at an amount of about 30-200 mg/m² (e.g., 125 mg/m²) over a period of about 1-24 hours twice every week (e.g., for a period of 3 or 4 weeks), as measured by $AUC_{(0\to\infty)}$.

In some embodiments, the plasma exposure of the orally administered irinotecan, as measured by $AUC_{(0\to\infty)}$, is equal to or greater than the plasma exposure of intravenously administered irinotecan (e.g., Camptosar®) at an amount of about 50-400 mg/m² (e.g., 350 mg/m²) over a period of about 1-20 hours once every three weeks, or at an amount of about 50-400 mg/m² (e.g., 125 or 180 mg/m²) over a period of about 1-20 hours once every two weeks, or at an amount of about 30-200 mg/m² (e.g., 125 mg/m²) over a period of about 1-20 hours twice every week (e.g., for a period of 3 or 4 weeks), as measured by $AUC_{(0\to\infty)}$.

In some embodiments, the plasma exposure of the orally administered irinotecan, as measured by $AUC_{(0\to\infty)}$, is equal to or greater than the plasma exposure of intravenously administered irinotecan (e.g., Camptosar®) at an amount of about 50-400 mg/m² (e.g., 350 mg/m²) over a period of about 1-16 hours once every three weeks, or at an amount of about 50-400 mg/m² (e.g., 125 or 180 mg/m²) over a period of about 1-16 hours once every two weeks, or at an amount of about 30-200 mg/m² (e.g., 125 mg/m²) over a period of about 1-16 hours twice every week (e.g., for a period of 3 or 4 weeks), as measured by $AUC_{(0\to\infty)}$.

In some embodiments, the plasma exposure of the orally administered irinotecan, as measured by $AUC_{(0\to\infty)}$, is equal to or greater than the plasma exposure of intravenously administered irinotecan (e.g., Camptosar®) at an amount of about 50-400 mg/m² (e.g., 350 mg/m²) over a period of about 2-12 hours once every three weeks, or at an amount of about 50-400 mg/m² (e.g., 125 or 180 mg/m²) over a period of about 2-12 hours once every two weeks, or at an amount of about 30-200 mg/m² (e.g., 125 mg/m²) over a period of about 2-12 hours twice every week (e.g., for a period of 3 or 4 weeks), as measured by $AUC_{(0\to\infty)}$.

In some embodiments, the plasma exposure of the orally administered irinotecan, as measured by $AUC_{(0\to\infty)}$, is equal to or greater than the plasma exposure of intravenously administered irinotecan (e.g., Camptosar®) at an amount of about 50-400 mg/m² (e.g., 350 mg/m²) over a period of about 2-10 hours once every three weeks, or at an amount of about 50-400 mg/m² (e.g., 125 or 180 mg/m²) over a period of about 2-10 hours once every two weeks, or at an amount of about 30-200 mg/m² (e.g., 125 mg/m²) over a period of about 2-10 hours twice every week (e.g., for a period of 3 or 4 weeks), as measured by $AUC_{(0\to\infty)}$.

In some embodiments, the plasma exposure of the orally administered irinotecan, as measured by $AUC_{(0\to\infty)}$, is equal to or greater than the plasma exposure of intravenously administered irinotecan (e.g., Camptosar®) at an amount of about 50-400 mg/m² (e.g., 350 mg/m²) over a period of about 3-8 hours once every three weeks, or at an amount of about 50-400 mg/m² (e.g., 125 or 180 mg/m²) over a period of about 3-8 hours once every two weeks, or at an amount of about 30-200 mg/m² (e.g., 125 mg/m²) over a period of about 3-8 hours twice every week (e.g., for a period of 3 or 4 weeks), as measured by $AUC_{(0\to\infty)}$.

In some embodiments, the plasma exposure of the orally administered irinotecan, as measured by $AUC_{(0\to\infty)}$, is equal to or greater than the plasma exposure of intravenously administered irinotecan (e.g., Camptosar®) at an amount of about 50-400 mg/m² (e.g., 350 mg/m²) over a period of about 60 minutes once every three weeks, or at an amount of about 50-400 mg/m² (e.g., 125 or 180 mg/m²) over a period of about 60 minutes once every two weeks, or at an amount of about 30-200 mg/m² (e.g., 125 mg/m²) over a period of about 60 minutes twice every week (e.g., for a period of 3 or 4 weeks), as measured by $AUC_{(0\to\infty)}$.

In some embodiments, the plasma exposure of the orally administered irinotecan, as measured by $AUC_{(0\to\infty)}$, is equal to or greater than the plasma exposure of intravenously administered irinotecan (e.g., Camptosar®) at an amount of about 70-90 mg/m² over a period of about 60 minutes once every three weeks, as measured by $AUC_{(0\to\infty)}$.

In some embodiments, the plasma exposure of the orally administered irinotecan, as measured by $AUC_{(0\to\infty)}$, is equal to or greater than the plasma exposure of intravenously administered irinotecan (e.g., Camptosar®) at an amount of about 75-85 mg/m² over a period of about 60 minutes once every three weeks, as measured by $AUC_{(0\to\infty)}$.

In some embodiments, the plasma exposure of the orally administered irinotecan, as measured by $AUC_{(0\to\infty)}$, is equal to or greater than the plasma exposure of intravenously administered irinotecan (e.g., Camptosar®) at an amount of about 80 mg/m² over a period of about 60 minutes once every three weeks, as measured by $AUC_{(0\to\infty)}$.

In some embodiments, the plasma exposure of the orally administered irinotecan, as measured by $AUC_{(0\to\infty)}$, is equal to or greater than the plasma exposure of intravenously administered irinotecan (e.g., Camptosar®) at an amount of about 75 mg/m² over a period of about 60 minutes, as measured by $AUC_{(0\to\infty)}$.

In some embodiments, the $AUC_{(0\to\infty)}$ of the orally administered irinotecan is equal to the $AUC_{(0\to\infty)}$ of intravenously administered irinotecan e.g., Camptosar®) at an amount of about 50-400 mg/m² (e.g., 350 mg/m²) over a period of about 60 minutes once every three weeks, or at an amount of about 50-400 mg/m² (e.g., 125 or 180 mg/m²) over a period of about 60 minutes once every two weeks, or at an amount of about 30-200 mg/m² (e.g., 125 mg/m²) over a period of about 60 minutes twice every week (e.g., for a period of 3 or 4 weeks), as measured by $AUC_{(0\to\infty)}$.

In some embodiments, the $AUC_{(0\to\infty)}$ of the orally administered irinotecan is equal to the $AUC_{(0\to\infty)}$ of intravenously administered irinotecan e.g., Camptosar®) at an amount of about 70-90 mg/m² over a period of about 60 minutes once every three weeks, as measured by $AUC_{(0\to\infty)}$.

In some embodiments, the $AUC_{(0\to\infty)}$ of the orally administered irinotecan is equal to the $AUC_{(0\to\infty)}$ of intravenously administered irinotecan e.g., Camptosar®) at an amount of about 75-85 mg/m² over a period of about 60 minutes once every three weeks, as measured by $AUC_{(0\to\infty)}$.

In some embodiments, the $AUC_{(0\to\infty)}$ of the orally administered irinotecan is equal to the $AUC_{(0\to\infty)}$ of intravenously administered irinotecan e.g., Camptosar®) at an amount of about 80 mg/m² over a period of about 60 minutes once every three weeks, as measured by $AUC_{(0\to\infty)}$.

In some embodiments, the $AUC_{(0\to\infty)}$ of the orally administered irinotecan is equal to the $AUC_{(0\to\infty)}$ of intravenously administered irinotecan e.g., Camptosar®) at an amount of about 75 mg/m² over a period of about 60 minutes once every three weeks, as measured by $AUC_{(0\to\infty)}$.

In some embodiments, the $AUC_{(0\to\infty)}$ of the orally administered irinotecan is greater than the $AUC_{(0\to\infty)}$ of intravenously administered irinotecan (e.g., Camptosar®) at an amount of about 50-400 mg/m² (e.g., 350 mg/m²) over a period of about 60 minutes once every three weeks, or at an amount of about 50-400 mg/m² (e.g., 125 or 180 mg/m²) over a period of about 60 minutes once every two weeks, or at an amount of about 30-200 mg/m² (e.g., 125 mg/m²) over a period of about 60 minutes twice every week (e.g., for a period of 3 or 4 weeks), as measured by $AUC_{(0\to\infty)}$.

In some embodiments, the $AUC_{(0\to\infty)}$ of the orally administered irinotecan is greater than the $AUC_{(0\to\infty)}$ of intravenously administered irinotecan (e.g., Camptosar®) at an amount of about 70-90 mg/m² over a period of about 60 minutes once every three weeks, as measured by $AUC_{(0\to\infty)}$.

In some embodiments, the $AUC_{(0\to\infty)}$ of the orally administered irinotecan is greater than the $AUC_{(0\to\infty)}$ of intravenously administered irinotecan (e.g., Camptosar®) at an amount of about 75-85 mg/m² over a period of about 60 minutes once every three weeks, as measured by $AUC_{(0\to\infty)}$.

In some embodiments, the $AUC_{(0\to\infty)}$ of the orally administered irinotecan is greater than the $AUC_{(0\to\infty)}$ of intravenously administered irinotecan (e.g., Camptosar®) at an amount of about 80 mg/m² over a period of about 60 minutes once every three weeks, as measured by $AUC_{(0\to\infty)}$.

In some embodiments, the $AUC_{(0\to\infty)}$ of the orally administered irinotecan is greater than the $AUC_{(0\to\infty)}$ of intravenously administered irinotecan (e.g., Camptosar®) at an amount of about 75 mg/m² over a period of about 60 minutes once every three weeks, as measured by $AUC_{(0\to\infty)}$.

In some embodiments, the $AUC_{(0\to\infty)}$ of the orally administered irinotecan is about 10, 15, 20, 25, 30, 35, 40, 45, 50, 55, 60, 65, 70, 75, 80, 85, 90, 95, or 100% greater than the $AUC_{(0\to\infty)}$ of intravenously administered irinotecan (e.g., Camptosar®) at an amount of about 10-400 mg/m², about 50-400 mg/m², about 100-400 mg/m², about 100 mg/m², about 125 mg/m², about 150 mg/m², about 175 mg/m², about 200 mg/m², about 250 mg/m², about 300 mg/m², or about 350 mg/m² over a period of about 60 minutes once every three weeks, or at an amount of about 50-400 mg/m² (e.g., 125 or 180 mg/m²) over a period of about 60 minutes once every two weeks, or at an amount of about 30-200 mg/m² (e.g., 125 mg/m²) over a period of about 60 minutes twice every week (e.g., for a period of 3 or 4 weeks), as measured by $AUC_{(0\to\infty)}$.

In some embodiments, the $AUC_{(0\to\infty)}$ of the orally administered irinotecan is at least about 10% greater (e.g., at least 10% greater) than the $AUC_{(0\to\infty)}$ of intravenously administered irinotecan (e.g., Camptosar®) at an amount of about 10-400 mg/m², about 50-400 mg/m², about 100-400 mg/m², about 100 mg/m², about 125 mg/m², about 150 mg/m², about 175 mg/m², about 200 mg/m², about 250 mg/m², about 300 mg/m², or about 350 mg/m² over a period of about 60 minutes once every three weeks, or at an amount of about 50-400 mg/m² (e.g., 125 or 180 mg/m²) over a period of about 60 minutes once every two weeks, or at an amount of about 30-200 mg/m² (e.g., 125 mg/m²) over a period of about 60 minutes twice every week (e.g., for a period of 3 or 4 weeks), as measured by $AUC_{(0\to\infty)}$.

In some embodiments, the $AUC_{(0\to\infty)}$ of the orally administered irinotecan is at least about 20% greater (e.g., at least 20% greater) than the $AUC_{(0\to\infty)}$ of intravenously administered irinotecan (e.g., Camptosar®) at an amount of about 10-400 mg/m², about 50-400 mg/m², about 100-400 mg/m², about 100 mg/m², about 125 mg/m², about 150 mg/m², about 175 mg/m², about 200 mg/m², about 250 mg/m², about 300 mg/m², or about 350 mg/m² over a period of about 60 minutes once every three weeks, or at an amount of about 50-400 mg/m² (e.g., 125 or 180 mg/m²) over a period of about 60 minutes once every two weeks, or at an amount of about 30-200 mg/m² (e.g., 125 mg/m²) over a period of about 60 minutes twice every week (e.g., for a period of 3 or 4 weeks), as measured by $AUC_{(0\to\infty)}$.

In some embodiments, the $AUC_{(0\to\infty)}$ of the orally administered irinotecan is at least about 30% greater (e.g., at least 30% greater) than the $AUC_{(0\to\infty)}$ of intravenously administered irinotecan (e.g., Camptosar®) at an amount of about 10-400 mg/m², about 50-400 mg/m², about 100-400 mg/m², about 100 mg/m², about 125 mg/m², about 150 mg/m², about 175 mg/m², about 200 mg/m², about 250 mg/m², about 300 mg/m², or about 350 mg/m² over a period of about 60 minutes once every three weeks, or at an amount of about 50-400 mg/m² (e.g., 125 or 180 mg/m²) over a period of about 60 minutes once every two weeks, or at an amount of about 30-200 mg/m² (e.g., 125 mg/m²) over a period of about 60 minutes twice every week (e.g., for a period of 3 or 4 weeks), as measured by $AUC_{(0\to\infty)}$.

In some embodiments, the $AUC_{(0\to\infty)}$ of the orally administered irinotecan is at least about 40% greater (e.g., at least 40% greater) than the $AUC_{(0\to\infty)}$ of intravenously administered irinotecan (e.g., Camptosar®) at an amount of about 10-400 mg/m², about 50-400 mg/m², about 100-400 mg/m², about 100 mg/m², about 125 mg/m², about 150 mg/m², about 175 mg/m², about 200 mg/m², about 250 mg/m², about 300 mg/m², or about 350 mg/m² over a period of about 60 minutes once every three weeks, or at an amount of about 50-400 mg/m² (e.g., 125 or 180 mg/m²) over a period of about 60 minutes once every two weeks, or at an amount of about 30-200 mg/m² (e.g., 125 mg/m²) over a period of about 60 minutes twice every week (e.g., for a period of 3 or 4 weeks), as measured by $AUC_{(0\to\infty)}$.

In some embodiments, the $AUC_{(0\to\infty)}$ of the orally administered irinotecan is at least about 50% greater (e.g., at least 50% greater) than the $AUC_{(0\to\infty)}$ of intravenously administered irinotecan (e.g., Camptosar®) at an amount of about 10-400 mg/m², about 50-400 mg/m², about 100-400 mg/m², about 100 mg/m², about 125 mg/m², about 150 mg/m², about 175 mg/m², about 200 mg/m², about 250 mg/m², about 300 mg/m², or about 350 mg/m² over a period of about 60 minutes once every three weeks, or at an amount of about 50-400 mg/m² (e.g., 125 or 180 mg/m²) over a period of about 60 minutes once every two weeks, or at an amount of about 30-200 mg/m² (e.g., 125 mg/m²) over a period of about 60 minutes twice every week (e.g., for a period of 3 or 4 weeks), as measured by $AUC_{(0\to\infty)}$.

In some embodiments, the $AUC_{(0\to\infty)}$ of the orally administered irinotecan is at least about 60% greater (e.g., at least 60% greater) than the $AUC_{(0\to\infty)}$ of intravenously administered irinotecan (e.g., Camptosar®) at an amount of about 10-400 mg/m², about 50-400 mg/m², about 100-400 mg/m², about 100 mg/m², about 125 mg/m², about 150 mg/m², about 175 mg/m², about 200 mg/m², about 250 mg/m², about 300 mg/m², or about 350 mg/m² over a period of about 60 minutes once every three weeks, or at an amount of about 50-400 mg/m² (e.g., 125 or 180 mg/m²) over a period of about 60 minutes once every two weeks, or at an amount of about 30-200 mg/m² (e.g., 125 mg/m²) over a period of about 60 minutes twice every week (e.g., for a period of 3 or 4 weeks), as measured by $AUC_{(0\to\infty)}$.

In some embodiments, the $AUC_{(0\to\infty)}$ of the orally administered irinotecan is at least about 70% greater (e.g., at least 70% greater) than the $AUC_{(0\to\infty)}$ of intravenously administered irinotecan (e.g., Camptosar®) at an amount of about 10-400 mg/m², about 50-400 mg/m², about 100-400 mg/m², about 100 mg/m², about 125 mg/m², about 150 mg/m², about 175 mg/m², about 200 mg/m², about 250 mg/m², about 300 mg/m², or about 350 mg/m² over a period of about 60 minutes once every three weeks, or at an amount of about 50-400 mg/m² (e.g., 125 or 180 mg/m²) over a period of about 60 minutes once every two weeks, or at an amount of about 30-200 mg/m² (e.g., 125 mg/m²) over a period of about 60 minutes twice every week (e.g., for a period of 3 or 4 weeks), as measured by $AUC_{(0\to\infty)}$.

In some embodiments, the $AUC_{(0\to\infty)}$ of the orally administered irinotecan is at least about 80% greater (e.g., at least 80% greater) than the $AUC_{(0\to\infty)}$ of intravenously administered irinotecan (e.g., Camptosar®) at an amount of about 10-400 mg/m², about 50-400 mg/m², about 100-400 mg/m², about 100 mg/m², about 125 mg/m², about 150 mg/m², about 175 mg/m², about 200 mg/m², about 250 mg/m², about 300 mg/m², or about 350 mg/m² over a period of about 60 minutes once every three weeks, or at an amount of about 50-400 mg/m² (e.g., 125 or 180 mg/m²) over a period of about 60 minutes once every two weeks, or at an amount of about 30-200 mg/m² (e.g., 125 mg/m²) over a period of about 60 minutes twice every week (e.g., for a period of 3 or 4 weeks), as measured by $AUC_{(0\to\infty)}$.

In some embodiments, the $AUC_{(0\to\infty)}$ of the orally administered irinotecan is at least about 90% greater (e.g., at least 90% greater) than the $AUC_{(0\to\infty)}$ of intravenously administered irinotecan (e.g., Camptosar®) at an amount of about 10-400 mg/m², about 50-400 mg/m², about 100-400 mg/m², about 100 mg/m², about 125 mg/m², about 150 mg/m², about 175 mg/m², about 200 mg/m², about 250 mg/m², about 300 mg/m², or about 350 mg/m² over a period of about 60 minutes once every three weeks, or at an amount of about 50-400 mg/m² (e.g., 125 or 180 mg/m²) over a period of about 60 minutes once every two weeks, or at an amount of about 30-200 mg/m² (e.g., 125 mg/m²) over a period of about 60 minutes twice every week (e.g., for a period of 3 or 4 weeks), as measured by $AUC_{(0\to\infty)}$.

In some embodiments, the $AUC_{(0\to\infty)}$ of the orally administered irinotecan is at least about 100% greater (e.g., at least 100% greater) than the $AUC_{(0\to\infty)}$ of intravenously administered irinotecan (e.g., Camptosar®) at an amount of about 10-400 mg/m², about 50-400 mg/m², about 100-400 mg/m², about 100 mg/m², about 125 mg/m², about 150 mg/m², about 175 mg/m², about 200 mg/m², about 250 mg/m², about 300 mg/m², or about 350 mg/m² over a period of about 60 minutes once every three weeks, or at an amount of about 50-400 mg/m² (e.g., 125 or 180 mg/m²) over a period of about 60 minutes once every two weeks, or at an amount of about 30-200 mg/m² (e.g., 125 mg/m²) over a period of about 60 minutes twice every week (e.g., for a period of 3 or 4 weeks), as measured by $AUC_{(0\to\infty)}$.

In some embodiments, the $AUC_{(0\to\infty)}$ of the orally administered irinotecan is about 10% greater to about 100% greater than the $AUC_{(0\to\infty)}$ of intravenously administered irinotecan (e.g., Camptosar®) at an amount of 10-400 mg/m², about 50-400 mg/m², about 100-400 mg/m², about 100 mg/m², about 125 mg/m², about 150 mg/m², about 175 mg/m², about 200 mg/m², about 250 mg/m², about 300 mg/m², or about 350 mg/m² over a period of about 60 minutes once every three weeks, or at an amount of about 50-400 mg/m² (e.g., 125 or 180 mg/m²) over a period of about 60 minutes once every two weeks, or at an amount of about 30-200 mg/m² (e.g., 125 mg/m²) over a period of about 60 minutes twice every week (e.g., for a period of 3 or 4 weeks), as measured by $AUC_{(0\to\infty)}$.

In some embodiments, the $AUC_{(0\to\infty)}$ of the orally administered irinotecan is about 10% greater to about 90% greater than the $AUC_{(0\to\infty)}$ of intravenously administered irinotecan (e.g., Camptosar®) at an amount of about 10-400 mg/m², about 50-400 mg/m², about 100-400 mg/m², about 100 mg/m², about 125 mg/m², about 150 mg/m², about 175 mg/m², about 200 mg/m², about 250 mg/m², about 300 mg/m², or about 350 mg/m² over a period of about 60 minutes once every three weeks, or at an amount of about 50-400 mg/m² (e.g., 125 or 180 mg/m²) over a period of about 60 minutes once every two weeks, or at an amount of about 30-200 mg/m² (e.g., 125 mg/m²) over a period of about 60 minutes twice every week (e.g., for a period of 3 or 4 weeks), as measured by $AUC_{(0\to\infty)}$.

In some embodiments, the $AUC_{(0\to\infty)}$ of the orally administered irinotecan is about 10% greater to about 80% greater than the $AUC_{(0\to\infty)}$ of intravenously administered irinotecan (e.g., Camptosar®) at an amount of about 10-400 mg/m², about 50-400 mg/m², about 100-400 mg/m², about 100 mg/m², about 125 mg/m², about 150 mg/m², about 175 mg/m², about 200 mg/m², about 250 mg/m², about 300 mg/m², or about 350 mg/m² over a period of about 60 minutes once every three weeks, or at an amount of about 50-400 mg/m² (e.g., 125 or 180 mg/m²) over a period of about 60 minutes once every two weeks, or at an amount of about 30-200 mg/m² (e.g., 125 mg/m²) over a period of about 60 minutes twice every week (e.g., for a period of 3 or 4 weeks), as measured by $AUC_{(0\to\infty)}$.

In some embodiments, the $AUC_{(0\to\infty)}$ of the orally administered irinotecan is about 10% greater to about 70% greater than the $AUC_{(0\to\infty)}$ of intravenously administered irinotecan (e.g., Camptosar®) at an amount of about 10-400 mg/m², about 50-400 mg/m², about 100-400 mg/m², about 100 mg/m², about 125 mg/m², about 150 mg/m², about 175 mg/m², about 200 mg/m², about 250 mg/m², about 300 mg/m², or about 350 mg/m² over a period of about 60 minutes once every three weeks, or at an amount of about 50-400 mg/m² (e.g., 125 or 180 mg/m²) over a period of about 60 minutes once every two weeks, or at an amount of about 30-200 mg/m² (e.g., 125 mg/m²) over a period of about 60 minutes twice every week (e.g., for a period of 3 or 4 weeks), as measured by $AUC_{(0\to\infty)}$.

In some embodiments, the $AUC_{(0\to\infty)}$ of the orally administered irinotecan is about 10% greater to about 60% greater than the $AUC_{(0\to\infty)}$ of intravenously administered irinotecan (e.g., Camptosar®) at an amount of about 10-400 mg/m², about 50-400 mg/m², about 100-400 mg/m², about 100 mg/m², about 125 mg/m², about 150 mg/m², about 175 mg/m², about 200 mg/m², about 250 mg/m², about 300 mg/m², or about 350 mg/m² over a period of about 60 minutes once every three weeks, or at an amount of about 50-400 mg/m² (e.g., 125 or 180 mg/m²) over a period of about 60 minutes once every two weeks, or at an amount of about 30-200 mg/m² (e.g., 125 mg/m²) over a period of about 60 minutes twice every week (e.g., for a period of 3 or 4 weeks), as measured by $AUC_{(0\to\infty)}$.

In some embodiments, the $AUC_{(0\to\infty)}$ of the orally administered irinotecan is about 10% greater to about 50% greater than the $AUC_{(0\to\infty)}$ of intravenously administered irinotecan (e.g., Camptosar®) at an amount of about 10-400 mg/m², about 50-400 mg/m², about 100-400 mg/m², about 100 mg/m², about 125 mg/m², about 150 mg/m², about 175 mg/m², about 200 mg/m², about 250 mg/m², about 300 mg/m², or about 350 mg/m² over a period of about 60 minutes once every three weeks, or at an amount of about 50-400 mg/m² (e.g., 125 or 180 mg/m²) over a period of about 60 minutes once every two weeks, or at an amount of about 30-200 mg/m² (e.g., 125 mg/m²) over a period of about 60 minutes twice every week (e.g., for a period of 3 or 4 weeks), as measured by $AUC_{(0\to\infty)}$.

In some embodiments, the $AUC_{(0\to\infty)}$ of the orally administered irinotecan is about 10% greater to about 40% greater than the $AUC_{(0\to\infty)}$ of intravenously administered irinotecan (e.g., Camptosar®) at an amount of about 10-400 mg/m², about 50-400 mg/m², about 100-400 mg/m², about 100 mg/m², about 125 mg/m², about 150 mg/m², about 175 mg/m², about 200 mg/m², about 250 mg/m², about 300 mg/m², or about 350 mg/m² over a period of about 60 minutes once every three weeks, or at an amount of about 50-400 mg/m² (e.g., 125 or 180 mg/m²) over a period of about 60 minutes once every two weeks, or at an amount of about 30-200 mg/m² (e.g., 125 mg/m²) over a period of about 60 minutes twice every week (e.g., for a period of 3 or 4 weeks), as measured by $AUC_{(0\to\infty)}$.

In some embodiments, the $AUC_{(0\to\infty)}$ of the orally administered irinotecan is about 10% greater to about 35% greater than the $AUC_{(0\to\infty)}$ of intravenously administered irinotecan (e.g., Camptosar®) at an amount of about 10-400 mg/m², about 50-400 mg/m², about 100-400 mg/m², about 100 mg/m², about 125 mg/m², about 150 mg/m², about 175 mg/m², about 200 mg/m², about 250 mg/m², about 300 mg/m², or about 350 mg/m² over a period of about 60 minutes once every three weeks, or at an amount of about 50-400 mg/m² (e.g., 125 or 180 mg/m²) over a period of about 60 minutes once every two weeks, or at an amount of about 30-200 mg/m² (e.g., 125 mg/m²) over a period of about 60 minutes twice every week (e.g., for a period of 3 or 4 weeks), as measured by $AUC_{(0\to\infty)}$.

In some embodiments, the $AUC_{(0\to\infty)}$ of the orally administered irinotecan is about 10% greater to about 30% greater than the $AUC_{(0\to\infty)}$ of intravenously administered irinotecan (e.g., Camptosar®) at an amount of about 10-400 mg/m², about 50-400 mg/m², about 100-400 mg/m², about 100 mg/m², about 125 mg/m², about 150 mg/m², about 175 mg/m², about 200 mg/m², about 250 mg/m², about 300 mg/m², or about 350 mg/m² over a period of about 60 minutes once every three weeks, or at an amount of about 50-400 mg/m² (e.g., 125 or 180 mg/m²) over a period of about 60 minutes once every two weeks, or at an amount of about 30-200 mg/m² (e.g., 125 mg/m²) over a period of about 60 minutes twice every week (e.g., for a period of 3 or 4 weeks), as measured by $AUC_{(0\to\infty)}$.

In some embodiments, the $AUC_{(0\to\infty)}$ of the orally administered irinotecan is about 10% greater to about 25% greater than the $AUC_{(0\to\infty)}$ of intravenously administered irinotecan (e.g., Camptosar®) at an amount of about 10-400 mg/m², about 50-400 mg/m², about 100-400 mg/m², about 100 mg/m², about 125 mg/m², about 150 mg/m², about 175 mg/m², about 200 mg/m², about 250 mg/m², about 300 mg/m², or about 350 mg/m² over a period of about 60 minutes once every three weeks, or at an amount of about 50-400 mg/m² (e.g., 125 or 180 mg/m²) over a period of about 60 minutes once every two weeks, or at an amount of about 30-200 mg/m² (e.g., 125 mg/m²) over a period of about 60 minutes twice every week (e.g., for a period of 3 or 4 weeks), as measured by $AUC_{(0\to\infty)}$.

In some embodiments, the $AUC_{(0\to\infty)}$ of the orally administered irinotecan is about 10% greater to about 20% greater than the $AUC_{(0\to\infty)}$ of intravenously administered irinotecan (e.g., Camptosar®) at an amount of about 10-400 mg/m², about 50-400 mg/m², about 100-400 mg/m², about 100 mg/m², about 125 mg/m², about 150 mg/m², about 175 mg/m², about 200 mg/m², about 250 mg/m², about 300 mg/m², or about 350 mg/m² over a period of about 60 minutes once every three weeks, or at an amount of about 50-400 mg/m² (e.g., 125 or 180 mg/m²) over a period of about 60 minutes once every two weeks, or at an amount of about 30-200 mg/m² (e.g., 125 mg/m²) over a period of about 60 minutes twice every week (e.g., for a period of 3 or 4 weeks), as measured by $AUC_{(0\to\infty)}$.

In some embodiments, the $AUC_{(0\to\infty)}$ of the orally administered irinotecan is about 15% greater to about 25% greater than the $AUC_{(0\to\infty)}$ of intravenously administered irinotecan (e.g., Camptosar®) at an amount of about 10-400 mg/m², about 50-400 mg/m², about 100-400 mg/m², about 100 mg/m², about 125 mg/m², about 150 mg/m², about 175 mg/m², about 200 mg/m², about 250 mg/m², about 300 mg/m², or about 350 mg/m² over a period of about 60 minutes once every three weeks, or at an amount of about 50-400 mg/m² (e.g., 125 or 180 mg/m²) over a period of about 60 minutes once every two weeks, or at an amount of about 30-200 mg/m² (e.g., 125 mg/m²) over a period of about 60 minutes twice every week (e.g., for a period of 3 or 4 weeks), as measured by $AUC_{(0\to\infty)}$.

In some embodiments, the $AUC_{(0\to\infty)}$ of the orally administered irinotecan is about 500 ng·h/mL to about 15,000 ng·h/mL.

In some embodiments, the $AUC_{(0\to\infty)}$ of the orally administered irinotecan is about 1,000 ng·h/mL to about 15,000 ng·h/mL.

In some embodiments, the $AUC_{(0\to\infty)}$ of the orally administered irinotecan is about 1,500 ng·h/mL to about 10,000 ng·h/mL.

In some embodiments, the $AUC_{(0\to\infty)}$ of the orally administered irinotecan is about 2,000 ng·h/mL to about 10,000 ng·h/mL.

In some embodiments, the $AUC_{(0\to\infty)}$ of the orally administered irinotecan is about 2,000 ng·h/mL to about 9,000 ng·h/mL.

In some embodiments, the $AUC_{(0\to\infty)}$ of the orally administered irinotecan is about 3,000 ng·h/mL to about 9,000 ng·h/mL.

In some embodiments, the $AUC_{(0\to\infty)}$ of the orally administered irinotecan is about 3,000 ng·h/mL to about 8,000 ng·h/mL.

In some embodiments, the $AUC_{(0\to\infty)}$ of the orally administered irinotecan is about 3,000 ng·h/mL to about 7,000 ng·h/mL.

In some embodiments, the $AUC_{(0\to\infty)}$ of the orally administered irinotecan is about 4,000 ng·h/mL to about 7,000 ng·h/mL.

In some embodiments, the $AUC_{(0\to\infty)}$ of the orally administered irinotecan is about 5,000 ng·h/mL to about 7,000 ng·h/mL.

In some embodiments, the $AUC_{(0\to\infty)}$ of the orally administered irinotecan is about 2,000 ng·h/mL.

In some embodiments, the $AUC_{(0\to\infty)}$ of the orally administered irinotecan is about 3,000 ng·h/mL.

In some embodiments, the $AUC_{(0\to\infty)}$ of the orally administered irinotecan is about 4,000 ng·h/mL.

In some embodiments, the $AUC_{(0\to\infty)}$ of the orally administered irinotecan is about 5,000 ng·h/mL.

In some embodiments, the $AUC_{(0\to\infty)}$ of the orally administered irinotecan is about 6,000 ng·h/mL.

In some embodiments, the $AUC_{(0\to\infty)}$ of the orally administered irinotecan is about 7,000 ng·h/mL.

In some embodiments, the $AUC_{(0\to\infty)}$ of the orally administered irinotecan is about 8,000 ng·h/mL.

In some embodiments, the $AUC_{(0\to\infty)}$ of the orally administered irinotecan is about 9,000 ng·h/mL.

In some embodiments, the $AUC_{(0\to\infty)}$ of the orally administered irinotecan is about 10,000 ng·h/mL.

In some embodiments, the total amount of the irinotecan orally administered per week is about 5 mg/m² to about 3,000 mg/m².

In some embodiments, the total amount of the irinotecan orally administered per week is about 10 mg/m² to about 3,000 mg/m².

In some embodiments, the total amount of the irinotecan orally administered per week is about 15 mg/m² to about 3,000 mg/m².

In some embodiments, the total amount of the irinotecan orally administered per week is about 25 mg/m² to about 2,500 mg/m².

In some embodiments, the total amount of the irinotecan orally administered per week is about 50 mg/m² to about 2,500 mg/m².

In some embodiments, the total amount of the irinotecan orally administered per week is about 75 mg/m² to about 2,500 mg/m².

In some embodiments, the total amount of the irinotecan orally administered per week is about 100 mg/m² to about 2,000 mg/m².

In some embodiments, the total amount of the irinotecan orally administered per week is about 150 mg/m² to about 2,000 mg/m².

In some embodiments, the total amount of the irinotecan orally administered per week is about 200 mg/m² to about 2,000 mg/m².

In some embodiments, the total amount of the irinotecan orally administered per week is about 250 mg/m² to about 2,000 mg/m².

In some embodiments, the total amount of the irinotecan orally administered per week is about 300 mg/m² to about 2,000 mg/m².

In some embodiments, the total amount of the irinotecan orally administered per week is about 300 mg/m² to about 1,900 mg/m².

In some embodiments, the total amount of the irinotecan orally administered per week is about 300 mg/m² to about 1,800 mg/m².

In some embodiments, the total amount of the irinotecan orally administered per week is about 300 mg/m² to about 1,700 mg/m².

In some embodiments, the total amount of the irinotecan orally administered per week is about 300 mg/m² to about 1,600 mg/m².

In some embodiments, the total amount of the irinotecan orally administered per week is about 300 mg/m² to about 1,500 mg/m².

In some embodiments, the total amount of the irinotecan orally administered per week is about 300 mg/m² to about 1,400 mg/m².

In some embodiments, the total amount of the irinotecan orally administered per week is about 300 mg/m² to about 1,300 mg/m².

In some embodiments, the total amount of the irinotecan orally administered per week is about 300 mg/m² to about 1,200 mg/m².

In some embodiments, the total amount of the irinotecan orally administered per week is about 300 mg/m² to about 1,100 mg/m².

In some embodiments, the total amount of the irinotecan orally administered per week is about 300 mg/m² to about 1,000 mg/m².

In some embodiments, the total amount of the irinotecan orally administered per week is about 300 mg/m² to about 900 mg/m².

In some embodiments, the total amount of the irinotecan orally administered per week is about 350 mg/m² to about 850 mg/m².

In some embodiments, the total amount of the irinotecan orally administered per week is about 400 mg/m² to about 800 mg/m².

In some embodiments, the total amount of the irinotecan orally administered per week is about 450 mg/m² to about 750 mg/m².

In some embodiments, the total amount of the irinotecan orally administered per week is about 500 mg/m² to about 700 mg/m².

In some embodiments, the total amount of the irinotecan orally administered per week is about 550 mg/m² to about 650 mg/m².

In some embodiments, the total amount of the irinotecan orally administered per week is about 15, 25, 50, 75, 100, 150, 200, 250, 300, 325, 350, 375, 400, 425, 450, 475, 500, 525, 550, 575, 600, 605, 610, 615, 620, 625, 630, 635, 640, 645, 650, 655, 660, 665, 670, 675, 680, 685, 690, 695, 700, 725, 750, 775, 800, 825, 850, 875, 900, 925, 950, 975, 1,000, 1,025, 1,050, 1,075, 1,100, 1,125, 1,150, 1,175, 1,200, 1,225, 1,250, 1,275, 1,300, 1,325, 1,350, 1,375, 1,400, 1,425, 1,450, 1,475, 1,500, 1,525, 1,550, 1,575, 1,600, 1,625, 1,650, 1,675, 1,700, 1,725, 1,750, 1,775, or 1,800 mg/m².

In some embodiments, the total amount of the irinotecan orally administered per week is at least about 5 mg/m² (e.g., at least 5 mg/m²).

In some embodiments, the total amount of the irinotecan orally administered per week is at least about 10 mg/m² (e.g., at least 10 mg/m²).

In some embodiments, the total amount of the irinotecan orally administered per week is at least about 15 mg/m² (e.g., at least 15 mg/m²).

In some embodiments, the total amount of the irinotecan orally administered per week is at least about 20 mg/m² (e.g., at least 20 mg/m²).

In some embodiments, the total amount of the irinotecan orally administered per week is at least about 25 mg/m² (e.g., at least 25 mg/m²).

In some embodiments, the total amount of the irinotecan orally administered per week is at least about 50 mg/m² (e.g., at least 50 mg/m²).

In some embodiments, the total amount of the irinotecan orally administered per week is at least about 75 mg/m² (e.g., at least 75 mg/m²).

In some embodiments, the total amount of the irinotecan orally administered per week is at least about 100 mg/m² (e.g., at least 100 mg/m²).

In some embodiments, the total amount of the irinotecan orally administered per week is at least about 125 mg/m² (e.g., at least 125 mg/m²).

In some embodiments, the total amount of the irinotecan orally administered per week is at least about 150 mg/m² (e.g., at least 150 mg/m²).

In some embodiments, the total amount of the irinotecan orally administered per week is at least about 175 mg/m² (e.g., at least 175 mg/m²).

In some embodiments, the total amount of the irinotecan orally administered per week is at least about 200 mg/m² (e.g., at least 200 mg/m²).

In some embodiments, the total amount of the irinotecan orally administered per week is at least about 225 mg/m² (e.g., at least 225 mg/m²).

In some embodiments, the total amount of the irinotecan orally administered per week is at least about 250 mg/m² (e.g., at least 250 mg/m²).

In some embodiments, the total amount of the irinotecan orally administered per week is at least about 275 mg/m² (e.g., at least 275 mg/m²).

In some embodiments, the total amount of the irinotecan orally administered per week is at least about 300 mg/m² (e.g., at least 300 mg/m²).

In some embodiments, the total amount of the irinotecan orally administered per week is at least about 325 mg/m² (e.g., at least 325 mg/m²).

In some embodiments, the total amount of the irinotecan orally administered per week is at least about 350 mg/m² (e.g., at least 350 mg/m²).

In some embodiments, the total amount of the irinotecan orally administered per week is at least about 375 mg/m² (e.g., at least 375 mg/m²).

In some embodiments, the total amount of the irinotecan orally administered per week is at least about 400 mg/m² (e.g., at least 400 mg/m²).

In some embodiments, the total amount of the irinotecan orally administered per week is at least about 425 mg/m² (e.g., at least 425 mg/m²).

In some embodiments, the total amount of the irinotecan orally administered per week is at least about 450 mg/m² (e.g., at least 450 mg/m²).

In some embodiments, the total amount of the irinotecan orally administered per week is at least about 475 mg/m² (e.g., at least 475 mg/m²).

In some embodiments, the total amount of the irinotecan orally administered per week is at least about 500 mg/m² (e.g., at least 500 mg/m²).

In some embodiments, the total amount of the irinotecan orally administered per week is at least about 525 mg/m² (e.g., at least 525 mg/m²).

In some embodiments, the total amount of the irinotecan orally administered per week is at least about 550 mg/m² (e.g., at least 550 mg/m²).

In some embodiments, the total amount of the irinotecan orally administered per week is at least about 575 mg/m² (e.g., at least 575 mg/m²).

In some embodiments, the total amount of the irinotecan orally administered per week is at least about 600 mg/m² (e.g., at least 600 mg/m²).

In some embodiments, the total amount of the irinotecan orally administered per week is at least about 615 mg/m² (e.g., at least 615 mg/m²).

In some embodiments, the total amount of the irinotecan orally administered per week is at least about 625 mg/m² (e.g., at least 625 mg/m²).

In some embodiments, the total amount of the irinotecan orally administered per week is at least about 630 mg/m² (e.g., at least 630 mg/m²).

In some embodiments, the total amount of the irinotecan orally administered per week is at least about 645 mg/m² (e.g., at least 645 mg/m²).

In some embodiments, the total amount of the irinotecan orally administered per week is at least about 650 mg/m² (e.g., at least 650 mg/m²).

In some embodiments, the total amount of the irinotecan orally administered per week is at least about 655 mg/m² (e.g., at least 655 mg/m²).

In some embodiments, the total amount of the irinotecan orally administered per week is at least about 660 mg/m² (e.g., at least 660 mg/m²).

In some embodiments, the total amount of the irinotecan orally administered per week is at least about 675 mg/m² (e.g., at least 675 mg/m²).

In some embodiments, the total amount of the irinotecan orally administered per week is at least about 700 mg/m² (e.g., at least 700 mg/m²).

In some embodiments, the total amount of the irinotecan orally administered per week is at least about 725 mg/m² (e.g., at least 725 mg/m²).

In some embodiments, the total amount of the irinotecan orally administered per week is at least about 750 mg/m² (e.g., at least 750 mg/m²).

In some embodiments, the total amount of the irinotecan orally administered per week is at least about 775 mg/m² (e.g., at least 775 mg/m²).

In some embodiments, the total amount of the irinotecan orally administered per week is at least about 800 mg/m² (e.g., at least 800 mg/m²).

In some embodiments, the total amount of the irinotecan orally administered per week is at least about 825 mg/m² (e.g., at least 825 mg/m²).

In some embodiments, the total amount of the irinotecan orally administered per week is at least about 850 mg/m² (e.g., at least 850 mg/m²).

In some embodiments, the total amount of the irinotecan orally administered per week is at least about 875 mg/m² (e.g., at least 875 mg/m²).

In some embodiments, the total amount of the irinotecan orally administered per week is at least about 900 mg/m² (e.g., at least 900 mg/m²).

In some embodiments, the total amount of the irinotecan orally administered per week is at least about 925 mg/m² (e.g., at least 925 mg/m²).

In some embodiments, the total amount of the irinotecan orally administered per week is at least about 950 mg/m² (e.g., at least 950 mg/m²).

In some embodiments, the total amount of the irinotecan orally administered per week is at least about 975 mg/m² (e.g., at least 975 mg/m²).

In some embodiments, the total amount of the irinotecan orally administered per week is at least about 1,000 mg/m² (e.g., at least 1,000 mg/m²).

In some embodiments, the total amount of the irinotecan orally administered per week is at least about 1,050 mg/m² (e.g., at least 1,050 mg/m²).

In some embodiments, the total amount of the irinotecan orally administered per week is at least about 1,100 mg/m² (e.g., at least 1,100 mg/m²).

In some embodiments, the total amount of the irinotecan orally administered per week is at least about 1,125 mg/m² (e.g., at least 1,125 mg/m²).

In some embodiments, the total amount of the irinotecan orally administered per week is at least about 1,200 mg/m² (e.g., at least 1,200 mg/m²).

In some embodiments, the total amount of the irinotecan orally administered per week is at least about 1,250 mg/m² (e.g., at least 1,250 mg/m²).

In some embodiments, the total amount of the irinotecan orally administered per week is at least about 1,300 mg/m² (e.g., at least 1,300 mg/m²).

In some embodiments, the total amount of the irinotecan orally administered per week is at least about 1,350 mg/m² (e.g., at least 1,350 mg/m²).

In some embodiments, the total amount of the irinotecan orally administered per week is at least about 1,375 mg/m² (e.g., at least 1,375 mg/m²).

In some embodiments, the total amount of the irinotecan orally administered per week is at least about 1,400 mg/m² (e.g., at least 1,400 mg/m²).

In some embodiments, the total amount of the irinotecan orally administered per week is at least about 1,500 mg/m² (e.g., at least 1,500 mg/m²).

In some embodiments, the total amount of the irinotecan orally administered per week is at least about 1,625 mg/m² (e.g., at least 1,625 mg/m²).

In some embodiments, the total amount of the irinotecan orally administered per week is at least about 1,650 mg/m² (e.g., at least 1,650 mg/m²).

In some embodiments, the total amount of the irinotecan orally administered per week is at least about 1,750 mg/m² (e.g., at least 1,750 mg/m²).

In some embodiments, the total amount of the irinotecan orally administered per week is at least about 1,800 mg/m$^2$ (e.g., at least 1,800 mg/m$^2$).

In some embodiments, the AUC$_{(0\to\infty)}$ of the orally administered irinotecan is equal to or greater than the AUC$_{(0\to\infty)}$ of intravenously administered irinotecan (e.g., Camptosar®) at an amount of about 50-400 mg/m$^2$ (e.g., 350 mg/m$^2$) over a period of about 60 minutes once every three weeks, or at an amount of about 50-400 mg/m$^2$ (e.g., 125 or 180 mg/m$^2$) over a period of about 60 minutes once every two weeks, or at an amount of about 30-200 mg/m$^2$ (e.g., 125 mg/m$^2$) over a period of about 60 minutes twice every week (e.g., for a period of 3 or 4 weeks) in treating cancer.

In some embodiments, the AUC$_{(0\to\infty)}$ of the orally administered irinotecan is equal to or greater than the AUC$_{(0\to\infty)}$ of intravenously administered irinotecan (e.g., Camptosar®) at an amount of about 70-90 mg/m$^2$ over a period of about 60 minutes once every three weeks in treating cancer.

In some embodiments, the AUC$_{(0\to\infty)}$ of the orally administered irinotecan is equal to or greater than the AUC$_{(0\to\infty)}$ of intravenously administered irinotecan (e.g., Camptosar®) at an amount of about 75-85 mg/m$^2$ over a period of about 60 minutes once every three weeks in treating cancer.

In some embodiments, the AUC$_{(0\to\infty)}$ of the orally administered irinotecan is equal to or greater than the AUC$_{(0\to\infty)}$ of intravenously administered irinotecan (e.g., Camptosar®) at an amount of about 80 mg/m$^2$ over a period of about 60 minutes once every three weeks in treating cancer.

In some embodiments, the AUC$_{(0\to\infty)}$ of the orally administered irinotecan is equal to or greater than the AUC$_{(0\to\infty)}$ of intravenously administered irinotecan (e.g., Camptosar®) at an amount of about 75 mg/m$^2$ over a period of about 60 minutes once every three weeks in treating cancer.

In some embodiments, the present disclosure provides methods of treating cancer in a subject, and/or to methods for reducing or preventing toxicity, hypersensitivity-type infusion reactions and other negative outcomes resulting from or associated with intravenously administered irinotecan (e.g., Camptosar®) therapy in a subject suffering from cancer.

In some embodiments, the present disclosure provides Compound A for use with irinotecan in the treatment of cancer in a subject, and/or to Compound A for use with irinotecan in the reducing or preventing toxicity, hypersensitivity-type infusion reactions and other negative outcomes resulting from or associated with intravenously administered irinotecan (e.g., Camptosar®) therapy in a subject suffering from cancer.

In some embodiments, the present disclosure provides use of Compound A in the manufacture of a medicament for use with irinotecan for the treatment of cancer in a subject, and/or to use of Compound A in the manufacture of a medicament for use with irinotecan for the reducing or preventing toxicity, hypersensitivity-type infusion reactions and other negative outcomes resulting from or associated with intravenously administered irinotecan (e.g., Camptosar®) therapy in a subject suffering from cancer.

In some embodiments, the present disclosure provides use of Compound A with irinotecan for the treatment of cancer in a subject, and/or for reducing or preventing toxicity, hypersensitivity-type infusion reactions and other negative outcomes resulting from or associated with intravenously administered irinotecan (e.g., Camptosar®) therapy in a subject suffering from cancer.

In some embodiments, the present disclosure provides use of Compound A in a combination therapy with irinotecan for the treatment of cancer in a subject, and/or to use of Compound A in a combination therapy with irinotecan for the reducing or preventing toxicity, hypersensitivity-type infusion reactions and other negative outcomes resulting from or associated with intravenously administered irinotecan (e.g., Camptosar®) therapy in a subject suffering from cancer.

In some embodiments, the present disclosure provides use of a medicament in a combination therapy with irinotecan for the treatment of cancer in a subject, and/or to use of a medicament in a combination therapy with irinotecan for the reducing or preventing toxicity, hypersensitivity-type infusion reactions and other negative outcomes resulting from or associated with intravenously administered irinotecan (e.g., Camptosar®) therapy in a subject suffering from cancer, wherein the medicament comprises Compound A.

In some embodiments, the cancer is a disease that involves abnormal cell growth with the potential to invade or spread to other parts of the body.

In some embodiments, the cancer is a malignant tumor or neoplasm.

In some embodiments, the cancer is breast cancer, pancreatic cancer, non-small cell lung cancer, ovarian cancer, AIDS-related Kaposi sarcoma, esophageal cancer, melanoma, lymphoma, uterine cancer, peritoneal cancer, fallopian tube cancer, endometrial cancer, cervical cancer, thyroid cancer, gastric cancer, gastroesophageal junction cancer, urothelial cancer, bladder cancer, oropharynx cancer, hypopharynx cancer, larynx cancer, head and neck cancer, germ cell cancer/tumors, prostate cancer, colon cancer, rectal cancer, kidney cancer, cholangiocarcinoma (bile duct cancer), glioblastoma, leukemia, and non-Hodgkin lymphoma.

In some embodiments, the cancer is breast cancer, pancreatic cancer, non-small cell lung cancer, ovarian cancer, AIDS-related Kaposi sarcoma, soft tissue sarcoma, esophageal cancer, melanoma, lymphoma, uterine cancer, peritoneal cancer, fallopian tube cancer, endometrial cancer, cervical cancer, thyroid cancer, gastric cancer, gastroesophageal junction cancer, urothelial cancer, bladder cancer, oropharynx cancer, hypopharynx cancer, larynx cancer, head and neck cancer, germ cell cancer/tumors, prostate cancer, colon cancer, rectal cancer, kidney cancer, squamous cell carcinoma, leukemia, or non-Hodgkin lymphoma.

In some embodiments, the cancer is breast cancer, pancreatic cancer, non-small cell lung cancer, ovarian cancer, AIDS-related Kaposi sarcoma, esophageal cancer, melanoma, lymphoma, uterine cancer, peritoneal cancer, fallopian tube cancer, endometrial cancer, cervical cancer, thyroid cancer, gastric cancer, gastroesophageal junction cancer, urothelial cancer, bladder cancer, oropharynx cancer, hypopharynx cancer, larynx cancer, head and neck cancer, or germ cell cancer/tumors.

In some embodiments, the cancer is breast cancer, non-small cell lung cancer, ovarian cancer, AIDS-related Kaposi sarcoma, esophageal cancer, bladder cancer, prostate cancer, or melanoma.

In some embodiments, the cancer is breast cancer, non-small cell lung cancer, ovarian cancer, or AIDS-related Kaposi sarcoma.

In some embodiments, the cancer is breast cancer. In some embodiments, the breast cancer is metastatic breast cancer. In some embodiments, the breast cancer is carcinoma of the breast.

In some embodiments, the cancer is lung cancer. In some embodiments, the lung cancer is non-small cell lung cancer.

In some embodiments, the cancer is prostate cancer. In some embodiments, the prostate cancer is metastatic hormone resistant prostate cancer, castration naïve prostate cancer, or castration resistant prostate cancer. In some embodiments, the prostate cancer is metastatic hormone resistant prostate cancer. In some embodiments, the prostate cancer is carcinoma of the prostate.

In some embodiments, the cancer is ovarian cancer. In some embodiments, the cancer is carcinoma of the ovary.

In some embodiments, the cancer is AIDS-related Kaposi sarcoma.

In some embodiments, the cancer is pancreatic cancer. In some embodiments, the pancreatic cancer is adenocarcinoma of the pancreas.

In some embodiments, the cancer is bladder cancer, breast cancer, cervical cancer, esophageal cancer, gastric cancer, epithelial ovarian cancer, fallopian tube cancer, primary peritoneal cancer, head and neck cancer, squamous cell carcinoma of the head and neck (SCCHN), non-small cell lung cancer (NSCLC), castration naïve prostate cancer, castration resistant prostate cancer, metastatic hormone resistant prostate cancer (mHRPC), small cell lung cancer, soft tissue sarcoma, or uterine cancer.

In some embodiments, the cancer is breast cancer, non-small cell lung cancer, prostate cancer (including metastatic hormone resistant prostate cancer, castration naïve prostate cancer, or castration resistant prostate cancer), squamous cell carcinoma of the head and neck, or gastric cancer.

In some embodiments, the cancer is bladder cancer, cervical cancer, ovarian cancer, epithelial ovarian cancer, fallopian tube cancer, peritoneal cancer, esophageal cancer, soft tissue sarcoma, leiomyosarcoma, uterine cancer, pancreatic cancer, or endometrial cancer.

In some embodiments, the cancer is an acute leukemia, glioma, or lymphoma.

In some embodiments the cancer is cervical cancer, ovarian cancer (resistant or refractory), esophagus cancer, lung cancer (small cell or non-small cell), or gastric cancer.

In some embodiments, the cancer is colorectal cancer.

In some embodiments, the cancer is an advanced malignancy. In some embodiments, the cancer is a primary or secondary cancer.

In some embodiments, the cancer is an irinotecan-responsive cancer.

In some embodiments, the cancer is a solid tumor.

In some embodiments, the solid tumor is histologically or cytologically confirmed.

In some embodiments, the solid tumor is metastatic or unresectable.

In some embodiments, the methods of the present disclosure include a method for treating colorectal cancer in a subject in need thereof, wherein the plasma exposure of the orally administered irinotecan, as measured by $AUC_{(0 \to \infty)}$, is equal to or greater than the plasma exposure, as measured by $AUC_{(0 \to \infty)}$, of intravenously administered irinotecan (e.g., Camptosar®) at an amount of about 50-400 mg/m$^2$ (e.g., 350 mg/m$^2$) over a period of about 1 to 24 hours once every three weeks.

In some embodiments, the methods of the present disclosure include a method for treating colorectal cancer in a subject in need thereof, wherein the plasma exposure of the orally administered irinotecan, as measured by $AUC_{(0 \to \infty)}$, is equal to or greater than the plasma exposure, as measured by $AUC_{(0 \to \infty)}$, of intravenously administered irinotecan (e.g., Camptosar®) at an amount of about 10-400 mg/m$^2$, about 50-400 mg/m$^2$, about 100-400 mg/m$^2$, about 100 mg/m$^2$, about 125 mg/m$^2$, about 150 mg/m$^2$, about 175 mg/m$^2$, about 200 mg/m$^2$, about 250 mg/m$^2$, about 300 mg/m$^2$, or about 350 mg/m$^2$ over a period of about 1 to 24 hours, about 1 to 20 hours, about 1-16 hours, about 2-12 hours, or about 3-8 hours once every three weeks.

In some embodiments, the methods of the present disclosure include a method for treating colorectal cancer in a subject in need thereof, wherein the plasma exposure of the orally administered irinotecan, as measured by $AUC_{(0 \to \infty)}$, is equal to or greater than the plasma exposure, as measured by $AUC_{(0 \to \infty)}$, of intravenously administered irinotecan (e.g., Camptosar®) at an amount of about 50-400 mg/m$^2$ (e.g., 350 mg/m$^2$) over a period of about 1 to 24 hours once every three weeks.

In some embodiments, the methods of the present disclosure include a method for treating colorectal cancer in a subject in need thereof, wherein the plasma exposure of the orally administered irinotecan, as measured by $AUC_{(0 \to \infty)}$, is equal to or greater than the plasma exposure, as measured by $AUC_{(0 \to \infty)}$, of intravenously administered irinotecan (e.g., Camptosar®) at an amount of about 10-400 mg/m$^2$, about 50-400 mg/m$^2$, about 100-400 mg/m$^2$, about 100 mg/m$^2$, about 125 mg/m$^2$, about 150 mg/m$^2$, about 175 mg/m$^2$, about 200 mg/m$^2$, about 250 mg/m$^2$, about 300 mg/m$^2$, or about 350 mg/m$^2$ over a period of about 1 to 24 hours, about 1 to 20 hours, about 1-16 hours, about 2-12 hours, or about 3-8 hours once every three weeks.

In some embodiments, the methods of the present disclosure include a method for treating metastatic breast cancer in a subject in need thereof, wherein the plasma exposure of the orally administered irinotecan, as measured by $AUC_{(0 \to \infty)}$, is equal to or greater than the plasma exposure, as measured by $AUC_{(0 \to \infty)}$, of intravenously administered irinotecan (e.g., Camptosar®) at an amount of about 50-400 mg/m$^2$ (e.g., 350 mg/m$^2$) over a period of about 1 to 24 hours once every three weeks.

In some embodiments, the methods of the present disclosure include a method for treating metastatic breast cancer in a subject in need thereof, wherein the plasma exposure of the orally administered irinotecan, as measured by $AUC_{(0 \to \infty)}$, is equal to or greater than the plasma exposure, as measured by $AUC_{(0 \to \infty)}$, of intravenously administered irinotecan (e.g., Camptosar®) at an amount of about 10-400 mg/m$^2$, about 50-400 mg/m$^2$, about 100-400 mg/m$^2$, about 100 mg/m$^2$, about 125 mg/m$^2$, about 150 mg/m$^2$, about 175 mg/m$^2$, about 200 mg/m$^2$, about 250 mg/m$^2$, about 300 mg/m$^2$, or about 350 mg/m$^2$ over a period of about 1 to 24 hours, about 1 to 20 hours, about 1-16 hours, about 2-12 hours, or about 3-8 hours once every three weeks.

In some embodiments, the methods of the present disclosure include a method for treating non-small cell lung cancer in a subject in need thereof, wherein the plasma exposure of the orally administered irinotecan, as measured by $AUC_{(0 \to \infty)}$, is equal to or greater than the plasma exposure, as measured by $AUC_{(0 \to \infty)}$, of intravenously administered irinotecan (e.g., Camptosar®) at an amount of about 50-400 mg/m$^2$ (e.g., 350 mg/m$^2$) over a period of about 1 to 24 hours once every three weeks.

In some embodiments, the methods of the present disclosure include a method for treating non-small cell lung cancer in a subject in need thereof, wherein the plasma exposure of the orally administered irinotecan, as measured by $AUC_{(0 \to \infty)}$, is equal to or greater than the plasma exposure, as measured by $AUC_{(0 \to \infty)}$, of intravenously administered irinotecan (e.g., Camptosar®) at an amount of about 10-400 mg/m$^2$, about 50-400 mg/m$^2$, about 100-400 mg/m$^2$, about 100 mg/m$^2$, about 125 mg/m$^2$, about 150 mg/m$^2$, about 175 mg/m$^2$, about 200 mg/m$^2$, about 250 mg/m$^2$, about 300 mg/m$^2$, or about 350 mg/m$^2$ over a period of about 1 to 24 hours, about 1 to 20 hours, about 1-16 hours, about 2-12 hours, or about 3-8 hours once every three weeks.

In some embodiments, the methods of the present disclosure include a method for treating prostate cancer (e.g., metastatic hormone resistant prostate cancer, castration naïve prostate cancer, or castration resistant prostate cancer) in a subject in need thereof, wherein the plasma exposure of the orally administered irinotecan, as measured by $AUC_{(0 \to \infty)}$, is equal to or greater than the plasma exposure, as measured by $AUC_{(0 \to \infty)}$, of intravenously administered irinotecan (e.g., Camptosar®) at an amount of about 50-400 mg/m² (e.g., 350 mg/m²) over a period of about 1 to 24 hours once every three weeks.

In some embodiments, the methods of the present disclosure include a method for treating prostate cancer (e.g., metastatic hormone resistant prostate cancer, castration naïve prostate cancer, or castration resistant prostate cancer) in a subject in need thereof, wherein the plasma exposure of the orally administered irinotecan, as measured by $AUC_{(0 \to \infty)}$, is equal to or greater than the plasma exposure, as measured by $AUC_{(0 \to \infty)}$, of intravenously administered irinotecan (e.g., Camptosar®) at an amount of about 10-400 mg/m², about 50-400 mg/m², about 100-400 mg/m², about 100 mg/m², about 125 mg/m², about 150 mg/m², about 175 mg/m², about 200 mg/m², about 250 mg/m², about 300 mg/m², or about 350 mg/m² over a period of about 1 to 24 hours, about 1 to 20 hours, about 1-16 hours, about 2-12 hours, or about 3-8 hours once every three weeks.

In some embodiments, the methods of the present disclosure include a method for treating adenocarcinoma of the pancreas in a subject in need thereof, wherein the plasma exposure of the orally administered irinotecan, as measured by $AUC_{(0 \to \infty)}$, is equal to or greater than the plasma exposure, as measured by $AUC_{(0 \to \infty)}$, of intravenously administered irinotecan (e.g., Camptosar®) at an amount of about 50-400 mg/m² (e.g., 350 mg/m²) over a period of about 1 to 24 hours once every three weeks.

In some embodiments, the methods of the present disclosure include a method for treating adenocarcinoma of the pancreas in a subject in need thereof, wherein the plasma exposure of the orally administered irinotecan, as measured by $AUC_{(0 \to \infty)}$, is equal to or greater than the plasma exposure, as measured by $AUC_{(0 \to \infty)}$, of intravenously administered irinotecan (e.g., Camptosar®) at an amount of about 10-400 mg/m², about 50-400 mg/m², about 100-400 mg/m², about 100 mg/m², about 125 mg/m², about 150 mg/m², about 175 mg/m², about 200 mg/m², about 250 mg/m², about 300 mg/m², or about 350 mg/m² over a period of about 1 to 24 hours, about 1 to 20 hours, about 1-16 hours, about 2-12 hours, or about 3-8 hours once every three weeks.

In some embodiments, the methods of the present disclosure include a method for treating carcinoma of the ovary in a subject in need thereof, wherein the plasma exposure of the orally administered irinotecan, as measured by $AUC_{(0 \to \infty)}$, is equal to or greater than the plasma exposure, as measured by $AUC_{(0 \to \infty)}$, of intravenously administered irinotecan (e.g., Camptosar®) at an amount of about 50-400 mg/m² (e.g., 350 mg/m²) over a period of about 1 to 24 hours once every three weeks.

In some embodiments, the methods of the present disclosure include a method for treating carcinoma of the ovary in a subject in need thereof, wherein the plasma exposure of the orally administered irinotecan, as measured by $AUC_{(0 \to \infty)}$, is equal to or greater than the plasma exposure, as measured by $AUC_{(0 \to \infty)}$, of intravenously administered irinotecan (e.g., Camptosar®) at an amount of about 10-400 mg/m², about 50-400 mg/m², about 100-400 mg/m², about 100 mg/m², about 125 mg/m², about 150 mg/m², about 175 mg/m², about 200 mg/m², about 250 mg/m², about 300 mg/m², or about 350 mg/m² over a period of about 1 to 24 hours, about 1 to 20 hours, about 1-16 hours, about 2-12 hours, or about 3-8 hours once every three weeks.

In some embodiments, the methods of the present disclosure include a method for treating carcinoma of the colon in a subject in need thereof, wherein the plasma exposure of the orally administered irinotecan, as measured by $AUC_{(0 \to \infty)}$, is equal to or greater than the plasma exposure, as measured by $AUC_{(0 \to \infty)}$, of intravenously administered irinotecan (e.g., Camptosar®) at an amount of about 50-400 mg/m² (e.g., 350 mg/m²) over a period of about 1 to 24 hours once every three weeks.

In some embodiments, the methods of the present disclosure include a method for treating carcinoma of the colon in a subject in need thereof, wherein the plasma exposure of the orally administered irinotecan, as measured by $AUC_{(0 \to \infty)}$, is equal to or greater than the plasma exposure, as measured by $AUC_{(0 \to \infty)}$, of intravenously administered irinotecan (e.g., Camptosar®) at an amount of about 10-400 mg/m², about 50-400 mg/m², about 100-400 mg/m², about 100 mg/m², about 125 mg/m², about 150 mg/m², about 175 mg/m², about 200 mg/m², about 250 mg/m², about 300 mg/m², or about 350 mg/m² over a period of about 1 to 24 hours, about 1 to 20 hours, about 1-16 hours, about 2-12 hours, or about 3-8 hours once every three weeks.

In some embodiments, the methods of the present disclosure include a method for treating carcinoma of the breast in a subject in need thereof, wherein the plasma exposure of the orally administered irinotecan, as measured by $AUC_{(0 \to \infty)}$, is equal to or greater than the plasma exposure, as measured by $AUC_{(0 \to \infty)}$, of intravenously administered irinotecan (e.g., Camptosar®) at an amount of about 50-400 mg/m² (e.g., 350 mg/m²) over a period of about 1 to 24 hours once every three weeks.

In some embodiments, the methods of the present disclosure include a method for treating carcinoma of the breast in a subject in need thereof, wherein the plasma exposure of the orally administered irinotecan, as measured by $AUC_{(0 \to \infty)}$, is equal to or greater than the plasma exposure, as measured by $AUC_{(0 \to \infty)}$, of intravenously administered irinotecan (e.g., Camptosar®) at an amount of about 10-400 mg/m², about 50-400 mg/m², about 100-400 mg/m², about 100 mg/m², about 125 mg/m², about 150 mg/m², about 175 mg/m², about 200 mg/m², about 250 mg/m², about 300 mg/m², or about 350 mg/m² over a period of about 1 to 24 hours, about 1 to 20 hours, about 1-16 hours, about 2-12 hours, or about 3-8 hours once every three weeks.

In some embodiments, the methods of the present disclosure include a method for treating AIDS-related Kaposi's Sarcoma in a subject in need thereof, wherein the plasma exposure of the orally administered irinotecan, as measured by $AUC_{(0 \to \infty)}$, is equal to or greater than the plasma exposure, as measured by $AUC_{(0 \to \infty)}$, of intravenously administered irinotecan (e.g., Camptosar®) at an amount of about 50-400 mg/m² (e.g., 350 mg/m²) over a period of about 1 to 24 hours once every three weeks.

In some embodiments, the methods of the present disclosure include a method for treating AIDS-related Kaposi's Sarcoma in a subject in need thereof, wherein the plasma exposure of the orally administered irinotecan, as measured by $AUC_{(0 \to \infty)}$, is equal to or greater than the plasma exposure, as measured by $AUC_{(0 \to \infty)}$, of intravenously administered irinotecan (e.g., Camptosar®) at an amount of about 10-400 mg/m², about 50-400 mg/m², about 100-400 mg/m², about 100 mg/m², about 125 mg/m², about 150 mg/m², about 175 mg/m$^2$, about 200 mg/m$^2$, about 250 mg/m$^2$, about 300 mg/m$^2$, or about 350 mg/m$^2$ over a period of about 1 to 24 hours, about 1 to 20 hours, about 1-16 hours, about 2-12 hours, or about 3-8 hours once every three weeks.

In some embodiments, the present disclosure provides Compound A for use with irinotecan in treating colorectal cancer in a subject in need thereof, wherein the plasma exposure of the orally administered irinotecan, as measured by $AUC_{(0\to\infty)}$, is equal to or greater than the plasma exposure, as measured by $AUC_{(0\to\infty)}$, of intravenously administered irinotecan (e.g., Camptosar®) at an amount of about 50-400 mg/m$^2$ (e.g., 350 mg/m$^2$) over a period of about 1 to 24 hours once every three weeks.

In some embodiments, the present disclosure provides Compound A for use with irinotecan in treating colorectal cancer in a subject in need thereof, wherein the plasma exposure of the orally administered irinotecan, as measured by $AUC_{(0\to\infty)}$, is equal to or greater than the plasma exposure, as measured by $AUC_{(0\to\infty)}$, of intravenously administered irinotecan (e.g., Camptosar®) at an amount of about 10-400 mg/m$^2$, about 50-400 mg/m$^2$, about 100-400 mg/m$^2$, about 100 mg/m$^2$, about 125 mg/m$^2$, about 150 mg/m$^2$, about 175 mg/m$^2$, about 200 mg/m$^2$, about 250 mg/m$^2$, about 300 mg/m$^2$, or about 350 mg/m$^2$ over a period of about 1 to 24 hours, about 1 to 20 hours, about 1-16 hours, about 2-12 hours, or about 3-8 hours once every three weeks.

In some embodiments, the present disclosure provides Compound A for use with irinotecan in treating colorectal cancer in a subject in need thereof, wherein the plasma exposure of the orally administered irinotecan, as measured by $AUC_{(0\to\infty)}$, is equal to or greater than the plasma exposure, as measured by $AUC_{(0\to\infty)}$, of intravenously administered irinotecan (e.g., Camptosar®) at an amount of about 50-400 mg/m$^2$ (e.g., 350 mg/m$^2$) over a period of about 1 to 24 hours once every three weeks.

In some embodiments, the present disclosure provides Compound A for use with irinotecan in treating colorectal cancer in a subject in need thereof, wherein the plasma exposure of the orally administered irinotecan, as measured by $AUC_{(0\to\infty)}$, is equal to or greater than the plasma exposure, as measured by $AUC_{(0\to\infty)}$, of intravenously administered irinotecan (e.g., Camptosar®) at an amount of about 10-400 mg/m$^2$, about 50-400 mg/m$^2$, about 100-400 mg/m$^2$, about 100 mg/m$^2$, about 125 mg/m$^2$, about 150 mg/m$^2$, about 175 mg/m$^2$, about 200 mg/m$^2$, about 250 mg/m$^2$, about 300 mg/m$^2$, or about 350 mg/m$^2$ over a period of about 1 to 24 hours, about 1 to 20 hours, about 1-16 hours, about 2-12 hours, or about 3-8 hours once every three weeks.

In some embodiments, the present disclosure provides Compound A for use with irinotecan in treating metastatic breast cancer in a subject in need thereof, wherein the plasma exposure of the orally administered irinotecan, as measured by $AUC_{(0\to\infty)}$, is equal to or greater than the plasma exposure, as measured by $AUC_{(0\to\infty)}$, of intravenously administered irinotecan (e.g., Camptosar®) at an amount of about 50-400 mg/m$^2$ (e.g., 350 mg/m$^2$) over a period of about 1 to 24 hours once every three weeks.

In some embodiments, the present disclosure provides Compound A for use with irinotecan in treating metastatic breast cancer in a subject in need thereof, wherein the plasma exposure of the orally administered irinotecan, as measured by $AUC_{(0\to\infty)}$, is equal to or greater than the plasma exposure, as measured by $AUC_{(0\to\infty)}$, of intravenously administered irinotecan (e.g., Camptosar®) at an amount of about 10-400 mg/m$^2$, about 50-400 mg/m$^2$, about 100-400 mg/m$^2$, about 100 mg/m$^2$, about 125 mg/m$^2$, about 150 mg/m$^2$, about 175 mg/m$^2$, about 200 mg/m$^2$, about 250 mg/m$^2$, about 300 mg/m$^2$, or about 350 mg/m$^2$ over a period of about 1 to 24 hours, about 1 to 20 hours, about 1-16 hours, about 2-12 hours, or about 3-8 hours once every three weeks.

In some embodiments, the present disclosure provides Compound A for use with irinotecan in treating non-small cell lung cancer in a subject in need thereof, wherein the plasma exposure of the orally administered irinotecan, as measured by $AUC_{(0\to\infty)}$, is equal to or greater than the plasma exposure, as measured by $AUC_{(0\to\infty)}$, of intravenously administered irinotecan (e.g., Camptosar®) at an amount of about 50-400 mg/m$^2$ (e.g., 350 mg/m$^2$) over a period of about 1 to 24 hours once every three weeks.

In some embodiments, the present disclosure provides Compound A for use with irinotecan in treating non-small cell lung cancer in a subject in need thereof, wherein the plasma exposure of the orally administered irinotecan, as measured by $AUC_{(0\to\infty)}$, is equal to or greater than the plasma exposure, as measured by $AUC_{(0\to\infty)}$, of intravenously administered irinotecan (e.g., Camptosar®) at an amount of about 10-400 mg/m$^2$, about 50-400 mg/m$^2$, about 100-400 mg/m$^2$, about 100 mg/m$^2$, about 125 mg/m$^2$, about 150 mg/m$^2$, about 175 mg/m$^2$, about 200 mg/m$^2$, about 250 mg/m$^2$, about 300 mg/m$^2$, or about 350 mg/m$^2$ over a period of about 1 to 24 hours, about 1 to 20 hours, about 1-16 hours, about 2-12 hours, or about 3-8 hours once every three weeks.

In some embodiments, the present disclosure provides Compound A for use with irinotecan in treating adenocarcinoma of the pancreas in a subject in need thereof, wherein the plasma exposure of the orally administered irinotecan, as measured by $AUC_{(0\to\infty)}$, is equal to or greater than the plasma exposure, as measured by $AUC_{(0\to\infty)}$, of intravenously administered irinotecan (e.g., Camptosar®) at an amount of about 50-400 mg/m$^2$ (e.g., 350 mg/m$^2$) over a period of about 1 to 24 hours once every three weeks.

In some embodiments, the present disclosure provides Compound A for use with irinotecan in treating adenocarcinoma of the pancreas in a subject in need thereof, wherein the plasma exposure of the orally administered irinotecan, as measured by $AUC_{(0\to\infty)}$, is equal to or greater than the plasma exposure, as measured by $AUC_{(0\to\infty)}$, of intravenously administered irinotecan (e.g., Camptosar®) at an amount of about 10-400 mg/m$^2$, about 50-400 mg/m$^2$, about 100-400 mg/m$^2$, about 100 mg/m$^2$, about 125 mg/m$^2$, about 150 mg/m$^2$, about 175 mg/m$^2$, about 200 mg/m$^2$, about 250 mg/m$^2$, about 300 mg/m$^2$, or about 350 mg/m$^2$ over a period of about 1 to 24 hours, about 1 to 20 hours, about 1-16 hours, about 2-12 hours, or about 3-8 hours once every three weeks.

In some embodiments, the present disclosure provides Compound A for use with irinotecan in treating carcinoma of the ovary in a subject in need thereof, wherein the plasma exposure of the orally administered irinotecan, as measured by $AUC_{(0\to\infty)}$, is equal to or greater than the plasma exposure, as measured by $AUC_{(0\to\infty)}$, of intravenously administered irinotecan (e.g., Camptosar®) at an amount of about 50-400 mg/m$^2$ (e.g., 350 mg/m$^2$) over a period of about 1 to 24 hours once every three weeks.

In some embodiments, the present disclosure provides Compound A for use with irinotecan in treating carcinoma of the ovary in a subject in need thereof, wherein the plasma exposure of the orally administered irinotecan, as measured by $AUC_{(0\to\infty)}$, is equal to or greater than the plasma exposure, as measured by $AUC_{(0\to\infty)}$, of intravenously administered irinotecan (e.g., Camptosar®) at an amount of about 10-400 mg/m$^2$, about 50-400 mg/m$^2$, about 100-400 mg/m$^2$, about 100 mg/m$^2$, about 125 mg/m$^2$, about 150 mg/m$^2$, about 175 mg/m$^2$, about 200 mg/m$^2$, about 250 mg/m$^2$, about 300 mg/m$^2$, or about 350 mg/m$^2$ over a period of about 1 to 24 hours, about 1 to 20 hours, about 1-16 hours, about 2-12 hours, or about 3-8 hours once every three weeks.

In some embodiments, the present disclosure provides Compound A for use with irinotecan in treating carcinoma of the colon in a subject in need thereof, wherein the plasma exposure of the orally administered irinotecan, as measured by $AUC_{(0\to\infty)}$, is equal to or greater than the plasma exposure, as measured by $AUC_{(0\to\infty)}$, of intravenously administered irinotecan (e.g., Camptosar®) at an amount of about 50-400 mg/m$^2$ (e.g., 350 mg/m$^2$) over a period of about 1 to 24 hours once every three weeks.

In some embodiments, the present disclosure provides Compound A for use with irinotecan in treating carcinoma of the colon in a subject in need thereof, wherein the plasma exposure of the orally administered irinotecan, as measured by $AUC_{(0\to\infty)}$, is equal to or greater than the plasma exposure, as measured by $AUC_{(0\to\infty)}$, of intravenously administered irinotecan (e.g., Camptosar®) at an amount of about 10-400 mg/m$^2$, about 50-400 mg/m$^2$, about 100-400 mg/m$^2$, about 100 mg/m$^2$, about 125 mg/m$^2$, about 150 mg/m$^2$, about 175 mg/m$^2$, about 200 mg/m$^2$, about 250 mg/m$^2$, about 300 mg/m$^2$, or about 350 mg/m$^2$ over a period of about 1 to 24 hours, about 1 to 20 hours, about 1-16 hours, about 2-12 hours, or about 3-8 hours once every three weeks.

In some embodiments, the present disclosure provides Compound A for use with irinotecan in treating carcinoma of the breast in a subject in need thereof, wherein the plasma exposure of the orally administered irinotecan, as measured by $AUC_{(0\to\infty)}$, is equal to or greater than the plasma exposure, as measured by $AUC_{(0\to\infty)}$, of intravenously administered irinotecan (e.g., Camptosar®) at an amount of about 50-400 mg/m$^2$ (e.g., 350 mg/m$^2$) over a period of about 1 to 24 hours once every three weeks.

In some embodiments, the present disclosure provides Compound A for use with irinotecan in treating carcinoma of the breast in a subject in need thereof, wherein the plasma exposure of the orally administered irinotecan, as measured by $AUC_{(0\to\infty)}$, is equal to or greater than the plasma exposure, as measured by $AUC_{(0\to\infty)}$, of intravenously administered irinotecan (e.g., Camptosar®) at an amount of about 10-400 mg/m$^2$, about 50-400 mg/m$^2$, about 100-400 mg/m$^2$, about 100 mg/m$^2$, about 125 mg/m$^2$, about 150 mg/m$^2$, about 175 mg/m$^2$, about 200 mg/m$^2$, about 250 mg/m$^2$, about 300 mg/m$^2$, or about 350 mg/m$^2$ over a period of about 1 to 24 hours, about 1 to 20 hours, about 1-16 hours, about 2-12 hours, or about 3-8 hours once every three weeks.

In some embodiments, the present disclosure provides Compound A for use with irinotecan in treating AIDS-related Kaposi's Sarcoma in a subject in need thereof, wherein the plasma exposure of the orally administered irinotecan, as measured by $AUC_{(0\to\infty)}$, is equal to or greater than the plasma exposure, as measured by $AUC_{(0\to\infty)}$, of intravenously administered irinotecan (e.g., Camptosar®) at an amount of about 50-400 mg/m$^2$ (e.g., 350 mg/m$^2$) over a period of about 1 to 24 hours once every three weeks.

In some embodiments, the present disclosure provides Compound A for use with irinotecan in treating AIDS-related Kaposi's Sarcoma in a subject in need thereof, wherein the plasma exposure of the orally administered irinotecan, as measured by $AUC_{(0\to\infty)}$, is equal to or greater than the plasma exposure, as measured by $AUC_{(0\to\infty)}$, of intravenously administered irinotecan (e.g., Camptosar®) at an amount of about 10-400 mg/m$^2$, about 50-400 mg/m$^2$, about 100-400 mg/m$^2$, about 100 mg/m$^2$, about 125 mg/m$^2$, about 150 mg/m$^2$, about 175 mg/m$^2$, about 200 mg/m$^2$, about 250 mg/m$^2$, about 300 mg/m$^2$, or about 350 mg/m$^2$ over a period of about 1 to 24 hours, about 1 to 20 hours, about 1-16 hours, about 2-12 hours, or about 3-8 hours once every three weeks.

In some embodiments, the present disclosure provides use of Compound A in the manufacture of a medicament for use with irinotecan for treating colorectal cancer in a subject in need thereof, wherein the plasma exposure of the orally administered irinotecan, as measured by $AUC_{(0\to\infty)}$, is equal to or greater than the plasma exposure, as measured by $AUC_{(0\to\infty)}$, of intravenously administered irinotecan (e.g., Camptosar®) at an amount of about 50-400 mg/m$^2$ (e.g., 350 mg/m$^2$) over a period of about 1 to 24 hours once every three weeks.

In some embodiments, the present disclosure provides use of Compound A in the manufacture of a medicament for use with irinotecan for treating colorectal cancer in a subject in need thereof, wherein the plasma exposure of the orally administered irinotecan, as measured by $AUC_{(0\to\infty)}$, is equal to or greater than the plasma exposure, as measured by $AUC_{(0\to\infty)}$, of intravenously administered irinotecan (e.g., Camptosar®) at an amount of about 10-400 mg/m$^2$, about 50-400 mg/m$^2$, about 100-400 mg/m$^2$, about 100 mg/m$^2$, about 125 mg/m$^2$, about 150 mg/m$^2$, about 175 mg/m$^2$, about 200 mg/m$^2$, about 250 mg/m$^2$, about 300 mg/m$^2$, or about 350 mg/m$^2$ over a period of about 1 to 24 hours, about 1 to 20 hours, about 1-16 hours, about 2-12 hours, or about 3-8 hours once every three weeks.

In some embodiments, the present disclosure provides use of Compound A in the manufacture of a medicament for use with irinotecan for treating metastatic breast cancer in a subject in need thereof, wherein the plasma exposure of the orally administered irinotecan, as measured by $AUC_{(0\to\infty)}$, is equal to or greater than the plasma exposure, as measured by $AUC_{(0\to\infty)}$, of intravenously administered irinotecan (e.g., Camptosar®) at an amount of about 50-400 mg/m$^2$ (e.g., 350 mg/m$^2$) over a period of about 1 to 24 hours once every three weeks.

In some embodiments, the present disclosure provides use of Compound A in the manufacture of a medicament for use with irinotecan for treating metastatic breast cancer in a subject in need thereof, wherein the plasma exposure of the orally administered irinotecan, as measured by $AUC_{(0\to\infty)}$, is equal to or greater than the plasma exposure, as measured by $AUC_{(0\to\infty)}$, of intravenously administered irinotecan (e.g., Camptosar®) at an amount of about 10-400 mg/m$^2$, about 50-400 mg/m$^2$, about 100-400 mg/m$^2$, about 100 mg/m$^2$, about 125 mg/m$^2$, about 150 mg/m$^2$, about 175 mg/m$^2$, about 200 mg/m$^2$, about 250 mg/m$^2$, about 300 mg/m$^2$, or about 350 mg/m$^2$ over a period of about 1 to 24 hours, about 1 to 20 hours, about 1-16 hours, about 2-12 hours, or about 3-8 hours once every three weeks.

In some embodiments, the present disclosure provides use of Compound A in the manufacture of a medicament for use with irinotecan for treating non-small cell lung cancer in a subject in need thereof, wherein the plasma exposure of the orally administered irinotecan, as measured by $AUC_{(0\to\infty)}$, is equal to or greater than the plasma exposure, as measured by $AUC_{(0\to\infty)}$, of intravenously administered irinotecan (e.g., Camptosar®) at an amount of about 50-400 mg/m$^2$ (e.g., 350 mg/m$^2$) over a period of about 1 to 24 hours once every three weeks.

In some embodiments, the present disclosure provides use of Compound A in the manufacture of a medicament for use with irinotecan for treating non-small cell lung cancer in a subject in need thereof, wherein the plasma exposure of the orally administered irinotecan, as measured by $AUC_{(0\to\infty)}$, is equal to or greater than the plasma exposure, as measured by $AUC_{(0\to\infty)}$, of intravenously administered irinotecan (e.g., Camptosar®) at an amount of about 10-400 mg/m$^2$, about 50-400 mg/m$^2$, about 100-400 mg/m$^2$, about 100 mg/m$^2$, about 125 mg/m$^2$, about 150 mg/m$^2$, about 175 mg/m$^2$, about 200 mg/m$^2$, about 250 mg/m$^2$, about 300 mg/m$^2$, or about 350 mg/m$^2$ over a period of about 1 to 24 hours, about 1 to 20 hours, about 1-16 hours, about 2-12 hours, or about 3-8 hours once every three weeks.

In some embodiments, the present disclosure provides use of Compound A in the manufacture of a medicament for use with irinotecan for treating adenocarcinoma of the pancreas in a subject in need thereof, wherein the plasma exposure of the orally administered irinotecan, as measured by $AUC_{(0\to\infty)}$, is equal to or greater than the plasma exposure, as measured by $AUC_{(0\to\infty)}$, of intravenously administered irinotecan (e.g., Camptosar®) at an amount of about 50-400 mg/m$^2$ (e.g., 350 mg/m$^2$) over a period of about 1 to 24 hours once every three weeks.

In some embodiments, the present disclosure provides use of Compound A in the manufacture of a medicament for use with irinotecan for treating adenocarcinoma of the pancreas in a subject in need thereof, wherein the plasma exposure of the orally administered irinotecan, as measured by $AUC_{(0\to\infty)}$, is equal to or greater than the plasma exposure, as measured by $AUC_{(0\to\infty)}$, of intravenously administered irinotecan (e.g., Camptosar®) at an amount of about 10-400 mg/m$^2$, about 50-400 mg/m$^2$, about 100-400 mg/m$^2$, about 100 mg/m$^2$, about 125 mg/m$^2$, about 150 mg/m$^2$, about 175 mg/m$^2$, about 200 mg/m$^2$, about 250 mg/m$^2$, about 300 mg/m$^2$, or about 350 mg/m$^2$ over a period of about 1 to 24 hours, about 1 to 20 hours, about 1-16 hours, about 2-12 hours, or about 3-8 hours once every three weeks.

In some embodiments, the present disclosure provides use of Compound A in the manufacture of a medicament for use with irinotecan for treating carcinoma of the ovary in a subject in need thereof, wherein the plasma exposure of the orally administered irinotecan, as measured by $AUC_{(0\to\infty)}$, is equal to or greater than the plasma exposure, as measured by $AUC_{(0\to\infty)}$, of intravenously administered irinotecan (e.g., Camptosar®) at an amount of about 50-400 mg/m$^2$ (e.g., 350 mg/m$^2$) over a period of about 1 to 24 hours once every three weeks.

In some embodiments, the present disclosure provides use of Compound A in the manufacture of a medicament for use with irinotecan for treating carcinoma of the ovary in a subject in need thereof, wherein the plasma exposure of the orally administered irinotecan, as measured by $AUC_{(0\to\infty)}$, is equal to or greater than the plasma exposure, as measured by $AUC_{(0\to\infty)}$, of intravenously administered irinotecan (e.g., Camptosar®) at an amount of about 10-400 mg/m$^2$, about 50-400 mg/m$^2$, about 100-400 mg/m$^2$, about 100 mg/m$^2$, about 125 mg/m$^2$, about 150 mg/m$^2$, about 175 mg/m$^2$, about 200 mg/m$^2$, about 250 mg/m$^2$, about 300 mg/m$^2$, or about 350 mg/m$^2$ over a period of about 1 to 24 hours, about 1 to 20 hours, about 1-16 hours, about 2-12 hours, or about 3-8 hours once every three weeks.

In some embodiments, the present disclosure provides use of Compound A in the manufacture of a medicament for use with irinotecan for treating carcinoma of the colon in a subject in need thereof, wherein the plasma exposure of the orally administered irinotecan, as measured by $AUC_{(0\to\infty)}$, is equal to or greater than the plasma exposure, as measured by $AUC_{(0\to\infty)}$, of intravenously administered irinotecan (e.g., Camptosar®) at an amount of about 50-400 mg/m$^2$ (e.g., 350 mg/m$^2$) over a period of about 1 to 24 hours once every three weeks.

In some embodiments, the present disclosure provides use of Compound A in the manufacture of a medicament for use with irinotecan for treating carcinoma of the colon in a subject in need thereof, wherein the plasma exposure of the orally administered irinotecan, as measured by $AUC_{(0\to\infty)}$, is equal to or greater than the plasma exposure, as measured by $AUC_{(0\to\infty)}$, of intravenously administered irinotecan (e.g., Camptosar®) at an amount of about 10-400 mg/m$^2$, about 50-400 mg/m$^2$, about 100-400 mg/m$^2$, about 100 mg/m$^2$, about 125 mg/m$^2$, about 150 mg/m$^2$, about 175 mg/m$^2$, about 200 mg/m$^2$, about 250 mg/m$^2$, about 300 mg/m$^2$, or about 350 mg/m$^2$ over a period of about 1 to 24 hours, about 1 to 20 hours, about 1-16 hours, about 2-12 hours, or about 3-8 hours once every three weeks.

In some embodiments, the present disclosure provides use of Compound A in the manufacture of a medicament for use with irinotecan for treating carcinoma of the breast in a subject in need thereof, wherein the plasma exposure of the orally administered irinotecan, as measured by $AUC_{(0\to\infty)}$, is equal to or greater than the plasma exposure, as measured by $AUC_{(0\to\infty)}$, of intravenously administered irinotecan (e.g., Camptosar®) at an amount of about 50-400 mg/m$^2$ (e.g., 350 mg/m$^2$) over a period of about 1 to 24 hours once every three weeks.

In some embodiments, the present disclosure provides use of Compound A in the manufacture of a medicament for use with irinotecan for treating carcinoma of the breast in a subject in need thereof, wherein the plasma exposure of the orally administered irinotecan, as measured by $AUC_{(0\to\infty)}$, is equal to or greater than the plasma exposure, as measured by $AUC_{(0\to\infty)}$, of intravenously administered irinotecan (e.g., Camptosar®) at an amount of about 10-400 mg/m$^2$, about 50-400 mg/m$^2$, about 100-400 mg/m$^2$, about 100 mg/m$^2$, about 125 mg/m$^2$, about 150 mg/m$^2$, about 175 mg/m$^2$, about 200 mg/m$^2$, about 250 mg/m$^2$, about 300 mg/m$^2$, or about 350 mg/m$^2$ over a period of about 1 to 24 hours, about 1 to 20 hours, about 1-16 hours, about 2-12 hours, or about 3-8 hours once every three weeks.

In some embodiments, the present disclosure provides use of Compound A in the manufacture of a medicament for use with irinotecan for treating AIDS-related Kaposi's Sarcoma in a subject in need thereof, wherein the plasma exposure of the orally administered irinotecan, as measured by $AUC_{(0\to\infty)}$, is equal to or greater than the plasma exposure, as measured by $AUC_{(0\to\infty)}$, of intravenously administered irinotecan (e.g., Camptosar®) at an amount of about 50-400 mg/m$^2$ (e.g., 350 mg/m$^2$) over a period of about 1 to 24 hours once every three weeks.

In some embodiments, the present disclosure provides use of Compound A in the manufacture of a medicament for use with irinotecan for treating AIDS-related Kaposi's Sarcoma in a subject in need thereof, wherein the plasma exposure of the orally administered irinotecan, as measured by $AUC_{(0\to\infty)}$, is equal to or greater than the plasma exposure, as measured by $AUC_{(0\to\infty)}$, of intravenously administered irinotecan (e.g., Camptosar®) at an amount of about 10-400 mg/m$^2$, about 50-400 mg/m$^2$, about 100-400 mg/m$^2$, about 100 mg/m$^2$, about 125 mg/m$^2$, about 150 mg/m$^2$, about 175 mg/m$^2$, about 200 mg/m$^2$, about 250 mg/m$^2$, about 300 mg/m$^2$, or about 350 mg/m$^2$ over a period of about 1 to 24 hours, about 1 to 20 hours, about 1-16 hours, about 2-12 hours, or about 3-8 hours once every three weeks.

In some embodiments, the present disclosure provides Compound A for use with irinotecan in treating colorectal cancer in a subject in need thereof, wherein the plasma exposure of the orally administered irinotecan, as measured by $AUC_{(0\to\infty)}$, is equal to or greater than the plasma exposure, as measured by $AUC_{(0\to\infty)}$, of intravenously administered irinotecan (e.g., Camptosar®) at an amount of about 50-400 mg/m² (e.g., 350 mg/m²) over a period of about 1 to 24 hours once every three weeks.

In some embodiments, the present disclosure provides Compound A for use with irinotecan in treating colorectal cancer in a subject in need thereof, wherein the plasma exposure of the orally administered irinotecan, as measured by $AUC_{(0\to\infty)}$, is equal to or greater than the plasma exposure, as measured by $AUC_{(0\to\infty)}$, of intravenously administered irinotecan (e.g., Camptosar®) at an amount of about 10-400 mg/m², about 50-400 mg/m², about 100-400 mg/m², about 100 mg/m², about 125 mg/m², about 150 mg/m², about 175 mg/m², about 200 mg/m², about 250 mg/m², about 300 mg/m², or about 350 mg/m² over a period of about 1 to 24 hours, about 1 to 20 hours, about 1-16 hours, about 2-12 hours, or about 3-8 hours once every three weeks.

In some embodiments, the present disclosure provides Compound A for use with irinotecan in treating metastatic breast cancer in a subject in need thereof, wherein the plasma exposure of the orally administered irinotecan, as measured by $AUC_{(0\to\infty)}$, is equal to or greater than the plasma exposure, as measured by $AUC_{(0\to\infty)}$, of intravenously administered irinotecan (e.g., Camptosar®) at an amount of about 50-400 mg/m² (e.g., 350 mg/m²) over a period of about 1 to 24 hours once every three weeks.

In some embodiments, the present disclosure provides Compound A for use with irinotecan in treating metastatic breast cancer in a subject in need thereof, wherein the plasma exposure of the orally administered irinotecan, as measured by $AUC_{(0\to\infty)}$, is equal to or greater than the plasma exposure, as measured by $AUC_{(0\to\infty)}$, of intravenously administered irinotecan (e.g., Camptosar®) at an amount of about 10-400 mg/m², about 50-400 mg/m², about 100-400 mg/m², about 100 mg/m², about 125 mg/m², about 150 mg/m², about 175 mg/m², about 200 mg/m², about 250 mg/m², about 300 mg/m², or about 350 mg/m² over a period of about 1 to 24 hours, about 1 to 20 hours, about 1-16 hours, about 2-12 hours, or about 3-8 hours once every three weeks.

In some embodiments, the present disclosure provides Compound A for use with irinotecan in treating non-small cell lung cancer in a subject in need thereof, wherein the plasma exposure of the orally administered irinotecan, as measured by $AUC_{(0\to\infty)}$, is equal to or greater than the plasma exposure, as measured by $AUC_{(0\to\infty)}$, of intravenously administered irinotecan (e.g., Camptosar®) at an amount of about 50-400 mg/m² (e.g., 350 mg/m²) over a period of about 1 to 24 hours once every three weeks.

In some embodiments, the present disclosure provides Compound A for use with irinotecan in treating non-small cell lung cancer in a subject in need thereof, wherein the plasma exposure of the orally administered irinotecan, as measured by $AUC_{(0\to\infty)}$, is equal to or greater than the plasma exposure, as measured by $AUC_{(0\to\infty)}$, of intravenously administered irinotecan (e.g., Camptosar®) at an amount of about 10-400 mg/m², about 50-400 mg/m², about 100-400 mg/m², about 100 mg/m², about 125 mg/m², about 150 mg/m², about 175 mg/m², about 200 mg/m², about 250 mg/m², about 300 mg/m², or about 350 mg/m² over a period of about 1 to 24 hours, about 1 to 20 hours, about 1-16 hours, about 2-12 hours, or about 3-8 hours once every three weeks.

In some embodiments, the present disclosure provides Compound A for use with irinotecan in treating adenocarcinoma of the pancreas in a subject in need thereof, wherein the plasma exposure of the orally administered irinotecan, as measured by $AUC_{(0\to\infty)}$, is equal to or greater than the plasma exposure, as measured by $AUC_{(0\to\infty)}$, of intravenously administered irinotecan (e.g., Camptosar®) at an amount of about 50-400 mg/m² (e.g., 350 mg/m²) over a period of about 1 to 24 hours once every three weeks.

In some embodiments, the present disclosure provides Compound A for use with irinotecan in treating adenocarcinoma of the pancreas in a subject in need thereof, wherein the plasma exposure of the orally administered irinotecan, as measured by $AUC_{(0\to\infty)}$, is equal to or greater than the plasma exposure, as measured by $AUC_{(0\to\infty)}$, of intravenously administered irinotecan (e.g., Camptosar®) at an amount of about 10-400 mg/m², about 50-400 mg/m², about 100-400 mg/m², about 100 mg/m², about 125 mg/m², about 150 mg/m², about 175 mg/m², about 200 mg/m², about 250 mg/m², about 300 mg/m², or about 350 mg/m² over a period of about 1 to 24 hours, about 1 to 20 hours, about 1-16 hours, about 2-12 hours, or about 3-8 hours once every three weeks.

In some embodiments, the present disclosure provides Compound A for use with irinotecan in treating carcinoma of the ovary in a subject in need thereof, wherein the plasma exposure of the orally administered irinotecan, as measured by $AUC_{(0\to\infty)}$, is equal to or greater than the plasma exposure, as measured by $AUC_{(0\to\infty)}$, of intravenously administered irinotecan (e.g., Camptosar®) at an amount of about 50-400 mg/m² (e.g., 350 mg/m²) over a period of about 1 to 24 hours once every three weeks.

In some embodiments, the present disclosure provides Compound A for use with irinotecan in treating carcinoma of the ovary in a subject in need thereof, wherein the plasma exposure of the orally administered irinotecan, as measured by $AUC_{(0\to\infty)}$, is equal to or greater than the plasma exposure, as measured by $AUC_{(0\to\infty)}$, of intravenously administered irinotecan (e.g., Camptosar®) at an amount of about 10-400 mg/m², about 50-400 mg/m², about 100-400 mg/m², about 100 mg/m², about 125 mg/m², about 150 mg/m², about 175 mg/m², about 200 mg/m², about 250 mg/m², about 300 mg/m², or about 350 mg/m² over a period of about 1 to 24 hours, about 1 to 20 hours, about 1-16 hours, about 2-12 hours, or about 3-8 hours once every three weeks.

In some embodiments, the present disclosure provides Compound A for use with irinotecan in treating carcinoma of the colon in a subject in need thereof, wherein the plasma exposure of the orally administered irinotecan, as measured by $AUC_{(0\to\infty)}$, is equal to or greater than the plasma exposure, as measured by $AUC_{(0\to\infty)}$, of intravenously administered irinotecan (e.g., Camptosar®) at an amount of about 50-400 mg/m² (e.g., 350 mg/m²) over a period of about 1 to 24 hours once every three weeks.

In some embodiments, the present disclosure provides Compound A for use with irinotecan in treating carcinoma of the colon in a subject in need thereof, wherein the plasma exposure of the orally administered irinotecan, as measured by $AUC_{(0\to\infty)}$, is equal to or greater than the plasma exposure, as measured by $AUC_{(0\to\infty)}$, of intravenously administered irinotecan (e.g., Camptosar®) at an amount of about 10-400 mg/m², about 50-400 mg/m², about 100-400 mg/m², about 100 mg/m², about 125 mg/m², about 150 mg/m², about 175 mg/m², about 200 mg/m², about 250 mg/m², about 300 mg/m², or about 350 mg/m² over a period of about 1 to 24 hours, about 1 to 20 hours, about 1-16 hours, about 2-12 hours, or about 3-8 hours once every three weeks.

In some embodiments, the present disclosure provides Compound A for use with irinotecan in treating carcinoma of the breast in a subject in need thereof, wherein the plasma exposure of the orally administered irinotecan, as measured by $AUC_{(0\to\infty)}$, is equal to or greater than the plasma exposure, as measured by $AUC_{(0\to\infty)}$, of intravenously administered irinotecan (e.g., Camptosar®) at an amount of about 50-400 mg/m$^2$ (e.g., 350 mg/m$^2$) over a period of about 1 to 24 hours once every three weeks.

In some embodiments, the present disclosure provides Compound A for use with irinotecan in treating carcinoma of the breast in a subject in need thereof, wherein the plasma exposure of the orally administered irinotecan, as measured by AUC$_{(0\to\infty)}$, is equal to or greater than the plasma exposure, as measured by AUC$_{(0\to\infty)}$, of intravenously administered irinotecan (e.g., Camptosar®) at an amount of about 10-400 mg/m$^2$, about 50-400 mg/m$^2$, about 100-400 mg/m$^2$, about 100 mg/m$^2$, about 125 mg/m$^2$, about 150 mg/m$^2$, about 175 mg/m$^2$, about 200 mg/m$^2$, about 250 mg/m$^2$, about 300 mg/m$^2$, or about 350 mg/m$^2$ over a period of about 1 to 24 hours, about 1 to 20 hours, about 1-16 hours, about 2-12 hours, or about 3-8 hours once every three weeks.

In some embodiments, the present disclosure provides Compound A for use with irinotecan in treating AIDS-related Kaposi's Sarcoma in a subject in need thereof, wherein the plasma exposure of the orally administered irinotecan, as measured by AUC$_{(0\to\infty)}$, is equal to or greater than the plasma exposure, as measured by AUC$_{(0\to\infty)}$, of intravenously administered irinotecan (e.g., Camptosar®) at an amount of about 50-400 mg/m$^2$ (e.g., 350 mg/m$^2$) over a period of about 1 to 24 hours once every three weeks.

In some embodiments, the present disclosure provides Compound A for use with irinotecan in treating AIDS-related Kaposi's Sarcoma in a subject in need thereof, wherein the plasma exposure of the orally administered irinotecan, as measured by AUC$_{(0\to\infty)}$, is equal to or greater than the plasma exposure, as measured by AUC$_{(0\to\infty)}$, of intravenously administered irinotecan (e.g., Camptosar®) at an amount of about 10-400 mg/m$^2$, about 50-400 mg/m$^2$, about 100-400 mg/m$^2$, about 100 mg/m$^2$, about 125 mg/m$^2$, about 150 mg/m$^2$, about 175 mg/m$^2$, about 200 mg/m$^2$, about 250 mg/m$^2$, about 300 mg/m$^2$, or about 350 mg/m$^2$ over a period of about 1 to 24 hours, about 1 to 20 hours, about 1-16 hours, about 2-12 hours, or about 3-8 hours once every three weeks.

In some embodiments, the present disclosure provides Compound A for use in a combination therapy with irinotecan in the treatment of colorectal cancer in a subject in need thereof, wherein the plasma exposure of the orally administered irinotecan, as measured by AUC$_{(0\to\infty)}$, is equal to or greater than the plasma exposure, as measured by AUC$_{(0\to\infty)}$, of intravenously administered irinotecan (e.g., Camptosar®) at an amount of about 50-400 mg/m$^2$ (e.g., 350 mg/m$^2$) over a period of about 1 to 24 hours once every three weeks.

In some embodiments, the present disclosure provides Compound A for use in a combination therapy with irinotecan in the treatment of colorectal cancer in a subject in need thereof, wherein the plasma exposure of the orally administered irinotecan, as measured by AUC$_{(0\to\infty)}$, is equal to or greater than the plasma exposure, as measured by AUC$_{(0\to\infty)}$, of intravenously administered irinotecan (e.g., Camptosar®) at an amount of about 10-400 mg/m$^2$, about 50-400 mg/m$^2$, about 100-400 mg/m$^2$, about 100 mg/m$^2$, about 125 mg/m$^2$, about 150 mg/m$^2$, about 175 mg/m$^2$, about 200 mg/m$^2$, about 250 mg/m$^2$, about 300 mg/m$^2$, or about 350 mg/m$^2$ over a period of about 1 to 24 hours, about 1 to 20 hours, about 1-16 hours, about 2-12 hours, or about 3-8 hours once every three weeks.

In some embodiments, the present disclosure provides Compound A for use in a combination therapy with irinotecan in the treatment of metastatic breast cancer in a subject in need thereof, wherein the plasma exposure of the orally administered irinotecan, as measured by AUC$_{(0\to\infty)}$, is equal to or greater than the plasma exposure, as measured by AUC$_{(0\to\infty)}$, of intravenously administered irinotecan (e.g., Camptosar®) at an amount of about 50-400 mg/m$^2$ (e.g., 350 mg/m$^2$) over a period of about 1 to 24 hours once every three weeks.

In some embodiments, the present disclosure provides Compound A for use in a combination therapy with irinotecan in the treatment of metastatic breast cancer in a subject in need thereof, wherein the plasma exposure of the orally administered irinotecan, as measured by AUC$_{(0\to\infty)}$, is equal to or greater than the plasma exposure, as measured by AUC$_{(0\to\infty)}$, of intravenously administered irinotecan (e.g., Camptosar®) at an amount of about 10-400 mg/m$^2$, about 50-400 mg/m$^2$, about 100-400 mg/m$^2$, about 100 mg/m$^2$, about 125 mg/m$^2$, about 150 mg/m$^2$, about 175 mg/m$^2$, about 200 mg/m$^2$, about 250 mg/m$^2$, about 300 mg/m$^2$, or about 350 mg/m$^2$ over a period of about 1 to 24 hours, about 1 to 20 hours, about 1-16 hours, about 2-12 hours, or about 3-8 hours once every three weeks.

In some embodiments, the present disclosure provides Compound A for use in a combination therapy with irinotecan in the treatment of non-small cell lung cancer in a subject in need thereof, wherein the plasma exposure of the orally administered irinotecan, as measured by AUC$_{(0\to\infty)}$, is equal to or greater than the plasma exposure, as measured by AUC$_{(0\to\infty)}$, of intravenously administered irinotecan (e.g., Camptosar®) at an amount of about 50-400 mg/m$^2$ (e.g., 350 mg/m$^2$) over a period of about 1 to 24 hours once every three weeks.

In some embodiments, the present disclosure provides Compound A for use in a combination therapy with irinotecan in the treatment of non-small cell lung cancer in a subject in need thereof, wherein the plasma exposure of the orally administered irinotecan, as measured by AUC$_{(0\to\infty)}$, is equal to or greater than the plasma exposure, as measured by AUC$_{(0\to\infty)}$, of intravenously administered irinotecan (e.g., Camptosar®) at an amount of about 10-400 mg/m$^2$, about 50-400 mg/m$^2$, about 100-400 mg/m$^2$, about 100 mg/m$^2$, about 125 mg/m$^2$, about 150 mg/m$^2$, about 175 mg/m$^2$, about 200 mg/m$^2$, about 250 mg/m$^2$, about 300 mg/m$^2$, or about 350 mg/m$^2$ over a period of about 1 to 24 hours, about 1 to 20 hours, about 1-16 hours, about 2-12 hours, or about 3-8 hours once every three weeks.

In some embodiments, the present disclosure provides Compound A for use in a combination therapy with irinotecan in the treatment of adenocarcinoma of the pancreas in a subject in need thereof, wherein the plasma exposure of the orally administered irinotecan, as measured by AUC$_{(0\to\infty)}$, is equal to or greater than the plasma exposure, as measured by AUC$_{(0\to\infty)}$, of intravenously administered irinotecan (e.g., Camptosar®) at an amount of about 50-400 mg/m$^2$ (e.g., 350 mg/m$^2$) over a period of about 1 to 24 hours once every three weeks.

In some embodiments, the present disclosure provides Compound A for use in a combination therapy with irinotecan in the treatment of adenocarcinoma of the pancreas in a subject in need thereof, wherein the plasma exposure of the orally administered irinotecan, as measured by AUC$_{(0\to\infty)}$, is equal to or greater than the plasma exposure, as measured by AUC$_{(0\to\infty)}$, of intravenously administered irinotecan (e.g., Camptosar®) at an amount of about 10-400 mg/m$^2$, about 50-400 mg/m$^2$, about 100-400 mg/m$^2$, about 100 mg/m$^2$, about 125 mg/m$^2$, about 150 mg/m$^2$, about 175 mg/m$^2$, about 200 mg/m$^2$, about 250 mg/m$^2$, about 300 mg/m$^2$, or about 350 mg/m$^2$ over a period of about 1 to 24 hours, about 1 to 20 hours, about 1-16 hours, about 2-12 hours, or about 3-8 hours once every three weeks.

In some embodiments, the present disclosure provides Compound A for use in a combination therapy with irinotecan in the treatment of g carcinoma of the ovary in a subject in need thereof, wherein the plasma exposure of the orally administered irinotecan, as measured by $AUC_{(0\to\infty)}$, is equal to or greater than the plasma exposure, as measured by $AUC_{(0\to\infty)}$, of intravenously administered irinotecan (e.g., Camptosar®) at an amount of about 50-400 mg/m² (e.g., 350 mg/m²) over a period of about 1 to 24 hours once every three weeks.

In some embodiments, the present disclosure provides Compound A for use in a combination therapy with irinotecan in the treatment of carcinoma of the ovary in a subject in need thereof, wherein the plasma exposure of the orally administered irinotecan, as measured by $AUC_{(0\to\infty)}$, is equal to or greater than the plasma exposure, as measured by $AUC_{(0\to\infty)}$, of intravenously administered irinotecan (e.g., Camptosar®) at an amount of about 10-400 mg/m², about 50-400 mg/m², about 100-400 mg/m², about 100 mg/m², about 125 mg/m², about 150 mg/m², about 175 mg/m², about 200 mg/m², about 250 mg/m², about 300 mg/m², or about 350 mg/m² over a period of about 1 to 24 hours, about 1 to 20 hours, about 1-16 hours, about 2-12 hours, or about 3-8 hours once every three weeks.

In some embodiments, the present disclosure provides Compound A for use in a combination therapy with irinotecan in the treatment of carcinoma of the colon in a subject in need thereof, wherein the plasma exposure of the orally administered irinotecan, as measured by $AUC_{(0\to\infty)}$, is equal to or greater than the plasma exposure, as measured by $AUC_{(0\to\infty)}$, of intravenously administered irinotecan (e.g., Camptosar®) at an amount of about 50-400 mg/m² (e.g., 350 mg/m²) over a period of about 1 to 24 hours once every three weeks.

In some embodiments, the present disclosure provides Compound A for use in a combination therapy with irinotecan in the treatment of carcinoma of the colon in a subject in need thereof, wherein the plasma exposure of the orally administered irinotecan, as measured by $AUC_{(0\to\infty)}$, is equal to or greater than the plasma exposure, as measured by $AUC_{(0\to\infty)}$, of intravenously administered irinotecan (e.g., Camptosar®) at an amount of about 10-400 mg/m², about 50-400 mg/m², about 100-400 mg/m², about 100 mg/m², about 125 mg/m², about 150 mg/m², about 175 mg/m², about 200 mg/m², about 250 mg/m², about 300 mg/m², or about 350 mg/m² over a period of about 1 to 24 hours, about 1 to 20 hours, about 1-16 hours, about 2-12 hours, or about 3-8 hours once every three weeks.

In some embodiments, the present disclosure provides Compound A for use in a combination therapy with irinotecan in the treatment of carcinoma of the breast in a subject in need thereof, wherein the plasma exposure of the orally administered irinotecan, as measured by $AUC_{(0\to\infty)}$, is equal to or greater than the plasma exposure, as measured by $AUC_{(0\to\infty)}$, of intravenously administered irinotecan (e.g., Camptosar®) at an amount of about 50-400 mg/m² (e.g., 350 mg/m²) over a period of about 1 to 24 hours once every three weeks.

In some embodiments, the present disclosure provides Compound A for use in a combination therapy with irinotecan in the treatment of carcinoma of the breast in a subject in need thereof, wherein the plasma exposure of the orally administered irinotecan, as measured by $AUC_{(0\to\infty)}$, is equal to or greater than the plasma exposure, as measured by $AUC_{(0\to\infty)}$, of intravenously administered irinotecan (e.g., Camptosar®) at an amount of about 10-400 mg/m², about 50-400 mg/m², about 100-400 mg/m², about 100 mg/m², about 125 mg/m², about 150 mg/m², about 175 mg/m², about 200 mg/m², about 250 mg/m², about 300 mg/m², or about 350 mg/m² over a period of about 1 to 24 hours, about 1 to 20 hours, about 1-16 hours, about 2-12 hours, or about 3-8 hours once every three weeks.

In some embodiments, the present disclosure provides Compound A for use in a combination therapy with irinotecan in the treatment of AIDS-related Kaposi's Sarcoma in a subject in need thereof, wherein the plasma exposure of the orally administered irinotecan, as measured by $AUC_{(0\to\infty)}$, is equal to or greater than the plasma exposure, as measured by $AUC_{(0\to\infty)}$, of intravenously administered irinotecan (e.g., Camptosar®) at an amount of about 50-400 mg/m² (e.g., 350 mg/m²) over a period of about 1 to 24 hours once every three weeks.

In some embodiments, the present disclosure provides Compound A for use in a combination therapy with irinotecan in the treatment of AIDS-related Kaposi's Sarcoma in a subject in need thereof, wherein the plasma exposure of the orally administered irinotecan, as measured by $AUC_{(0\to\infty)}$, is equal to or greater than the plasma exposure, as measured by $AUC_{(0\to\infty)}$, of intravenously administered irinotecan (e.g., Camptosar®) at an amount of about 10-400 mg/m², about 50-400 mg/m², about 100-400 mg/m², about 100 mg/m², about 125 mg/m², about 150 mg/m², about 175 mg/m², about 200 mg/m², about 250 mg/m², about 300 mg/m², or about 350 mg/m² over a period of about 1 to 24 hours, about 1 to 20 hours, about 1-16 hours, about 2-12 hours, or about 3-8 hours once every three weeks.

In some embodiments, the present disclosure provides a medicament comprising Compound A for use in a combination therapy with irinotecan in the treatment of colorectal cancer in a subject in need thereof, wherein the plasma exposure of the orally administered irinotecan, as measured by $AUC_{(0\to\infty)}$, is equal to or greater than the plasma exposure, as measured by $AUC_{(0\to\infty)}$, of intravenously administered irinotecan (e.g., Camptosar®) at an amount of about 50-400 mg/m² (e.g., 350 mg/m²) over a period of about 1 to 24 hours once every three weeks.

In some embodiments, the present disclosure provides a medicament comprising Compound A for use in a combination therapy with irinotecan in the treatment of colorectal cancer in a subject in need thereof, wherein the plasma exposure of the orally administered irinotecan, as measured by $AUC_{(0\to\infty)}$, is equal to or greater than the plasma exposure, as measured by $AUC_{(0\to\infty)}$, of intravenously administered irinotecan (e.g., Camptosar®) at an amount of about 10-400 mg/m², about 50-400 mg/m², about 100-400 mg/m², about 100 mg/m², about 125 mg/m², about 150 mg/m², about 175 mg/m², about 200 mg/m², about 250 mg/m², about 300 mg/m², or about 350 mg/m² over a period of about 1 to 24 hours, about 1 to 20 hours, about 1-16 hours, about 2-12 hours, or about 3-8 hours once every three weeks.

In some embodiments, the present disclosure provides a medicament comprising Compound A for use in a combination therapy with irinotecan in the treatment of metastatic breast cancer in a subject in need thereof, wherein the plasma exposure of the orally administered irinotecan, as measured by $AUC_{(0\to\infty)}$, is equal to or greater than the plasma exposure, as measured by $AUC_{(0\to\infty)}$, of intravenously administered irinotecan (e.g., Camptosar®) at an amount of about 50-400 mg/m² (e.g., 350 mg/m²) over a period of about 1 to 24 hours once every three weeks.

In some embodiments, the present disclosure provides a medicament comprising Compound A for use in a combination therapy with irinotecan in the treatment of metastatic breast cancer in a subject in need thereof, wherein the plasma exposure of the orally administered irinotecan, as measured by $AUC_{(0\to\infty)}$, is equal to or greater than the plasma exposure, as measured by $AUC_{(0\to\infty)}$, of intravenously administered irinotecan (e.g., Camptosar®) at an amount of about 10-400 mg/m$^2$, about 50-400 mg/m$^2$, about 100-400 mg/m$^2$, about 100 mg/m$^2$, about 125 mg/m$^2$, about 150 mg/m$^2$, about 175 mg/m$^2$, about 200 mg/m$^2$, about 250 mg/m$^2$, about 300 mg/m$^2$, or about 350 mg/m$^2$ over a period of about 1 to 24 hours, about 1 to 20 hours, about 1-16 hours, about 2-12 hours, or about 3-8 hours once every three weeks.

In some embodiments, the present disclosure provides a medicament comprising Compound A for use in a combination therapy with irinotecan in the treatment of non-small cell lung cancer in a subject in need thereof, wherein the plasma exposure of the orally administered irinotecan, as measured by $AUC_{(0\to\infty)}$, is equal to or greater than the plasma exposure, as measured by $AUC_{(0\to\infty)}$, of intravenously administered irinotecan (e.g., Camptosar®) at an amount of about 50-400 mg/m$^2$ (e.g., 350 mg/m$^2$) over a period of about 1 to 24 hours once every three weeks.

In some embodiments, the present disclosure provides a medicament comprising Compound A for use in a combination therapy with irinotecan in the treatment of non-small cell lung cancer in a subject in need thereof, wherein the plasma exposure of the orally administered irinotecan, as measured by $AUC_{(0\to\infty)}$, is equal to or greater than the plasma exposure, as measured by $AUC_{(0\to\infty)}$, of intravenously administered irinotecan (e.g., Camptosar®) at an amount of about 10-400 mg/m$^2$, about 50-400 mg/m$^2$, about 100-400 mg/m$^2$, about 100 mg/m$^2$, about 125 mg/m$^2$, about 150 mg/m$^2$, about 175 mg/m$^2$, about 200 mg/m$^2$, about 250 mg/m$^2$, about 300 mg/m$^2$, or about 350 mg/m$^2$ over a period of about 1 to 24 hours, about 1 to 20 hours, about 1-16 hours, about 2-12 hours, or about 3-8 hours once every three weeks.

In some embodiments, the present disclosure provides a medicament comprising Compound A for use in a combination therapy with irinotecan in the treatment of adenocarcinoma of the pancreas in a subject in need thereof, wherein the plasma exposure of the orally administered irinotecan, as measured by $AUC_{(0\to\infty)}$, is equal to or greater than the plasma exposure, as measured by $AUC_{(0\to\infty)}$, of intravenously administered irinotecan (e.g., Camptosar®) at an amount of about 50-400 mg/m$^2$ (e.g., 350 mg/m$^2$) over a period of about 1 to 24 hours once every three weeks.

In some embodiments, the present disclosure provides a medicament comprising Compound A for use in a combination therapy with irinotecan in the treatment of adenocarcinoma of the pancreas in a subject in need thereof, wherein the plasma exposure of the orally administered irinotecan, as measured by $AUC_{(0\to\infty)}$, is equal to or greater than the plasma exposure, as measured by $AUC_{(0\to\infty)}$, of intravenously administered irinotecan (e.g., Camptosar®) at an amount of about 10-400 mg/m$^2$, about 50-400 mg/m$^2$, about 100-400 mg/m$^2$, about 100 mg/m$^2$, about 125 mg/m$^2$, about 150 mg/m$^2$, about 175 mg/m$^2$, about 200 mg/m$^2$, about 250 mg/m$^2$, about 300 mg/m$^2$, or about 350 mg/m$^2$ over a period of about 1 to 24 hours, about 1 to 20 hours, about 1-16 hours, about 2-12 hours, or about 3-8 hours once every three weeks.

In some embodiments, the present disclosure provides a medicament comprising Compound A for use in a combination therapy with irinotecan in the treatment of carcinoma of the ovary in a subject in need thereof, wherein the plasma exposure of the orally administered irinotecan, as measured by $AUC_{(0\to\infty)}$, is equal to or greater than the plasma exposure, as measured by $AUC_{(0\to\infty)}$, of intravenously administered irinotecan (e.g., Camptosar®) at an amount of about 50-400 mg/m$^2$ (e.g., 350 mg/m$^2$) over a period of about 1 to 24 hours once every three weeks.

In some embodiments, the present disclosure provides a medicament comprising Compound A for use in a combination therapy with irinotecan in the treatment of carcinoma of the ovary in a subject in need thereof, wherein the plasma exposure of the orally administered irinotecan, as measured by $AUC_{(0\to\infty)}$, is equal to or greater than the plasma exposure, as measured by $AUC_{(0\to\infty)}$, of intravenously administered irinotecan (e.g., Camptosar®) at an amount of about 10-400 mg/m$^2$, about 50-400 mg/m$^2$, about 100-400 mg/m$^2$, about 100 mg/m$^2$, about 125 mg/m$^2$, about 150 mg/m$^2$, about 175 mg/m$^2$, about 200 mg/m$^2$, about 250 mg/m$^2$, about 300 mg/m$^2$, or about 350 mg/m$^2$ over a period of about 1 to 24 hours, about 1 to 20 hours, about 1-16 hours, about 2-12 hours, or about 3-8 hours once every three weeks.

In some embodiments, the present disclosure provides a medicament comprising Compound A for use in a combination therapy with irinotecan in the treatment of carcinoma of the colon in a subject in need thereof, wherein the plasma exposure of the orally administered irinotecan, as measured by $AUC_{(0\to\infty)}$, is equal to or greater than the plasma exposure, as measured by $AUC_{(0\to\infty)}$, of intravenously administered irinotecan (e.g., Camptosar®) at an amount of about 50-400 mg/m$^2$ (e.g., 350 mg/m$^2$) over a period of about 1 to 24 hours once every three weeks.

In some embodiments, the present disclosure provides a medicament comprising Compound A for use in a combination therapy with irinotecan in the treatment of carcinoma of the colon in a subject in need thereof, wherein the plasma exposure of the orally administered irinotecan, as measured by $AUC_{(0\to\infty)}$, is equal to or greater than the plasma exposure, as measured by $AUC_{(0\to\infty)}$, of intravenously administered irinotecan (e.g., Camptosar®) at an amount of about 10-400 mg/m$^2$, about 50-400 mg/m$^2$, about 100-400 mg/m$^2$, about 100 mg/m$^2$, about 125 mg/m$^2$, about 150 mg/m$^2$, about 175 mg/m$^2$, about 200 mg/m$^2$, about 250 mg/m$^2$, about 300 mg/m$^2$, or about 350 mg/m$^2$ over a period of about 1 to 24 hours, about 1 to 20 hours, about 1-16 hours, about 2-12 hours, or about 3-8 hours once every three weeks.

In some embodiments, the present disclosure provides a medicament comprising Compound A for use in a combination therapy with irinotecan in the treatment of carcinoma of the breast in a subject in need thereof, wherein the plasma exposure of the orally administered irinotecan, as measured by $AUC_{(0\to\infty)}$, is equal to or greater than the plasma exposure, as measured by $AUC_{(0\to\infty)}$, of intravenously administered irinotecan (e.g., Camptosar®) at an amount of about 50-400 mg/m$^2$ (e.g., 350 mg/m$^2$) over a period of about 1 to 24 hours once every three weeks.

In some embodiments, the present disclosure provides a medicament comprising Compound A for use in a combination therapy with irinotecan in the treatment of carcinoma of the breast in a subject in need thereof, wherein the plasma exposure of the orally administered irinotecan, as measured by $AUC_{(0\to\infty)}$, is equal to or greater than the plasma exposure, as measured by $AUC_{(0\to\infty)}$, of intravenously administered irinotecan (e.g., Camptosar®) at an amount of about 10-400 mg/m$^2$, about 50-400 mg/m$^2$, about 100-400 mg/m$^2$, about 100 mg/m$^2$, about 125 mg/m$^2$, about 150 mg/m$^2$, about 175 mg/m$^2$, about 200 mg/m$^2$, about 250 mg/m$^2$, about 300 mg/m$^2$, or about 350 mg/m$^2$ over a period of about 1 to 24 hours, about 1 to 20 hours, about 1-16 hours, about 2-12 hours, or about 3-8 hours once every three weeks.

In some embodiments, the present disclosure provides a medicament comprising Compound A for use in a combination therapy with irinotecan in the treatment of AIDS-related Kaposi's Sarcoma in a subject in need thereof, wherein the plasma exposure of the orally administered irinotecan, as measured by $AUC_{(0\to\infty)}$, is equal to or greater than the plasma exposure, as measured by $AUC_{(0\to\infty)}$, of intravenously administered irinotecan (e.g., Camptosar®) at an amount of about 50-400 mg/m² (e.g., 350 mg/m²) over a period of about 1 to 24 hours once every three weeks.

In some embodiments, the present disclosure provides a medicament comprising Compound A for use in a combination therapy with irinotecan in the treatment of AIDS-related Kaposi's Sarcoma in a subject in need thereof, wherein the plasma exposure of the orally administered irinotecan, as measured by $AUC_{(0\to\infty)}$, is equal to or greater than the plasma exposure, as measured by $AUC_{(0\to\infty)}$, of intravenously administered irinotecan (e.g., Camptosar®) at an amount of about 10-400 mg/m², about 50-400 mg/m², about 100-400 mg/m², about 100 mg/m², about 125 mg/m², about 150 mg/m², about 175 mg/m², about 200 mg/m², about 250 mg/m², about 300 mg/m², or about 350 mg/m² over a period of about 1 to 24 hours, about 1 to 20 hours, about 1-16 hours, about 2-12 hours, or about 3-8 hours once every three weeks.

In some embodiments, the subject is fasted before irinotecan and/or Compound A is orally administered. In some embodiments, the subject is fasted for at least 3 hours, at least 4 hours, at least 6 hours, at least 8 hours, at least 12 hours, at least 18 hours, or at least 24 hours. In some embodiments, the subject is fasted for at least 12 hours, at least 18 hours, or at least 24 hours before irinotecan and/or Compound A is orally administered.

Unless explicitly indicated otherwise, the terms "approximately" and "about" are synonymous. In some embodiments, "approximately" and "about" refer to the recited amount, dose, value (for example, $AUC_{(0\to\infty)}$), or duration ±20%, ±15%, ±10%, ±8%, ±6%, ±5%, ±4%, ±2%, ±1%, or ±0.5%. In another embodiment, "approximately" and "about" refer to the listed amount, value, or duration ±10%, ±8%, ±6%, ±5%, ±4%, or ±2%. In yet another embodiment, "approximately" and "about" refer to the listed amount, value, or duration ±5%. In yet another embodiment, "approximately" and "about" refer to the listed amount, value, or duration ±2%. In yet another embodiment, "approximately" and "about" refer to the listed amount, value, or duration ±1%. When the terms "approximately" and "about" are used when reciting temperature or temperature range, these terms refer to the recited temperature or temperature range ±5° C., ±2° C., or ±1° C. In another embodiment, the terms "approximately" and "about" refer to the recited temperature or temperature range ±2° C.

In some embodiments, the subject is screened for gene promoter polymorphisms. In some embodiments, the subject is screened for UGT gene promoter polymorphisms. In some embodiments, the subject is screened for UGT1A1 gene promoter polymorphisms. In some embodiments, the subject is screened for a UGT1A1*28 polymorphism. In some embodiments, the subject is screened for a UGT1A1*6 polymorphism. In some embodiments the subject is not homozygous for UGT1A1*28. In some embodiments the subject is not homozygous for UGT1A1*6.

The term "irinotecan" refers to (4S)-4,11-Diethyl-4-hydroxy-3,14-dioxo-3,4,12,14-tetrahydro-1H-pyrano[3',4':6,7]indolizino[1,2-b]quinolin-9-yl 1,4'-bipiperidine-1'-carboxylate, CAS Number 97682-44-5, $C_{33}H_{38}N_4O_6$, i.e., the compound with the following structure:

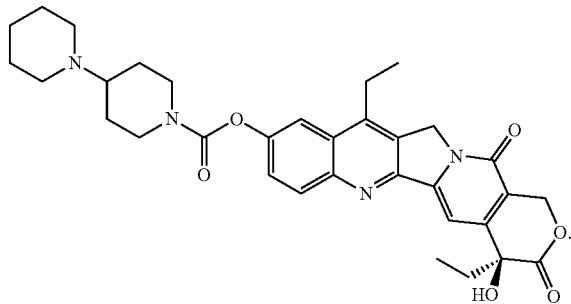 [SMILES: CCc1c2c(nc3ccc(OC(=O)N4CCC(N5CCCCC5)CC4)cc13)-c1cc3c(c(=O)n1C2)COC(=O)[C@]3(O)CC]

Unless otherwise indicated, the term "irinotecan" includes pharmaceutically acceptable salts and/or solvates thereof.

Irinotecan is in the topoisomerase inhibitor family of medication. It works by blocking topoisomerase 1 which results in DNA damage and cell death. Irinotecan is activated by hydrolysis to SN-38, an inhibitor of topoisomerase 1. This is then inactivated by glucuronidation by uridine diphosphate glucuronosyltransferase 1A1 (UGT1A1). The inhibition of topoisomerase 1 by the active metabolite SN-38 eventually leads to inhibition of both DNA replication and transcription. The molecular action of irinotecan occurs by trapping a subset of topoisomerase-1-DNA cleavage complexes, those with a guanine +1 in the DNA sequence. One irinotecan molecule stacks against the base pairs flanking the topoisomerase-induced cleavage site and inactivates the topoisomerase 1 enzyme.

Irinotecan suitable for intravenous administration or intravenously administered irinotecan includes compositions that comprise irinotecan and a pharmaceutical excipient that facilitates the intravenous administration of irinotecan. Such pharmaceutical excipient includes sorbitol. In some embodiments, the irinotecan suitable for intravenous administration or intravenously administered irinotecan includes the brand name product, CAMPTOSAR®, and generic versions thereof. In some embodiments, the irinotecan suitable for intravenous administration or intravenously administered irinotecan includes the brand name products, CAMPTO® or ONIVYDE®, and generic versions thereof.

Irinotecan suitable for oral administration or orally administered irinotecan refers to a formulation of irinotecan that is administered orally.

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Solid dosage forms for oral administration include microencapsulated active compound forms, optionally with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents.

In some embodiments, the orally administered irinotecan is in capsule form. In some embodiments, each capsule contains irinotecan and an excipient, e.g., sorbitol. In some embodiments, each capsule contains 30 mg-200 mg of irinotecan. In some embodiments, each capsule contains 30 mg, 45 mg, 60 mg, 75 mg, 90 mg, 100 mg, 125 mg, 150 mg, 175 mg, or 200 mg of irinotecan. In some embodiments, each capsule contains 30 mg of irinotecan. In some embodiments, each capsule contains 500 mg of sorbitol. In some embodiments each capsule contains 30 mg of irinotecan and 500 mg of sorbitol. In some embodiments, the orally administered irinotecan is in tablet form. In some embodiments, each tablet contains 30 mg-200 mg of irinotecan. In some embodiments, each tablet contains 30 mg, 45 mg, 60 mg, 75 mg, 90 mg, 100 mg, 125 mg, 150 mg, 175 mg, or 200 mg of irinotecan. In some embodiments, each tablet contains 30 mg of irinotecan. In some embodiments, the orally administered irinotecan is in solution form. In some embodiments, each solution contains 30 mg-200 mg of irinotecan. In some embodiments, each solution contains 30 mg, 45 mg, 60 mg, 75 mg, 90 mg, 100 mg, 125 mg, 150 mg, 175 mg, or 200 mg of irinotecan. In some embodiments, each solution contains 30 mg of irinotecan.

Oral formulation of irinotecan (e.g., capsule, tablet, or solution) may be formulated by any suitable methods known in the art.

The term "Compound A" refers to a compound, or a pharmaceutically acceptable salt and/or solvate thereof, which is a P-gp pump inhibitor and has the following structure:

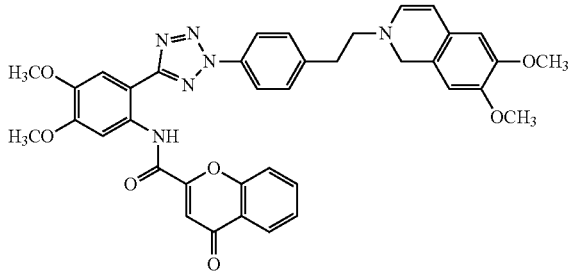 [SMILES: COc1cc2c(cc1OC)CN(CCc1ccc(-n3nnc(-c4cc(OC)c(OC)cc4NC(=O)c4cc(=O)c5ccccc5o4)n3)cc1)C=C2]

Unless indicated otherwise, the terms "Compound A," "HM30181 methanesulfonate monohydrate," "HM30181A," "HM30181AK," and "HM30181AK-US" are all equivalent and are used interchangeably. In some embodiments, Compound A refers to a methanesulfonate salt monohydrate of Compound A:

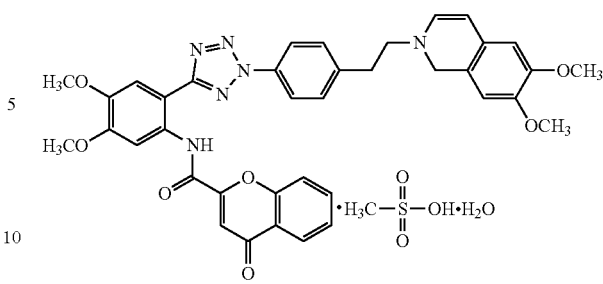

In some embodiments, Compound A refers to a methanesulfonate salt monohydrate of Compound A Compound A is commercially available, e.g., in tablet form suitable for oral administration. In some embodiments, Compound A is administered in 15 mg tablets suitable for oral administration.

Compound A may be formulated by any suitable methods known in the art.

The term "subject" includes any living organism that has cancer or is at a risk of developing cancer. In some embodiments, the term "subject" refers to a mammal that has cancer or is at a risk of developing cancer. In some embodiments, the term subject refers to a human being that has cancer or is at a risk of developing cancer. In some embodiments, the term subject refers to a cancer patient, i.e., a patient.

The term "$AUC_{(0 \to \infty)}$" refers to the total exposure to a drug and is expressed in unit of concentration time. In some embodiments, it is the concentration of a drug (e.g. irinotecan and/or its active metabolite SN-38 over a time interval circulating in the body, e.g., in the plasma, blood, or serum. In some embodiments, $AUC_{(0 \to \infty)} = AUC_{(0 \to Tlast)} + (C_{Tlast}/K_{elim})$, where $C_{Tlast}$ is the last measureable measurable drug concentration and $K_{elim}$, is the terminal elimination rate constant, expressed in time$^{-1}$ units.

In some embodiments, $C_{Tlast}$ may be determined from about 1 day to about 21 days after oral administration of irinotecan.

In some embodiments, $C_{Tlast}$ may be determined from about 2 days to about 14 days after oral administration of irinotecan.

In some embodiments, $C_{Tlast}$ may be determined from about 3 days to about 7 days after oral administration of irinotecan.

In some embodiments, $C_{Tlast}$ may be determined at about 3 days after oral administration of irinotecan.

In some embodiments, $C_{Tlast}$ may be determined at about 4 days after oral administration of irinotecan.

In some embodiments, $C_{Tlast}$ may be determined at about 5 days after oral administration of irinotecan.

In some embodiments, $C_{Tlast}$ may be determined at about 6 days after oral administration of irinotecan.

In some embodiments, $C_{Tlast}$ may be determined at about 7 days after oral administration of irinotecan.

Hematologic toxicity associated with the intravenous administration of irinotecan in a subject suffering from cancer can be assessed by a medical professional or health care worker by analyzing blood samples in a subject, i.e., determining cell counts, including white blood cells, absolute neutrophils, platelets, and hemoglobin.

Hypersensitivity-type infusion reactions, and symptoms associated with hematologic toxicity and/or neurotoxicity associated with the intravenous administration of irinotecan in a subject suffering from cancer can be assessed by a medical professional or health care worker.

As used herein, the phrase "pharmaceutically acceptable" refers to those compounds, materials, compositions, carriers, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The term "QD" refers to every day, the term "Q1W" refers to every one week, the term "Q2W" refers to every two weeks, and the term "Q3W" refers to every three weeks.

The term "QD×2" refers to on day 1 and day 2 weekly, the term "QD×3" refers to on day 1-day 3 weekly, the term "QD×4" refers to on day 1-day 4 weekly, the term "QD×5" refers to on day 1-day 5 weekly, and the term "QD×6" refers to on day 1-day 6 weekly.

The term "oral irinotecan", as used herein, refers to irinotecan administered as oral formulations, as described herein, in combination with Compound A, as described herein.

"Pharmaceutically acceptable excipient" means an excipient that is useful in preparing a pharmaceutical composition that is generally safe, non-toxic and neither biologically nor otherwise undesirable, and includes excipient that is acceptable for veterinary use as well as human pharmaceutical use. A "pharmaceutically acceptable excipient" as used in the specification and claims includes both one and more than one such excipient.

The term "therapeutically effective amount", as used herein, refers to an amount of a pharmaceutical agent to treat, ameliorate, or prevent an identified disease or condition, or to exhibit a detectable therapeutic or inhibitory effect. The effect can be detected by any assay method known in the art. The precise effective amount for a subject will depend upon the subject's body weight, size, and health; the nature and extent of the condition; and the therapeutic or combination of therapeutics selected for administration. Therapeutically effective amounts for a given situation can be determined by routine experimentation that is within the skill and judgment of the clinician.

For any compound, the therapeutically effective amount can be estimated initially either in cell culture assays or in animal models, usually rats, mice, rabbits, dogs, or pigs. The animal model may also be used to determine the appropriate concentration range and route of administration. Such information can then be used to determine useful doses and routes for administration in humans. Therapeutic/prophylactic efficacy and toxicity may be determined by standard pharmaceutical procedures in cell cultures or experimental animals, e.g., $ED_{50}$ (the dose therapeutically effective in 50% of the population) and $LD_{50}$ (the dose lethal to 50% of the population). The dose ratio between toxic and therapeutic effects is the therapeutic index, and it can be expressed as the ratio, $LD_{50}/ED_{50}$. Pharmaceutical compositions that exhibit large therapeutic indices are preferred. The dosage may vary within this range depending upon the dosage form employed, sensitivity of the patient, and the route of administration.

Dosage and administration are adjusted to provide sufficient levels of the active ingredient or to maintain the desired effect. Factors which may be taken into account include the severity of the disease state, general health of the subject, age, weight, and gender of the subject, diet, time and frequency of administration, drug combination(s), reaction sensitivities, and tolerance/response to therapy. Long-acting pharmaceutical compositions may be administered every 3 to 4 days, every week, or once every two weeks depending on half-life and clearance rate of the particular formulation.

The pharmaceutical compositions containing irinotecan may be manufactured in a manner that is generally known, e.g., by means of conventional mixing, dissolving, granulating, dragee-making, levigating, emulsifying, encapsulating, entrapping, or lyophilizing processes. Pharmaceutical compositions may be formulated in a conventional manner using one or more pharmaceutically acceptable carriers comprising excipients and/or auxiliaries that facilitate processing of the active ingredient into preparations that can be used pharmaceutically. Of course, the appropriate formulation is dependent upon the route of administration chosen.

Pharmaceutical compositions suitable for injectable use include sterile aqueous solutions (where water soluble) or dispersions and sterile powders for the extemporaneous preparation of sterile injectable solutions or dispersions. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringeability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating irinotecan in the required amount in an appropriate solvent with one or a combination of ingredients enumerated above, as required, followed by filtered sterilization. Generally, dispersions are prepared by incorporating form irinotecan into a sterile vehicle that contains a basic dispersion medium and the required other ingredients from those enumerated above. In the case of sterile powders for the preparation of sterile injectable solutions, methods of preparation are vacuum drying and freeze-drying that yields a powder of irinotecan plus any additional desired ingredient from a previously sterile-filtered solution thereof.

Oral compositions generally include an inert diluent or an edible pharmaceutically acceptable carrier. They can be enclosed in gelatin capsules or compressed into tablets. For the purpose of oral therapeutic administration, form can be incorporated with excipients and used in the form of tablets, troches, or capsules. Oral compositions can also be prepared using a fluid carrier for use as a mouthwash, wherein in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

The pharmaceutical compositions described herein can be included in a container, pack, or dispenser together with instructions for administration.

All percentages and ratios used herein, unless otherwise indicated, are by weight.

Other features and advantages of the present disclosure are apparent from the different examples. The provided examples illustrate different components and methodology useful in practicing the present disclosure.

The examples do not limit the claimed disclosure. Based on the present disclosure the skilled artisan can identify and employ other components and methodology useful for practicing the present disclosure.

EXAMPLES

Example 1—Monotherapy Study 1 to Determine Maximum Tolerated Dose (MTD) of Orally Administered Irinotecan in Combination with Compound A Oral irinotecan was administered at a dosing regimen of 5-30 mg/m$^2$ per day for five days during a 21 day cycle. The pharmacokinetics of oral irinotecan and its active metabolite M1 ("SN38") increased proportionally with dose. Orally administered irinotecan was determined to have a maximum tolerated dose (MTD) of 20 mg/m$^2$ per day when dosed five days of week one during a three-week cycle.

TABLE 1

Study 1: Mean pharmacokinetic parameters of oral irinotecan and M1

| | Day 1 Oral Irinotecan Dose Group (mg/m$^2$) | | | | | | Day 5 Oral Irinotecan Dose Group (mg/m$^2$) | | | | | |
|---|---|---|---|---|---|---|---|---|---|---|---|---|
| | 5 | 10 | 15 | 20 | 25 | 30 | 5 | 10 | 15 | 20 | 25 | 30 |
| AUC$_{24}$ (μg · hr/L) | 50.87 | 109.57 | 193.95 | 277.47 | 481.39 | 454.54 | 64.59 | 209.12 | 379.56 | 412.22 | 703.08 | 736.12 |
| C$_{max}$ (μg/L) | 6.52 | 13.96 | 20.55 | 33.90 | 44.37 | 34.60 | 6.37 | 22.87 | 33.80 | 31.93 | 63.63 | 57.30 |

| | Day 1 M 1 Dose Group (mg/m$^2$) | | | | | | Day 5 M 1 Dose Group (mg/m$^2$) | | | | | |
|---|---|---|---|---|---|---|---|---|---|---|---|---|
| | 5 | 10 | 15 | 20 | 25 | 30 | 5 | 10 | 15 | 20 | 25 | 30 |
| AUC$_{24}$ (μg · hr/L) | 49.83 | 46.04 | 50.29 | 63.56 | 143.97 | 83.64 | 68.61 | 51.40 | 118.29 | 119.38 | 178.58 | 308.27 |
| C$_{max}$ (μg/L) | 6.07 | 7.84 | 5.33 | 8.92 | 17.10 | 7.31 | 5.84 | 6.15 | 11.14 | 11.73 | 14.93 | 13.44 |
| Metabolic ratio | 1.64 | 0.61 | 0.39 | 0.35 | 0.50 | 0.29 | 2.67 | 0.44 | 0.69 | 0.75 | 0.63 | 0.39 |

Example 2—Monotherapy Study 2 to Determine Maximum Tolerated Dose (MTD) of Orally Administered Irinotecan in Combination with Compound A Oral irinotecan was administered at a dosing regimen of 5-20 mg/m$^2$ per day for 10 days during a 21 day cycle. The pharmacokinetics of oral irinotecan and its active metabolite M1 ("SN38") increased proportionally with dose. Orally administered irinotecan was determined to have a MTD of 10 mg/m$^2$ per day when dosed five days of week one and week two during a three-week cycle.

TABLE 2

Study 2: Mean pharmacokinetic parameters of oral irinotecan and M1

| | Day 1 Irinotecan Dose Group (mg/m$^2$) | | | | Day 12 Irinotecan Dose Group (mg/m$^2$) | | | |
|---|---|---|---|---|---|---|---|---|
| | 5 | 10 | 15 | 20 | 5 | 10 | 15 | 20 |
| AUC$_{24}$ (μg · hr/L) | 72.08 | 123.07 | 283.69 | 271.47 | 95.08 | 185.64 | 280.75 | 441.56 |
| C$_{max}$ (μg/L) | 9.65 | 15.50 | 26.95 | 28.80 | 10.89 | 17.90 | 38.10 | 64.60 |

TABLE 2-continued

Study 2: Mean pharmacokinetic parameters of oral irinotecan and M1

| | Day 1 M 1 Dose Group (mg/m²) | | | | Day 12 M 1 Dose Group (mg/m²) | | | |
|---|---|---|---|---|---|---|---|---|
| | 5 | 10 | 15 | 20 | 5 | 10 | 15 | 20 |
| $AUC_{24}$ (ug · hr/L) | 41.40 | 43.34 | 85.61 | 54.44 | 42.53 | 38.17 | 144.14 | 71.97 |
| $C_{max}$ (µg/L) | 7.08 | 5.04 | 10.19 | 4.15 | 6.10 | 4.04 | 18.00 | 7.63 |
| Metabolic ratio | 1.5 | 0.55 | 0.45 | 0.34 | 1.0 | 0.36 | 0.83 | 0.44 |

Figure 10:
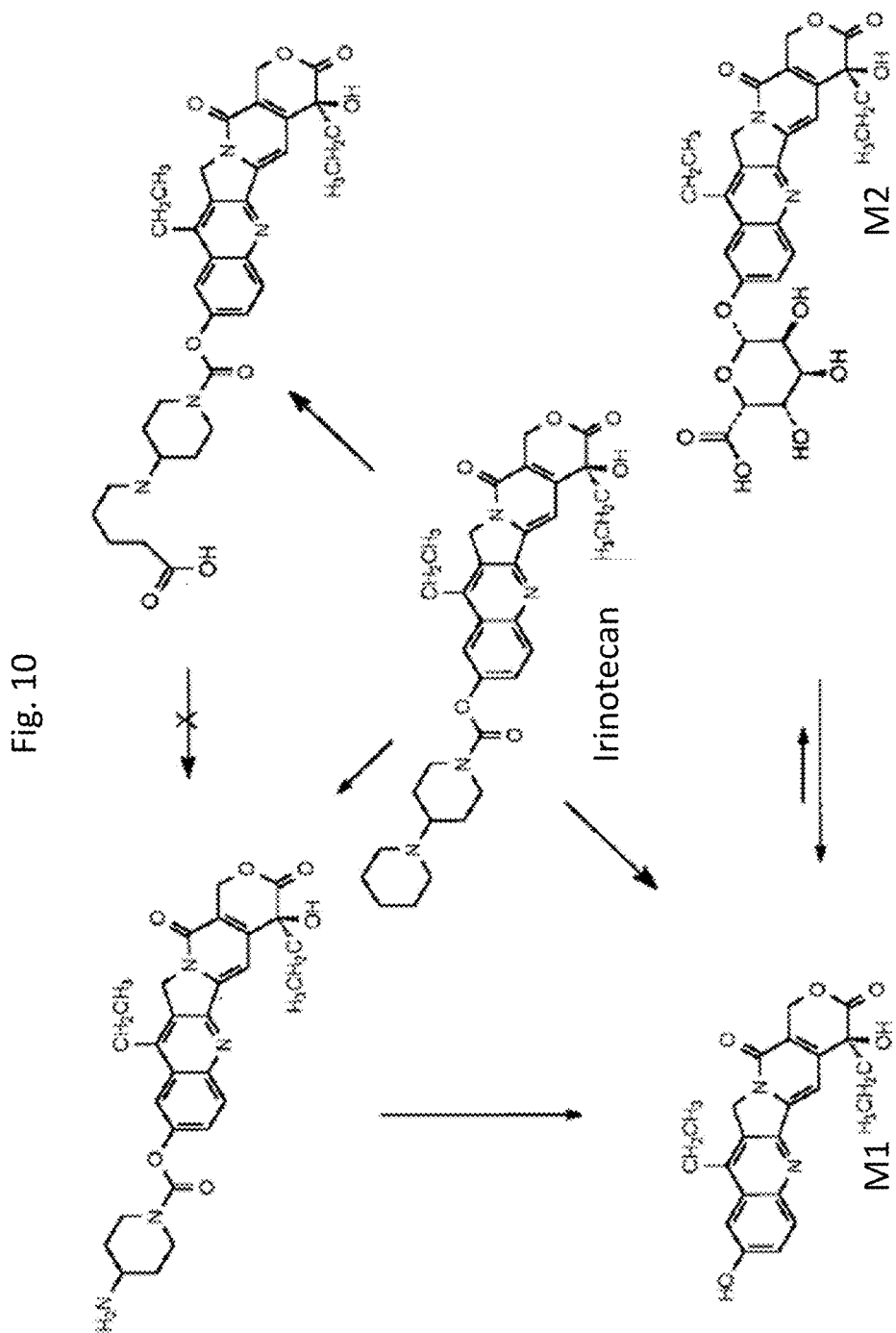
FIG. 10 is the metabolite profile of irinotecan, including M1 and M2.

Example 3—Pharmacokinetics of Orally Administered Irinotecan in Combination with Compound A and Corresponding Metabolites for Dose Range Study Oral irinotecan was administered at a single dose once per 21 day cycle ("Study 4") from 20 to 320 mg/m². The pharmacokinetic range and profiles of oral irinotecan, irinotecan's active metabolite M1, and further metabolized M1, M2 ("SN38G"), were investigated. Oral irinotecan was dosed as an oral solution or tablet. The oral irinotecan solution was dosed at 20, 40, 80, and 120 mg/m². The oral irinotecan tablet was dosed at 120, 160, 200, 240, 280, and 320 mg/m². FIG. 10 shows the metabolic profile of irinotecan, including M1 and M2.

The oral irinotecan plasma pharmacokinetic profile (FIG. 1A and FIG. 1B) follows a biexponential decay at each dose level. Oral irinotecan exposure increased with increase of dose. The $C_{max}$ began to plateau at 200 mg/m², and continued with dose escalation. The highest mean profile was achieved with a dose of 320 mg/m².

TABLE 3

Oral irinotecan pharmacokinetic profile across dose range

| Dose mg/m² | Subject | $C_{max}$ (ng/mL) | $T_{max}$ (hr) | $T_{last}$ (hr) | $AUC_{24}$ (ng · hr/ mL) | $AUC_{last}$ (ng · hr/ mL) | $AUC_{inf}$ (ng · hr/ mL) | $R^2$ | $AUC_{\% extrap}$ | $T_{1/2}$ (hr) |
|---|---|---|---|---|---|---|---|---|---|---|
| 240 | 1 | 668 | 3 | 72 | 4510 | 5220 | 5240 | 1.00 | 0.550 | 10.3 |
| | 2 | 1140 | 3 | 72 | 11300 | 12800 | 13000 | 0.957 | 1.14 | 13.1 |
| | 3 | 587 | 3 | 72 | 5070 | 6180 | 6230 | 0.963 | 0.760 | 9.8 |
| 280 | 4 | 736 | 1 | 72 | 5020 | 5890 | 6010 | 0.983 | 2 | 15.3 |
| | 5 | 939 | 2 | 72 | 7710 | 8470 | 8510 | 0.956 | 0.456 | 8.25 |
| | 6 | 615 | 3 | 72 | 5390 | 6340 | 6430 | 0.989 | 1.36 | 13.1 |
| 320 | 7 | 1180 | 3 | 72 | 13000 | 15700 | 15900 | 0.999 | 1.09 | 11.7 |
| | 8 | 1370 | 2 | 168 | 14300 | 18100 | 18200 | 0.986 | 0.553 | 29.3 |
| | 9 | 616 | 3 | 72 | 6590 | 8260 | 8460 | 0.992 | 2.28 | 15.0 |

Figure 2A:
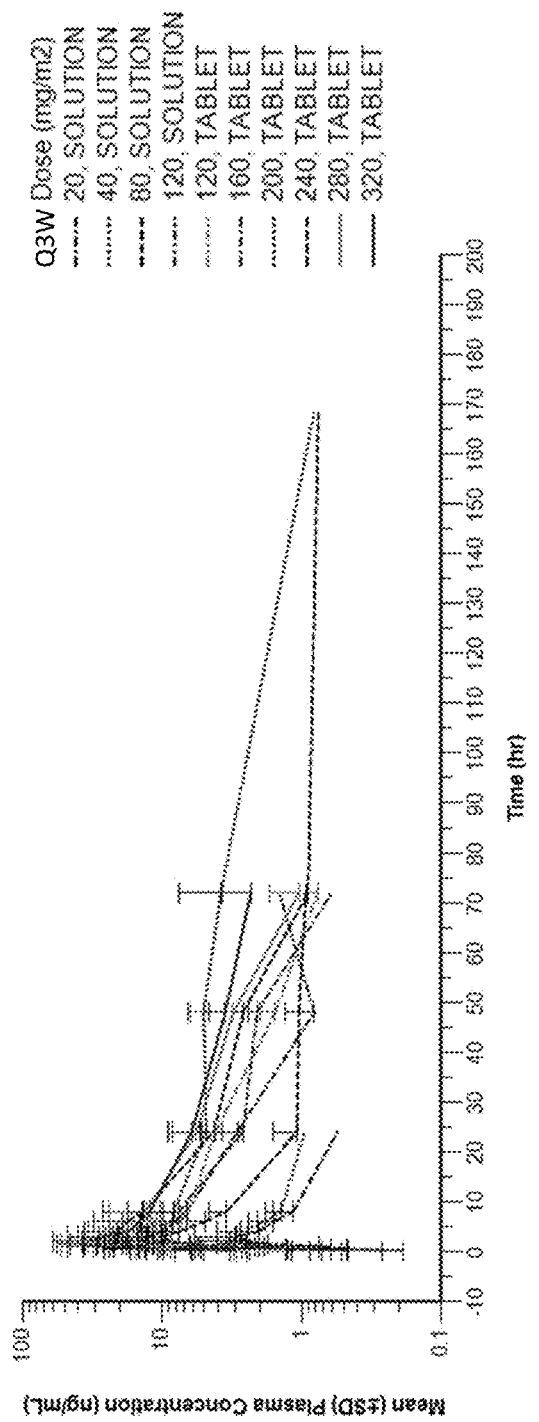
FIG. 2A is a graph showing the mean plasma concentration (ng/mL) versus time (hr) of M1 across dose ranges for solution (20, 40, 80, and 120 mg/m$^2$) and tablet (120, 160, 200, 240, 280, and 320 mg/m$^2$) of time to 200 hours.

The M1 plasma pharmacokinetic profile (FIG. 2A and FIG. 2B) showed a plasma concentration increase with dose. Terminal elimination half-life was approximately 20 hours, with a range across all dose levels from 6.4 to 25.3 hours. Enterohepatic recycling (EHR) of M1 was observed in the plasma concentration profile with an early EHR at 5.5 hr and a possible EHR at 50 hr. The mean plasma concentrations of M1 at a dose of 280 or 320 mg/m² exhibited overlapping properties.

TABLE 4

Summary of M1 Mean Plasma Pharmacokinetic Parameters

| | Dose (mg) | Stat | $C_{max}$ (ng/mL) | $T_{max}*$ (hr) | $T_{last}$ (hr) | $AUC_{0-24}$ (ng*hr/mL) | $AUC_{0-inf}$ (ng*hr/mL) | $T_{1/2}$ (hr) |
|---|---|---|---|---|---|---|---|---|
| Tablet | 120 | N | 3 | 3 | 3 | 3 | 2 | 2 |
| | | Mean (CV %) | 23.1 (58.4) | 3.00 | 56.0 | 168 (32.9) | 274 (18.3) | 19.7 (25.3) |
| | 160 | N | 3 | 3 | 3 | 3 | 3 | 3 |
| | | Mean (CV %) | 25.0 (58.1) | 3.00 | 48.0 (21.7) | 156 (22.6) | 235 (13.4) | 15.3 (53.3) |
| | 200 | N | 3 | 3 | 3 | 3 | 3 | 3 |
| | | Mean (CV %) | 23.0 (102) | 3.00 | 88.0 (83.3) | 185 (66.3) | 468 (90.0) | 23.9 (71.1) |
| | 240 | N | 3 | 3 | 3 | 3 | 1 | 1 |
| | | Mean (CV %) | 28.3 (67.3) | 3.00 | 96.0 (66.1) | 264 (66.4) | 224 | 20.0 |
| | 280 | N | 3 | 3 | 3 | 3 | 3 | 3 |
| | | Mean (CV %) | 37.6 (42.4) | 1.5 | 72.0 (0) | 293 (60.0) | 468 (67.3) | 18.5 (1.49) |
| | 320 | N | 3 | 3 | 3 | 3 | 1 | 1 |
| | | Mean (CV %) | 38.5 (58.7) | 2.00 | 72.0 (0) | 300 (42.3) | 349 | 20.4 |

TABLE 5

M1 pharmacokinetic profile across dose range

| Dose mg/m² | Subject | $C_{max}$ (ng/mL) | $T_{max}$ (hr) | $T_{last}$ (hr) | $AUC_{24}$ (ng·hr/mL) | $AUC_{last}$ (ng·hr/mL) | $AUC_{inf}$ (ng·hr/mL) | $R^2$ | $AUC_{\% \, extrap}$ | $T_{1/2}$ (hr) |
|---|---|---|---|---|---|---|---|---|---|---|
| 240 | 1 | 17.1 | 3 | 48 | 133 | 185 | 224 | 0.998 | 17.4 | 20 |
|  | 2 | 50.3 | 3 | 168 | 463 | 636 | — |  |  |  |
|  | 3 | 17.5 | 3 | 72 | 195 | 376 | — |  |  |  |
| 280 | 4 | 55.4 | 1 | 72 | 497 | 783 | 831 | 0.936 | 5.80 | 18.4 |
|  | 5 | 33.0 | 1.5 | 72 | 190 | 256 | 273 | 0.966 | 6.24 | 18.4 |
|  | 6 | 24.5 | 3 | 72 | 194 | 282 | 300 | 0.999 | 6.13 | 18.8 |
| 320 | 7 | 28.1 | 1.5 | 72 | 212 | 322 | 349 | 1.00 | 7.56 | 20.4 |
|  | 8 | 64.8 | 2 | 72 | 445 | 713 | — |  |  |  |
|  | 9 | 23.2 | 3 | 72 | 242 | 410 | — |  |  |  |

Figure 3A:
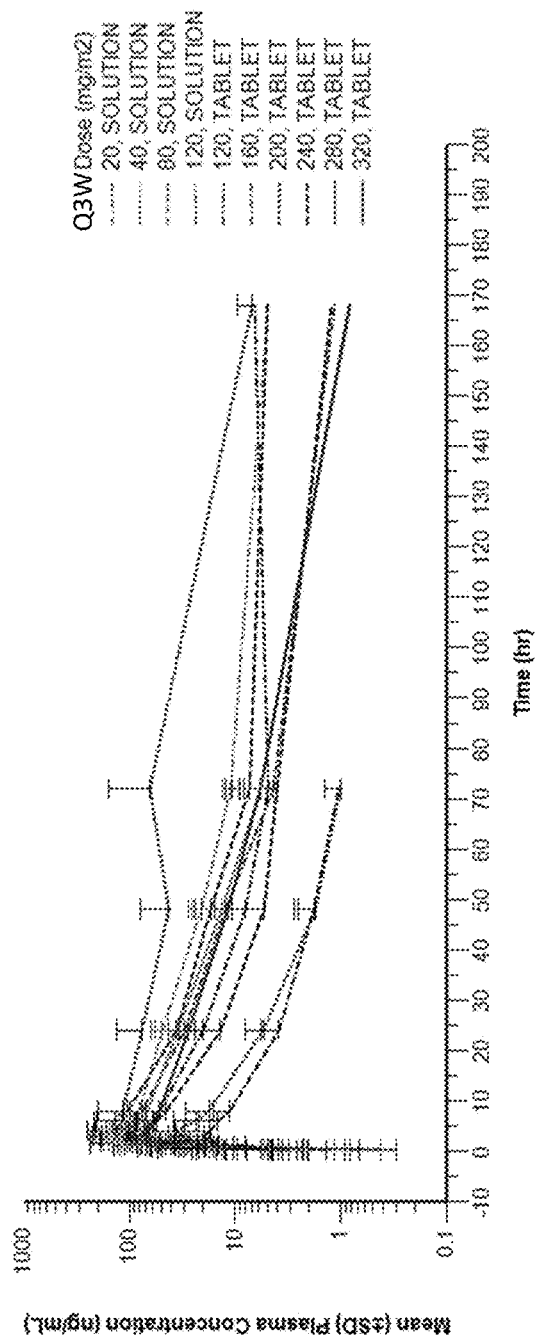
FIG. 3A is a graph showing the mean plasma concentration (ng/mL) versus time (hr) of M2 across dose ranges for solution (20, 40, 80, and 120 mg/m$^2$) and tablet (120, 160, 200, 240, 280, and 320 mg/m$^2$) for time to 200 hours.

The M2 plasma pharmacokinetic profile (FIG. 3A and FIG. 3B) showed increase with dose and followed a biexponential decay. The M2 $C_{max}$ was comparable at tablet doses of 200, 240, and 280 mg/m² of oral irinotecan. EHR of M2 was observed in the plasma concentration profile. For individuals administered the oral irinotecan tablets of 120 mg/m² or above, the M2 $C_{max}$ CV % ranged from 42-102% and $AUC_{inf}$ CV % ranged from 18-90%.

$AUC_{24}$ Comparison

Figure 4A:
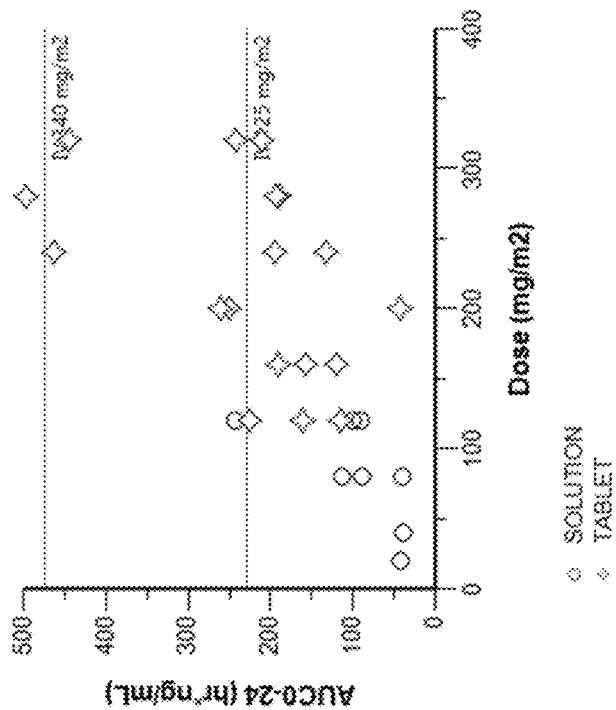
FIG. 4A is a graph showing the AUC$_{24}$ comparison of oral irinotecan across dose ranges.
Figure 4B:
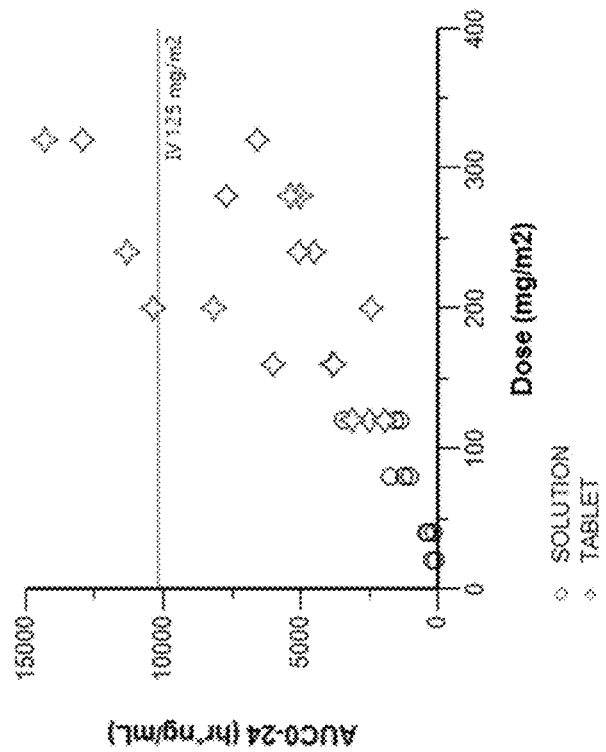
FIG. 4B is a graph showing the AUC$_{24}$ comparison of M1 across dose ranges.

Oral irinotecan in both solution and tablet $AUC_{24}$ comparison is shown in FIG. 4A and FIG. 4B. Oral irinotecan (FIG. 4A) and M1 (FIG. 4B) pharmacokinetics were variable above a dose of 160 mg/m². Comparable M1 exposures of oral irinotecan and IV irinotecan ($AUC_{24}$) of 4 of 9 subjects at a dose level of 200 mg/m² and above were seen.

$C_{max}$ Comparison

Figure 5A:
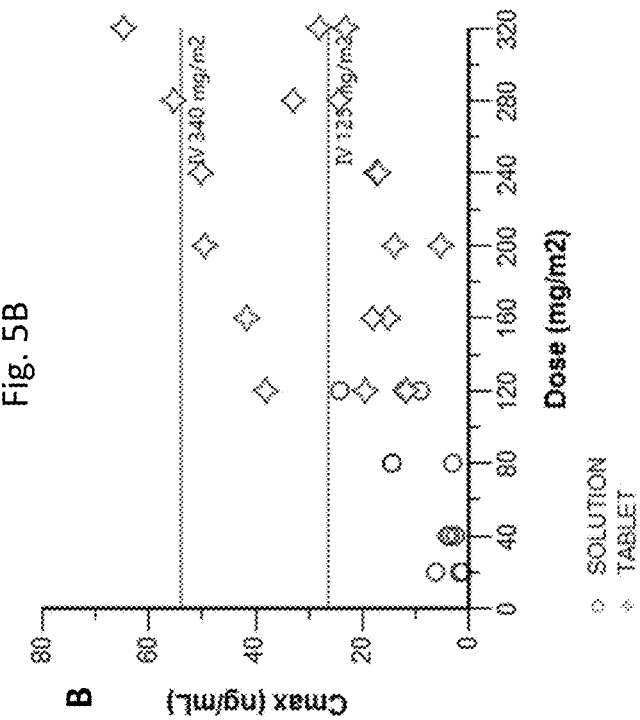
FIG. 5A is a graph showing the C$_{max}$ comparison of oral irinotecan across dose ranges.
Figure 5B:
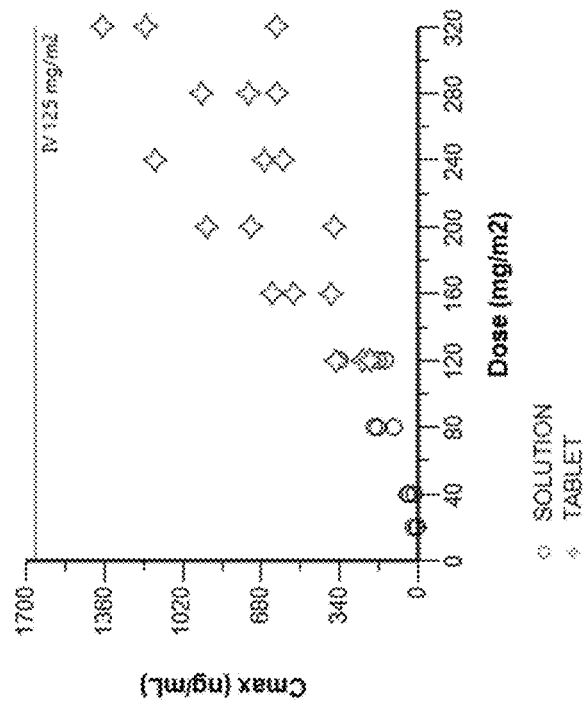
FIG. 5B is a graph showing the C$_{max}$ comparison of M1 across dose ranges.

Oral irinotecan in both solution and tablet $C_{max}$ comparison is shown in FIG. 5A and FIG. 5B. The oral irinotecan $C_{max}$ was below the range for 125 mg/m² of IV dosed irinotecan (FIG. 5A). The reference line for IV dose of 340 mg/m² with a $C_{max}$ of 3392 ng/mL is above the Y axis limitation of FIG. 5A.

M1 $C_{max}$ was variable across all dose levels for tablet formulation. The M1 $C_{max}$ was in a range of that observed with IV irinotecan dosage of 340 mg/m² (FIG. 5B). The oral solution administration of irinotecan had a M1 $C_{max}$ that exhibited properties within the range of 125 mg/m² dosed IV irinotecan.

Relationship Between Dose and $AUC_{inf}$

Figure 6A:
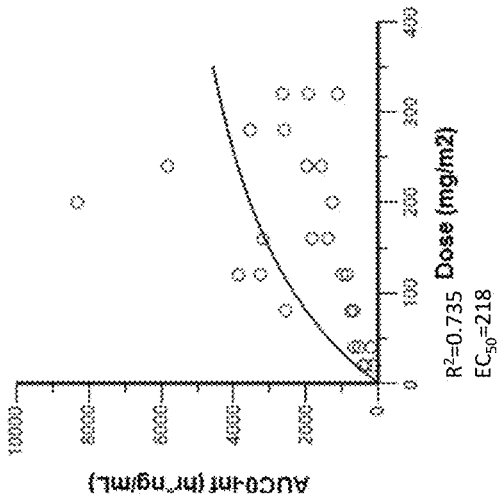
FIG. 6A is a graph showing the relationship between dose and AUC$_{inf}$ with E$_{max}$ projection for oral irinotecan.
Figure 6B:
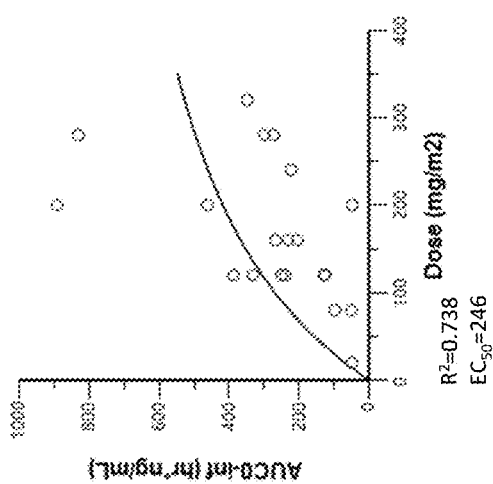
FIG. 6B is a graph showing the relationship between dose and AUC$_{inf}$ with E$_{max}$ projection for M1.
Figure 6C:
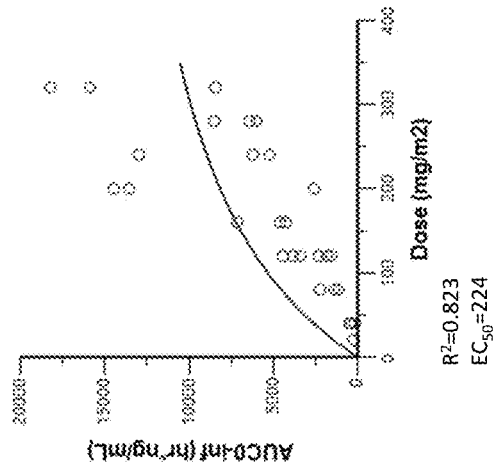
FIG. 6C is a graph showing the relationship between dose and AUC$_{inf}$ with E$_{max}$ projection for M2.

The observed exposure data was fit to a simple $E_{max}$ model to predict mean observed exposures at each dose level for oral irinotecan (FIG. 6A), M1 (FIG. 6B), and M2 (FIG. 6C). The observed mean $AUC_{inf}$ of oral irinotecan at a dose of 240 mg/m² was shown to be comparable to the predicted model, Table 6. The M1 predicted $AUC_{inf}$ and observed mean at a dose of 280 and 200 mg/m² are shown to be comparable, Table 7. The M2 predicted $AUC_{inf}$ increased with an increase of dose. The observed mean $AUC_{inf}$ decreased with an increase of dose, Table 8.

TABLE 6

Oral irinotecan $E_{max}$ model for predicted $AUC_{inf}$

| Dose | Predicted $AUC_{inf}$ | Observed Mean $AUC_{inf}$ |
|---|---|---|
| 320 mg/m² | 10189 | 14200 |
| 280 mg/m² | 8253 | 6980 |
| 240 mg/m² | 7679 | 8150 |
| 200 mg/m² | 6992 | 10200 |

TABLE 7

M1 $E_{max}$ model for predicted $AUC_{inf}$

| Dose | Predicted $AUC_{inf}$ | Observed Mean $AUC_{inf}$ |
|---|---|---|
| 320 mg/m² | 528 | 349 |
| 280 mg/m² | 499 | 468 |
| 240 mg/m² | 464 | 224 |
| 200 mg/m² | 423 | 468 |

TABLE 8

M2 $E_{max}$ model for predicted $AUC_{inf}$

| Dose | Predicted $AUC_{inf}$ | Observed Mean $AUC_{inf}$ |
|---|---|---|
| 320 mg/m² | 4414 | 1900 |
| 280 mg/m² | 4347 | 3080 |
| 240 mg/m² | 4029 | 3130 |
| 200 mg/m² | 3651 | 4800 |

Relationship Between Dose and $AUC_{inf}$

Figure 7C:
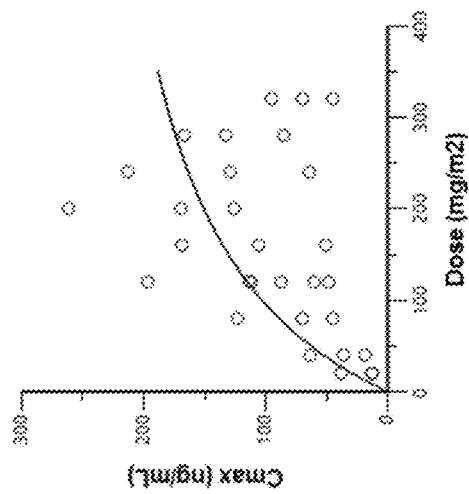
FIG. 7C is a graph showing the relationship between dose and C$_{max}$ with E$_{max}$ projection for M2.
Figure 7B:
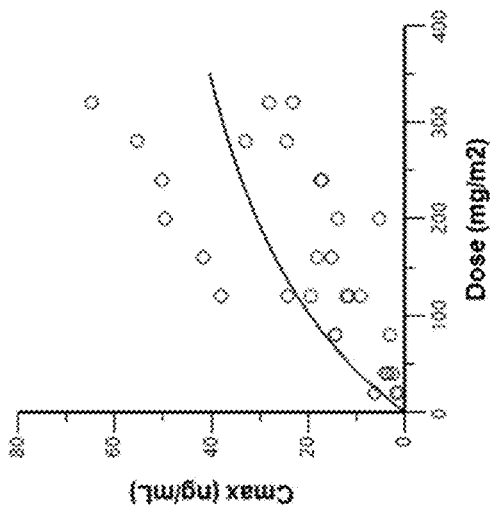
FIG. 7B is a graph showing the relationship between dose and C$_{max}$ with E$_{max}$ projection for M1.
Figure 7A:
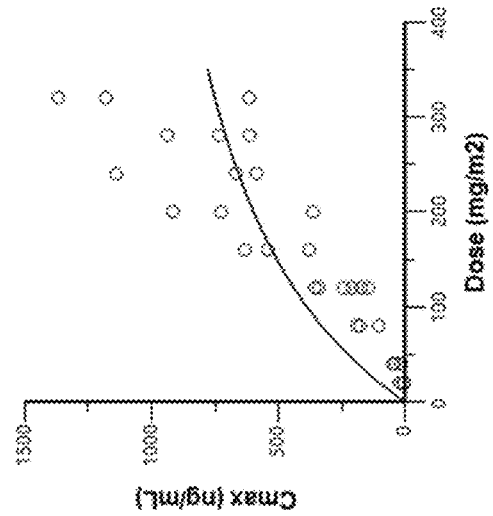
FIG. 7A is a graph showing the relationship between dose and C$_{max}$ with E$_{max}$ projection for oral irinotecan.

The observed exposure data was fit to a simple $E_{max}$ model to predict mean observed exposures at each dose level for oral irinotecan (FIG. 7A), M1 (FIG. 7B), and M2 (FIG. 7C). The observed mean $C_{max}$ of oral irinotecan showed an increase with an increase of dose as predicted, Table 9. The M1 predicted $C_{max}$ and observed mean showed an increase with an increase of dose as predicted, Table 10. The M2 $C_{max}$ was predicted to increase with an increase of dose wherein the observed mean showed a decrease in $C_{max}$ with an increase of dose, Table 11.

TABLE 9

Oral irinotecan $E_{max}$ model for predicted $C_{max}$

| Dose | Predicted $C_{max}$ | Observed Mean |
|---|---|---|
| 320 mg/m² | 752 | 1060 |
| 280 mg/m² | 643 | 763 |
| 240 mg/m² | 600 | 798 |
| 200 mg/m² | 549 | 669 |

TABLE 10

M1 $E_{max}$ model for predicted $C_{max}$

| Dose | Predicted $C_{max}$ | Observed Mean |
|---|---|---|
| 320 mg/m² | 38.8 | 38.7 |
| 280 mg/m² | 34.1 | 37.6 |

TABLE 10-continued

M1 $E_{max}$ model for predicted $C_{max}$

| Dose | Predicted $C_{max}$ | Observed Mean |
|---|---|---|
| 240 mg/m$^2$ | 31.9 | 28.3 |
| 200 mg/m$^2$ | 29.2 | 23.0 |

TABLE 11

M2 $E_{max}$ model for predicted Cmax

| Dose | Predicted $C_{max}$ | Observed Mean |
|---|---|---|
| 320 mg/m$^2$ | 183 | 70.4 |
| 280 mg/m$^2$ | 171 | 128 |
| 240 mg/m$^2$ | 162 | 136 |
| 200 mg/m$^2$ | 150 | 186 |

Example 4—Metabolic Analysis of M1 and M2 of Orally Dosed with Irinotecan

Figure 8B:
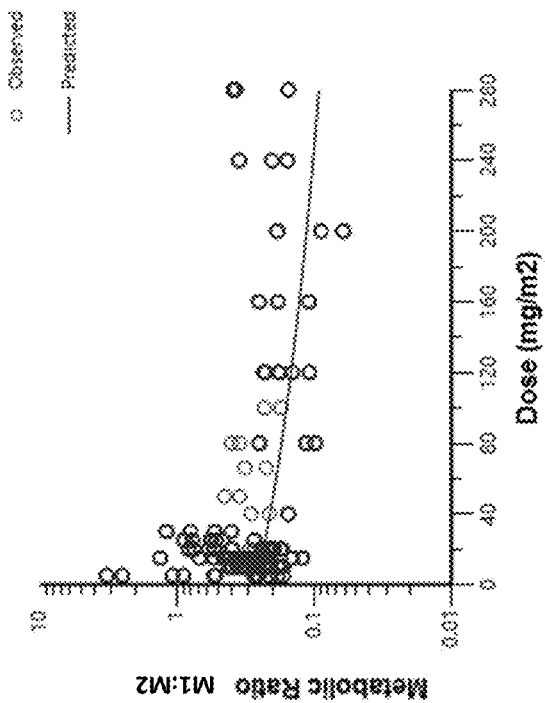
FIG. 8B is a graph showing the relationship of the metabolic ratio of M1 to M2 versus dose.
Figure 8A:
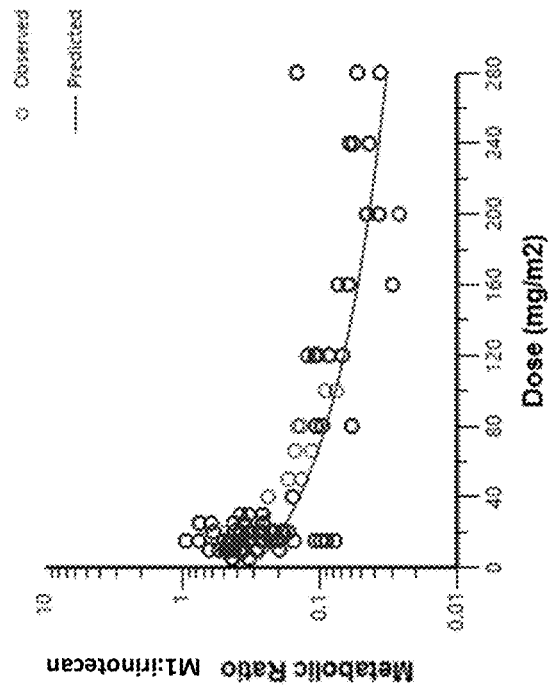
FIG. 8A is a graph showing the relationship of the metabolic ratio of M1 to oral irinotecan versus dose.

The observed metabolic ratios of Study 4 of M1 to oral irinotecan and M1 to M2 were modeled versus dose to predict the metabolic ratio trends with an increase of orally dosed irinotecan. The metabolic ratio was predicted through a comparison of M1 $AUC_{0-24}$/oral irinotecan $AUC_{0-24}$ (FIG. 8A) and M2 $AUC_{0-24}$/M1 $AUC_{0-24}$ (FIG. 8B) with correction for molecular weight. Decreasing metabolic ratios were observed with increasing irinotecan dose.

Figure 9:
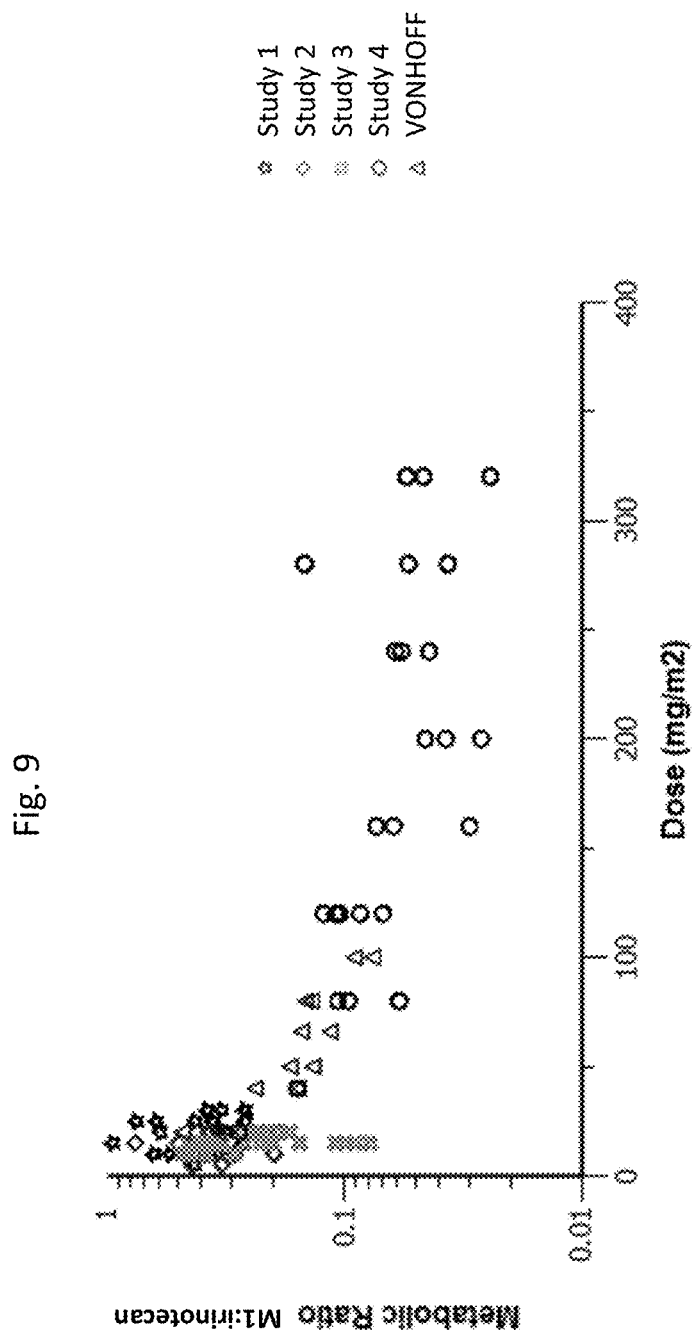
FIG. 9 is a graph showing the metabolic ratio of M1 to oral irinotecan versus dose according to Study 1-Study 4 and Vonhoff.

The observed metabolic ratios of M1 to oral irinotecan was compared across 5 studies. A plateau for the metabolic ratio of M1 to oral irinotecan was seen to continue up to a 320 mg/m$^2$ dose level, (Study 4, FIG. 9).

Example 5—Phase 1 Study of Oral Administration of Irinotecan in Combination with HM30181A A phase 1 dose escalation study was performed to determine the MTD and DLT of orally administered irinotecan in combination with 15 mg (on day 1 of a 21-day cycle) of HM30181A. The study was performed on cohorts of 3-6 subjects with advanced malignancies. Subjects had Hb (hemoglobin count) 9 gm/dL, ANC (absolute neutrophil count) 1.5×10$^9$/L, and platelets 100×10$^9$/L, as well as adequate hepatic and renal function, and ECOG (Eastern Cooperative Oncology Group Performance Status) 0-1, and were not homozygous for UGT1A1*28. Subjects were administered 15 mg of HM30181A and 20, 40, 80, 120, 160, 200, 240, 280, and 320 mg/m$^2$ of oral irinotecan.

TABLE 12

| Patient Population | | | |
|---|---|---|---|
| Number of Patients | Gender | Age (Range) | Age (Mean) |
| 30 | Male and Female | 33-78 | 60.9 |

TABLE 13

Cancer distribution of patients

| Cancer | Number of Patients |
|---|---|
| Ovarian | 6 |
| Colorectal | 4 |
| Breast | 4 |
| Endometrial | 3 |
| Pancreatic | 3 |

The median number of cycles administered was 3 (range 1-9). Treatment-related Grade 3-4 AEs (Adverse Events) were experienced by 12 (40%) of the subjects. The most common EAs were nausea (7, 23%), vomiting (6, 20%), and abdominal pain (3, 10%). Treatment-related SAEs (Serious Adverse Events) were experienced by 6 (20%) of patients. The more common SAEs were nausea or vomiting in 4 subjects.

DLTs occurred in 2 subjects at the 320 mg/m$^2$ dose level. The DLTs were neutropenia and *C. Difficile* diarrhea. Additional subjects were enrolled at the 280 mg/m$^2$ dose level to define the MTD. Acute cholinergic diarrhea was not observed. The response of stable disease was present in 9 out of 21 evaluable patients. Oral administration of HM30181A in combination with irinotecan tablets resulted in pharmacologically active concentrations of SN-38.

TABLE 14

PK at the three highest dose levels

| Dose (mg/m$^2$) N = 3 | Irinotecan | | | | SN38 | | | |
|---|---|---|---|---|---|---|---|---|
| | $t_{max}$ (h) | $C_{max}$ (ng/mL) | $AUC_{24\,h}$ (ng*h/mL) | $t_{1/2}$ (h) | $t_{max}$ (h) | $C_{max}$ (ng/mL) | $AUC_{24\,h}$ (ng*h/mL) | $t_{1/2}$ (h) |
| 240 | 3.0 | 798 | 6,960 | 11.1 | 3.0 | 28.3 | 264 | 20.0 |
| 280 | 2.0 | 763 | 6,040 | 12.2 | 1.5 | 37.6 | 293 | 18.5 |
| 320 | 3.0 | 1,055 | 11,297 | 18.7 | 2.0 | 38.5 | 300 | 20.4 |

EQUIVALENTS

The details of one or more embodiments of the invention are set forth in the accompanying description above. Although any methods and materials similar or equivalent to those described herein can be used in the practice or testing of the present disclosure, the preferred methods and materials are now described. Other features, objects, and advantages of the present disclosure will be apparent from the description and from the claims. In the specification and the appended claims, the singular forms include plural referents unless the context clearly dictates otherwise. Unless defined otherwise, all technical and scientific terms used herein have the same meaning as commonly understood by one of ordinary skill in the art to which this disclosure belongs. All patents and publications cited in this specification are incorporated by reference.

The foregoing description has been presented only for the purposes of illustration and is not intended to limit the invention to the precise form disclosed, but by the claims appended hereto.

The invention claimed is:

1. A method for treating cancer in a subject in need thereof, comprising:
   a. oral administration of irinotecan at an amount of about 5 mg/m$^2$ to about 10 mg/m$^2$, about 15 mg/m$^2$, about 20 m$^2$, about 25 mg/m$^2$, or about 30 mg/m$^2$ to the subject once a day and for 1-7 times a week; and
   b. oral administration of Compound A:

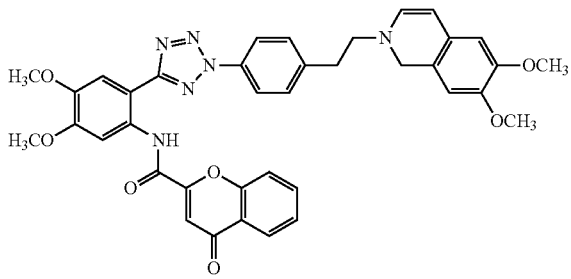 [SMILES: COc1cc2c(cc1OC)CN(CCc1ccc(-n3nnc(-c4cc(OC)c(OC)cc4NC(=O)c4cc(=O)c5ccccc5o4)n3)cc1)C=C2]

to the subject once a day and for 1-7 times a week, and wherein Compound A is administered simultaneously with or prior to the irinotecan.

2. The method of claim 1, wherein the irinotecan is administered at an amount of about 20 mg/m$^2$, about 25 mg/m$^2$, or about 30 mg/m$^2$.

3. The method of claim 1, wherein the irinotecan is administered 1-3 times per week.

4. The method of claim 1, wherein Compound A and the irinotecan are administered on the same day.

5. The method of claim 1, wherein the $AUC_{(0\to\infty)}$ of the orally administered irinotecan is equal to or greater than the $AUC_{(0\to\infty)}$ of intravenously administered irinotecan at an amount of about 25 mg/m$^2$ to about 350 mg/m$^2$ over a period of about 60 minutes.

6. The method of claim 1, wherein the subject is suffering from colorectal cancer, and wherein the plasma exposure of the orally administered irinotecan, as measured by $AUC_{(0\to\infty)}$, is equal to or greater than the plasma exposure, as measured by $AUC_{(0\to\infty)}$, of intravenously administered irinotecan at an amount of about 50 mg/m$^2$ to about 400 mg/m$^2$ over a period of about 1-24 hours once every three weeks.

7. The method of claim 1, wherein the subject is suffering from metastatic breast cancer, and wherein the plasma exposure of the orally administered irinotecan, as measured by $AUC_{(0\to\infty)}$, is equal to or greater than the plasma exposure, as measured by $AUC_{(0\to\infty)}$, of intravenously administered irinotecan at an amount of about 50 mg/m$^2$ to about 400 mg/m$^2$ over a period of about 1-24 hours once every three weeks.

8. The method of claim 1, wherein the subject is suffering from non-small cell lung cancer, and wherein the plasma exposure of the orally administered irinotecan, as measured by $AUC_{(0\to\infty)}$, is equal to or greater than the plasma exposure, as measured by $AUC_{(0\to\infty)}$, of intravenously administered irinotecan at an amount of about 50 mg/m$^2$ to about 400 mg/m$^2$ over a period of about 1-24 hours once per week for three weeks.

9. The method of claim 1, wherein the subject is suffering from adenocarcinoma of the pancreas, and wherein the plasma exposure of the orally administered irinotecan, as measured by $AUC_{(0\to\infty)}$, is equal to or greater than the plasma exposure, as measured by $AUC_{(0\to\infty)}$, of intravenously administered irinotecan at an amount of about 50 mg/m$^2$ to about 400 mg/m$^2$ over a period of about 1-24 hours once per week for three weeks.

10. The method of claim 1, wherein the subject is suffering from carcinoma of the colon, and wherein the plasma exposure of the orally administered irinotecan, as measured by $AUC_{(0\to\infty)}$, is equal to or greater than the plasma exposure, as measured by $AUC_{(0\to\infty)}$, of intravenously administered irinotecan at an amount of about 50 mg/m$^2$ to about 400 mg/m$^2$ over a period of about 1-24 hours once every three weeks.

11. The method of claim 1, wherein the subject is suffering from carcinoma of the ovary, and wherein the plasma exposure of the orally administered irinotecan, as measured by $AUC_{(0\to\infty)}$, is equal to or greater than the plasma exposure, as measured by $AUC_{(0\to\infty)}$, of intravenously administered irinotecan at an amount of about 10 mg/m$^2$ to about 200 mg/m$^2$ once every three weeks.

12. The method of claim 1, wherein the subject is suffering from colorectal cancer, and wherein the plasma exposure of the orally administered irinotecan, as measured by $AUC_{(0\to\infty)}$, is equal to or greater than the plasma exposure, as measured by $AUC_{(0\to\infty)}$, of intravenously administered irinotecan at an amount of about 100 mg/m$^2$ to about 200 mg/m$^2$ over a period of about 24 hours once every three weeks.

13. The method of claim 1, wherein the subject is suffering from AIDS-related Kaposi's Sarcoma, and wherein the plasma exposure of the orally administered irinotecan, as measured by $AUC_{(0\to\infty)}$, is equal to or greater than the plasma exposure, as measured by $AUC_{(0\to\infty)}$, of intravenously administered irinotecan at an amount of about 10 mg/m$^2$ to about 100 mg/m$^2$ over a period of about 1 hour once every three weeks, or at an amount of about 100 mg/m$^2$ to about 250 mg/m$^2$ over a period of about 3 hours once every two weeks.

14. The method of claim 1, wherein the cancer is selected from the group consisting of breast cancer, pancreatic cancer, non-small cell lung cancer, ovarian cancer, AIDS-related Kaposi sarcoma, esophageal cancer, melanoma, lymphoma, uterine cancer, peritoneal cancer, fallopian tube cancer, endometrial cancer, cervical cancer, thyroid cancer, gastric cancer, gastroesophageal junction cancer, urothelial cancer, bladder cancer, oropharynx cancer, hypopharynx cancer, larynx cancer, head and neck cancer, germ cell cancer/tumors, prostate cancer, colon cancer, rectal cancer, kidney cancer, cholangiocarcinoma (bile duct cancer), glioblastoma, leukemia, and non-Hodgkin lymphoma.

15. The method of claim 1, wherein Compound A is administered orally at an amount of about 15 mg to about 50 mg.

16. The method of claim 1, wherein Compound A is administered orally at an amount of about 15 mg.

* * * * *